United States Patent
Gayo-Fung et al.

(10) Patent No.: US 7,435,729 B2
(45) Date of Patent: Oct. 14, 2008

(54) COMPOUNDS AND METHODS FOR MODULATION OF ESTROGEN RECEPTORS

(75) Inventors: Leah Marie Gayo-Fung, San Diego, CA (US); Bernd M. Stein, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 435 days.

(21) Appl. No.: 10/731,666

(22) Filed: Dec. 8, 2003

(65) Prior Publication Data

US 2005/0004360 A1 Jan. 6, 2005

Related U.S. Application Data

(62) Division of application No. 10/085,999, filed on Feb. 27, 2002, now Pat. No. 6,686,351, which is a division of application No. 09/527,750, filed on Mar. 17, 2000, now Pat. No. 6,436,923.

(60) Provisional application No. 60/240,909, filed on Mar. 17, 1999.

(51) Int. Cl.
*A01N 43/00* (2006.01)
*A01N 43/42* (2006.01)
*A01N 43/40* (2006.01)
*A61K 31/505* (2006.01)

(52) U.S. Cl. .............. 514/217.01; 514/307; 514/277; 514/269; 514/339; 514/345; 514/357; 514/415

(58) Field of Classification Search ............... 546/144, 546/140; 540/593, 597
See application file for complete search history.

(56) References Cited

U.S. PATENT DOCUMENTS

| 3,234,090 A | 2/1966 | Huebner et al. ............... 167/58 |
| 3,274,123 A | 9/1966 | Lednicer ................... 260/326.5 |
| 3,277,106 A | 10/1966 | Bencze ........................ 260/295 |
| 5,552,412 A * | 9/1996 | Cameron et al. ............. 514/317 |
| 6,291,456 B1 * | 9/2001 | Stein et al. ............... 514/233.5 |

FOREIGN PATENT DOCUMENTS

| EP | 842 661 A2 | 5/1998 |
| EP | 1 113 007 A1 | 4/2001 |
| JP | 1143833 | 11/1987 |
| WO | WO 92/18498 | 10/1992 |
| WO | WO 96/21656 | 7/1996 |
| WO | WO 00/39120 | 7/2000 |
| WO | WO 00/55137 | 9/2000 |

OTHER PUBLICATIONS

Koehler et al. Endocrine Reviews 26(3):465-478 2005.*
Brandenberger et al., 1998, "estrogen Receptor Alpha (ER-α) and Estrogen Receptor Beta (ER-β) mRNAs in Normal Ovary, Ovarian Serous Cystandenocarcinoma and Ovarian Cancer Cell Lines: Down-Regulation of ER-β in Neoplastic Tissues", J. Clin. Endocrinol. Metab. 83:1025-8.
Chang and Prins, 1999, "Estrogen receptor-beta: implications for the prostate gland", Prostate, 40:115-24.
Clinton and Hua, 1997, "Estrogen action in human ovarian cancer." "Crit Rev Oncol. Hematol. 25:1-9.
Farhat et al., 1996, "The vascular protective effects of estrogen", FASEB J. 10:615-624.
Hata et al., 1998, "Role of Estrogen and estrogen-related growth factor in the mechanism of hormone dependency of endometrial carcinoma-cells", Oncology 55 Suppl 1, 35-44.
Iafrati et al., 1997, "Estrogen inhibits the vascular injury response in estrogen receptor alpha-deficient mice", Nature Med 3(5):545-8.
Korach et al., 1994, "Insights from the study of animals lacking functional estrogen receptor", Science 266:1524-7.
Krege et al., 1998, "Generation and reproductive phenotypes of mice lacking estrogen receptor beta", Proc. Natl. Acad. Sci. USA 95:15677-82.
Lednicer et al.,1969, "Mammalian Antifertility Agents. VI. A Novel sequence for the Preparation of 1,2-Disubstituted 3,4-Dehydronaphthalenes,", J. of Med. Chem. 12:881-885.
Mosselman et al., 1996, "ERβ Idnentification and Characterization of a Novel Human Estrogen Receptor", FEBS Lett. 392:49-53.
Nilsson et al., 1998, "Erβ : A Novel Estrogen Receptor Offers the Potential for New Drug Development", TEM 9:387-95.
Ogawa et al., 1997, "Behavioral effects of estrogen receptor gene disruption in male mice", Proc. Natl. Acad. Sci. USA 94:1476-81.
Rissman et al., 1997, "Estrogen receptor function as revealed by knockout studies: neuroendocrine and behavioral aspects", Horm. Behavior 31:232-243.
Rissman et al, 1997, "Estrogen receptors are essential for female sexual receptivity", Endocrinology 138:507-10.
Rohlff et al., 1998, "Prostate cancer cell growth inhibition by tamoxifen is associated with inhibition of protein kinase C and induction of p21 (wafl/cip 1)", Prostate 37:51-9.
Sar and Welsch, 1999, "Differential expression of estrogen receptor-beta and estrogen receptor-alpha in the rat ovary", Endocrinology 140:963-71.
Shughrue et al., 1997, "Comparative distribution of estrogen receptor alpha- and beta mRNA in the rat central nervous system", J. Comp Neurol. 388:507-25.

(Continued)

*Primary Examiner*—Michael G. Hartley
*Assistant Examiner*—Shirley V Gembeh
(74) *Attorney, Agent, or Firm*—Jones Day

(57) ABSTRACT

Compounds that modulate the estrogen receptor (ER) are disclosed, as well as pharmaceutical compositions containing the same. In a specific embodiment, the compounds are selective modulators for ER-β over ER-α. Methods are disclosed for modulating ER-β in cell and/or tissues expressing the same, including cells and/or tissue that preferentially express ER-β. More generally, methods for treating estrogen-related conditions are also disclosed, including conditions such as is breast cancer, testicular cancer, osteoporosis, endometriosis, cardiovascular disease, hypercholesterolemia, prostatic hypertrophy, prostatic carcinomas, obesity, hot flashes, skin effects, mood swings, memory loss, urinary incontinence, hairloss, cataracts, natural hormonal imbalances, and adverse reproductive effects associated with exposure to environmental chemicals.

7 Claims, 1 Drawing Sheet

OTHER PUBLICATIONS

Shughrue et al., 1997, "The distribution of estrogen receptor beta mRNA in forebrain regions of the estrogen receptor-alpha knockout mouse", Endocrinology 138:5649-52.

Shughrue et al., 1997, "Responses in the brain of estrogen receptor alpha disrupted mice", Proc. Natl. Acad. Sci. USA 94:11008-12.

Simpson et al., 1998, Responses in the brain of estrogen receptor alpha disrupted mice, J Steroid Biochem Mol Biol 64:137-45.

Sun et al., 1999, "Novel ligands that function as selective estrogens or antiestrogens for estrogen receptor alpha or estrogen receptor beta", Endocrinology 140:800-4.

Telleria et al., 1998, "Differential Expression of the Estrogen Receptors α and β in the Rat Corpus Luteum of Pregnancy: Regulation by Prolactin and Placental Lactogens", Endocrinology 139:2432-2442.

Turner et al., 1998, "Differential Responses of Estrogen Target Tissues in Rats Including Bone toClomiphene, Enclomiphene, and Zuclomiphene", Endocrinology 139:3712-20.

Yamashita et al., 1998, "Endocrine therapy in pancreatic carcinoma", Oncology 55 Suppl. 1:17-22.

Bencze et al., "Synthetic Estrogens, Implantation Inhibitors, and Hypocholesterolemic Agents. I. Tetrahydronaphtalene Series," Journal of Medicinal Chemistry 10:138-144, 1967.

Lednicer et al., "Mammalian Antifertility Agents. VI. A Novel Sequence for the Preparation of 1,2-Disubstituted 3,4-Dihydronaphthalenes," Journal of Medicinal Chemistry 12:881-885, 1969.

Angier, "New Respect For Estrogen's Influence," Science Times, The New York Times, Tuesday, Jun. 24, 1997.

Art et al., "Differential Expressions of Estrogen Receptors α and β mRNA During Differentiation of Human Osteoblast SV-HFO Cells," Endocrinology 138(11):5067-5070, 1997.

Barkhem et al., "Differential Response of Estrogen Receptor α and Estrogen Receptor β to Partial Estrogen Agonists/Antagonists," Molecular Pharmacology 54:105-112, 1998.

Cooke et al., "Mechanism of Estrogen Action: Lessons from the Estrogen Receptor-α Knockout Mouse," Biology of Reproduction 59:470-475, 1998.

Couse et al., "Tissue Distribution and Quantitative Analysis of Estrogen Receptor-α (ERα) and Estrogen Receptor-β (ERβ) Messeneger Ribonucleic Acid in the Wild-Type and ERα-Knockout Mouse," Endocrinology 138(11):4613-4621, 1997.

Cowley et al., "Estrogen Receptors α and β Form Heterodimers on DNA," The Journal of Biological Chemistry 272(32):19858-19862, 1997.

Das et al., "Estrogenic Responses in Estrogen Receptor-α Deficient Mice Reveal a Distinct Estrogen Signaling Pathway," Proc. Natl. Acad. Sci. USA 94:12786-12791, 1997.

Enmark et al., "Human Estrogen Receptor β-Gene Structure, Chromosomal Localization, and Expression Pattern," Journal of Clinical Endocrinology and Metabolism 82(12) 4258-4265, 1997.

Gustafsson, "Therapeutic Potential of Selective Estrogen Receptor Modulators," Current Opinion in Chemical Biology 2:508-511, 1998.

Katzenellenbogen and Korach, "Editorial: A New Actor in the Estrogen Receptor Drama-Enter ER-β," Endocrinology 138(3):861-862, 1997.

Kuiper et al., "Cloning of a Novel Estrogen Receptor Expressed in Rat Prostate and Ovary," Proc. Natl. Acad. Sci. USA 93:5925-5930, 1996.

Kuiper et al., "Comparison of the Ligand Binding Specificity and Transcript Tissue Distribution of Estrogen Receptors α and β," Endocrinology 138(3):863-870, 1997.

Kuiper et al., "Interaction of Estrogenic Chemicals and Phytoestrogens with Estrogen Receptor β," Endocrinology 139(10):4252-4263, 1998.

Laflamme et al., "Expression and Neuropeptidergic Characterization of Estrogen Receptors (ERαand ERβ) throughout the Rat Brain: Anatomical Evidence of Distinct Roles of Each Subtype," J. Neurobiol. 36:357-378, 1998.

Mosselman et al., "ERβ" Identification and Characterization of a Novel Human Estrogen Receptor, FEBS Letters 392:49-53, 1996.

Ogawa et al., "The Complete Primary Structure of Human Estrogen Receptor β (hERβ) and Its Heterodimerization with ER α in Vivo and in Vitro," Biochemical and Biophysical Research Communications 243:122-126, 1998.

Onoe et al., "Expression of Estrogen Recepetor β in Rat Bone," Endocrinology 138(10):4509-4512, 1997.

Paech et al., "Differential Ligand Activation of Estrogen Receptors ERα and ERβ at AP1 Sites," Science 277:1508-1510, 1997.

Petersen et al., "Identification of Estrogen Receptor $β_2$, A Functional Variant of Estrogen Receptor β Expressed in Normal Rat Tissues," Endocrinology 139(2):1082-1092, 1998.

Suen et al., "A Transcriptional Coactivator, Steroid Receptor Coactivator-3, Selectively Augments Steroid Receptor Transcriptional Activity," The Journal of Biological Chemistry 273(42):27645-27653, 1998.

Telleria et al., "Differential Expression of the Estrogen Receptors α and β in the Rat Corpus Luteum of Pregnancy: Regulation by Prolactin and Placental Lactogens," Endocrinology 139:2432-2442, 1998.

Tong et al., "QSAR Models for Binding of Estrogenic Compounds to Estrogen Receptor α and β Subtypes," Endocrinology 138(9):4022-4025, 1997.

Tremblay et al., "EM-800, a Novel Antiestrogen, Acts as a Pure Antagonist of the Transcriptional Functions of Estrogen Receptors α and β," Endocrinology 139(1):111-118, 1998.

Watanabe et al., "Agonistic Effect of Tamoxifen Is Dependent on Cell Type, ERE-Promoter Context, and Estrogen Receptor Subtype: Functional Difference between Estrogen Receptors α and β," Biochemical and Biophysical Research Communications 236:140-145, 1997.

CAS printout for Hoshino et al., Tetrahedron; Asymmetry 4: 933-42, 1993.

CAS printout for Sainsbury et al., Tetrahedron 48: 8739-50, 1992.

CAS printout for Tantisewie et al., J. Nat. Prod. 53: 553-8, 1990.

CAS printout for Akasu et al., Japanese Patent No. 1,143,833.

CAS printout for Mandell et al., Heterocycles 26: 713-720, 1987.

CAS printout for Guinaudeau et al., Tetrahedron 40: 1975-82, 1984.

CAS printout for U.S. Patent App. No. 577,817.

CAS printout for Bruneton et al., J. Org. Chem. 48: 3957-60, 1983.

CAS printout for Hsu et al., Helv. Chim. Acta 65: 1576-89, 1982.

CAS printout for Kashdan et al., J. Org. Chem. 47: 2638-43, 1982.

CAS printout for Razdan et al., J. Org. Chem. 44: 3730-1, 1979.

CAS printout for Popp et al., J. Heterocycl. Chem. 15: 429-32, 1978.

CAS printout for Gibson et al., J. Chem. Soc. 16: 2234-8, 1970.

CAS printout for Shavel et al., U.S. Patent No. 3,438,989.

CAS printout for Weisbach et al., J. Med. Chem. 11: 752-60, 1968.

CAS printout for Battersby et al., J. Chem. Soc. 18: 1739-44, 1967.

* cited by examiner

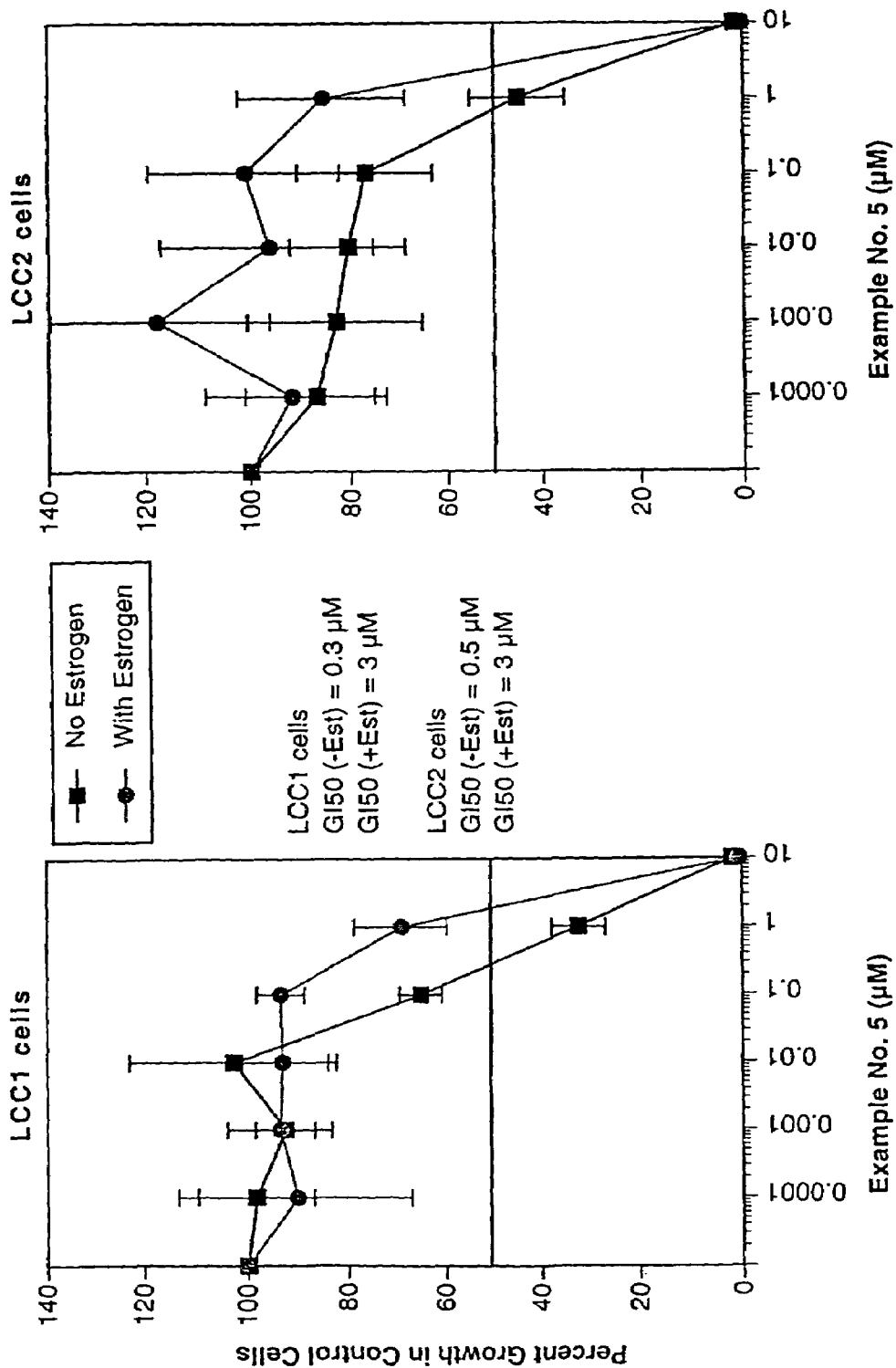

COMPOUNDS AND METHODS FOR MODULATION OF ESTROGEN RECEPTORS

CROSS REFERENCE TO RELATED APPLICATION

This application is a division of U.S. application Ser. No. 10/085,999, filed Feb. 27, 2002 now U.S. Pat. No. 6,686,351, allowed, which is a division of U.S. application Ser. No. 09/527,750, filed Mar. 17, 2000, now U.S. Pat. No. 6,436,923, issued Aug. 20, 2002, which claims the benefit of U.S. Provisional Application No. 60/240,909, filed Mar. 17, 1999, the disclosure of each of which is incorporated by reference herein in its entirety.

TECHNICAL FIELD

This invention is generally directed to estrogen antagonists and agonists, including pharmaceutical compositions and uses thereof, and more specifically to compounds which selectively modulate estrogen receptor-beta (ER-β) activity.

BACKGROUND OF THE INVENTION

The estrogen hormone has a broad spectrum of effects on tissues in both females and males. Many of these biological effects are positive, including maintenance of bone density, cardiovascular protection, central nervous system (CNS) function, and the protection of organ systems from the effects of aging. However, in addition to its positive effects, estrogen also is a potent growth factor in breast and endometrium that increases the risk of cancer.

Until recently, it has been assumed that estrogen binds to a single estrogen receptor (ER) in cells, causing conformational changes that result in release from heat shock proteins and binding of the receptor as a dimer to the so-called estrogen response element in the promoter region of a variety of genes. Further, pharmacologists have generally believed that non-steroidal small molecule ligands compete for binding of estrogen to ER, acting as either antagonists or agonists in each tissue where the estrogen receptor is expressed. Thus, such ligands have traditionally been classified as either pure antagonists or agonists. This is no longer believed to be correct.

Progress over the last few years has shown that ER associates with co-activators (e.g., SRC-1, CBP and SRA) and co-repressors (e.g., SMRT and N—CoR) that modulate the transcriptional activity of ER in a tissue-specific and ligand-specific manner. In addition, evidence now suggests that the majority of estrogen-regulated genes do not have a classical estrogen response element. In such cases, ER interacts with the transcription factors critical for regulation of these genes. Transcription factors known to be modulated in their activity by ER include, for example, AP-1, NF-κB, C/EBP and Sp-1.

Given the complexity of ER signaling, as well as the various types of tissue that express ER and its co-factors, it is now believed that ER ligands can no longer simply be classified as either pure antagonists or agonists. Therefore, the tem "selective estrogen receptor modulator" (SERM) has been coined. SERMs bind to ER, but may act as an agonist or antagonist of estrogen in different tissues and on different genes. For example, two of the most well known drugs that behave as SERMs are Tamoxifen (Astra-Zeneca Pharmaceuticals) and Raloxifene (Eli Lilly & Co.). Studies with these two compounds, as well as other SERMs now in development, have demonstrated that the affinity of a SERM for its receptor in many cases does not correlate with its biological activity. Therefore, ligand-binding assays traditionally used in screening for novel ER modulators have not distinguished between tissue-selectivity and agonist/antagonist behavior.

In addition to Tamoxifen and Raloxifene, a number of other compounds have been disclosed to have estrogenic activity, such as those disclosed by Lednicer et al. (*J. Med. Chem.* 12, 881, 1969) and Bencze et al. (*J. Med. Chem.* 10, 138, 1967), as well as those disclosed in U.S. Pat. Nos. 3,234,090, 3,277, 106, and 3,274,213. Further, estrogen agonists/antagonists of the following structure are disclosed in published PCT WO 96/21656 to Cameron et al.:

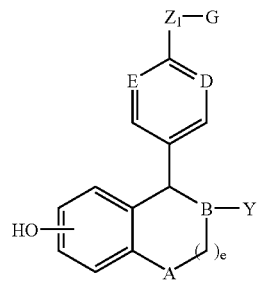

More recently, a second estrogen receptor, ER-β, has been identified and cloned (Katzenellenbogen and Korach *Endocrinology* 138, 861-2 (1997); Kuiper et al., *Proc. Natl. Acad. Sci. USA* 93, 5925-5930, 1996; Mosselman et al., *FEBS Lett.* 392, 49-53, 1996). ER-β, and the classical ER renamed ER-α, have significantly different amino acid sequences in the ligand binding domain and carboxy-terminal transactivation domains (~56% amino acid identity), and only 20% homology in their amino-terminal transactivation domain. This suggests that some ligands may have higher affinity to one receptor over the other. Further, ligand-dependent conformational changes of the two receptors, and interaction with co-factors, will result in very different biological actions of a single ligand. In other words, a ligand that acts as an agonist on ER-α may very well serve as an antagonist on ER-β. An example of such behavior has been described by Paech et al. (*Science* 277, 1508-1510, 1997). In that paper, estrogen is reported to activate an AP-1 site in the presence of ER-α, but to inhibit the same site in the presence of ER-β. In contrast, Raloxifene (Eli Lilly & Co.) and Tamoxifen and ICI-182,780 (Zeneca Pharmaceuticals) stimulate the AP-1 site through ER-β, but inhibit this site in the presence of ER-α. Another example has been described by Sun et al. (*Endocrinology* 140, 800-4, 1999), wherein the R,R-enantiomer of a tetrahydrochrysene is reported to be an agonist on ER-α, but a complete antagonist on ER-β, while the S,S-enantiomer is an agonist on both receptors.

Furthermore, ER-α and ER-β have both overlapping and different tissue distributions, as analyzed predominantly by RT-PCR or in-situ hybridization due to a lack of good ER-β antibodies. Some of these results, however, are controversial, which may be attributable to the method used for measuring ER, the species analyzed (rat, mouse, human) and/or the differentiation state of isolated primary cells. Very often tissues express both ER-α and ER-β, but the receptors are localized in different cell types. In addition, some tissues (such as kidney) contain exclusively ER-α, while other tissues (such as uterus, pituitary and epidymis) show a great predominance of ER-α (Couse et al., *Endocrinology* 138, 4613-4621, 1997; Kuiper et al., *Endocrinology* 138, 863-870, 1997). In contrast, tissues expressing high levels of ER-β include prostate, testis, ovaries and certain areas of the brain (Brandenberger et al., *J.*

*Clin. Endocrinol. Metab.* 83, 1025-8, 1998; Enmark et al., *J. Clinic. Endocrinol. Metabol.* 82, 4258-4265, 1997; Laflamme et al., *J. Neurobiol.* 36, 357-78, 1998; Sar and Welsch, *Endocrinology* 140, 963-71, 1998; Shughrue et al., *Endocrinology* 138, 5649-52, 1997a; Shughrue et al., *J. Comp. Neurol.* 388, 507-25, 1997b); Chang and Prins, *The Prostate* 40, 115-124, 1999.

The development of ER-α (Korach, *Science* 266, 1524-1527, 1994) and ER-β (Krege et al., *Proc. Natl. Acad. Sci. USA* 95, 15677-82, 1998) knockout mice further demonstrate that ER-β has different functions in different tissues. For example, ER-α knockout mice (male and female) are infertile, females do not display sexual receptivity and males do not have typical male-aggressive behavior (Cooke et al., *Biol. Reprod.* 59, 470-5, 1998; Das et al., *Proc. Natl. Acad. Sci. USA* 94, 12786-12791, 1997; Korach, 1994; Ogawa et al., *Proc. Natl. Acad. Sci. USA* 94, 1476-81, 1997; Rissman et al., *Endocrinology* 138, 507-10, 1997a; Rissman et al., *Horm. Behav.* 31, 232-243, 1997b). Further, the brains of these animals still respond to estrogen in a pattern that is similar to that of wild type animals (Shughrue et al., *Proc. Natl. Acad. Sci. USA* 94, 11008-12, 1997c), and estrogen still inhibits vascular injury caused by mechanical damage (Iafrati et al., *Nature Med.* 3, 545-8, 1997). In contrast, mice lacking the ER-β develop normally, are fertile and exhibit normal sexual behavior, but have fewer and smaller litters than wild-type mice (Krege et al., 1998), have normal breast development and lactate normally. The reduction in fertility is believed to be the result of reduced ovarian efficiency, and ER-β is the predominant form of ER in the ovary, being localized in the granulosa cells of maturing follicles. ER-β knockout mice display signs of prostatic hyperplasia with aging, which suggests that ER-β may normally protect against abnormal growth (Krege et al., 1998). ER-α/ER-β double knockout mice are viable, but infertile, and display a postnatal reversal of the ovaries (Couse et al., *Science* 286, 2328-2331, 1999).

In summary, compounds which serve as estrogen antagonists or agonists have long been recognized for their significant pharmaceutical utility in the treatment of a wide variety of estrogen-related conditions, including conditions related to the brain, bone, cardiovascular system, skin, hair follicles, immune system, bladder and prostate (Barkhem et al., *Mol. Pharmacol.* 54, 105-12, 1998; Farhat et al., *FASEB J.* 10, 615-624, 1996; Gustafsson, *Chem. Biol.* 2, 508-11, 1998; Sun et al., 1999; Tremblay et al., *Endocrinology* 139, 111-118, 1998; Turner et al., *Endocrinology* 139, 3712-20, 1998). In addition, a variety of breast and non-breast cancer cells have been described to express ER, and serve as the target tissue for specific estrogen antagonists (Brandenberger et al., 1998; Clinton and Hua, *Crit. Rev. Oncol. Hematol.* 25, 1-9, 1997; Hata et al., *Oncology* 55 *Suppl* 1, 35-44, 1998; Rohlff et al., *Prostate* 37, 51-9, 1998; Simpson et al., *J Steroid Biochem Mol Biol* 64, 137-45,1998; Yamashita et al., *Oncology* 55 *Suppl* 1, 17-22, 1998).

With the recent identification of the ER-β, and the recognition that ER-α and ER-β have different biological roles, ER-selective modulators would similarly possess significant clinical utility. Since ER-β is expressed strongly in a number of tissues including prostrate, bladder, ovary, testis, lung, small intestine, vascular endothelium, and various parts of the brain, compounds that selectively modulate ER-β would be of clinical importance in the treatment of a variety of diseases or conditions, such as prostate cancer, testicular cancer, cardiovascular diseases, neurodegenerative disorders, urinary incontinence, CNS, GI tract conditions, and bone and other cancers. Such compounds would have minimal effect on tissues that contains ER-α, and thus exhibit different side-effect profiles. For example, while estrogen replacement therapy is associated with a variety of beneficial effects (such as bone protection, cardiovascular effect, prevention of hot flashes, dementia, bone metabolism, etc.), such therapy also has adverse effects (such as breast and endometrial cancer, thrombosis, etc.). Some of these adverse effects are believed to be mediated by ER-α or ER-β specific mechanisms. Thus, ER-β antagonists or agonists will display different therapeutic profiles compared to ER-α antagonists or agonists, and would be preferentially beneficial in tissues expressing high levels of ER-β (see, e.g., Nilsson et al., *TEM* 9, 387-395, 1998; Chang and Prins, *The Prostate* 40, 115-124, 1999). Furthermore, a number of investigators have shown that environmental chemicals and phytoestrogens preferentially interact with ER-β by triggering biological responses similar to that of estrogen (see, e.g., Kuiper et al., *Endocrinology* 139, 4252-4263, 1998). Thus, compounds that antagonize ER-β would also be important in regulating interactions with chemicals, affecting health, reproductive capacity and the like.

Accordingly, there is a need in the art for estrogen antagonists and agonists, including pharmaceutical compositions and methods relating to the use thereof. There is also a need for compounds that selectively modulate ER-β. The present invention fulfills these needs, and provides further related advantages.

SUMMARY OF THE INVENTION

In brief, the present invention is generally directed to estrogen antagonists and/or agonists, including pharmaceutical compositions containing the same, as well as to methods for treating estrogen-related conditions. Such conditions are more specifically discussed below, and generally include (but are not limited to) obesity, breast cancer, osteoporosis, endometriosis, cardiovascular disease, prostate cancer, menopausal syndromes, hair loss (alopecia), type-II diabetes, Alzheimer's disease, urinary incontinence, GI tract conditions, spermatogenesis, vascular protection after injury, endometriosis, learning and memory, CNS effects, plasma lipid levels, acne, cataracts, hirsutism, other solid cancers (such as colon, lung, ovarian, testis, melanoma, CNS, and renal), multiple myeloma, and lymphoma.

More specifically, the estrogen antagonists and/or agonists of this invention are compounds having the following structure (I):

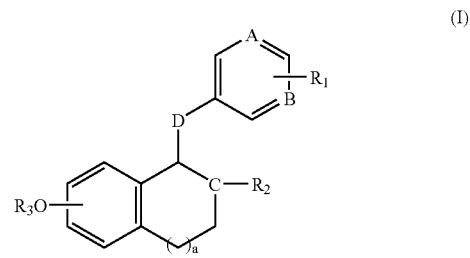

including stereoisomers and pharmaceutically acceptable salts thereof, wherein A, B, C, D, $R_1$, $R_2$, $R_3$ and α are as identified in the following detailed description. In addition, pharmaceutical compositions are also disclosed containing one or more compounds of structure (I), in combination with a pharmaceutically acceptable carrier or diluent.

In another embodiment, methods are disclosed for modulating cells and/or tissues that express ER-β by contacting the cell and/or tissue with an effective amount of a compound of structure (I). In an embodiment, the cell and/or tissue preferentially expresses ER-β over ER-α, such as cell and/or tissue of bone, bladder, uterus, ovary, prostate, testis, epididymis, gastrointestinal (GI) tract, kidney, breast, heart, vessel wall, immune system, lung, pituitary, hippocampus and hypothalamus.

In still a further embodiment, the present invention discloses methods for treating an estrogen-related condition by administering to an warm-blooded animal in need thereof an effective amount of a compound of structure (I) formulated as a pharmaceutical composition suitable for administration to the animal. In representative embodiments, the estrogen-related condition is breast cancer, osteoporosis, endometriosis, cardiovascular disease, hypercholesterolemia, prostatic hypertrophy, obesity, prostate cancer, menopausal syndromes, type-II diabetes, Alzheimer's disease, urinary incontinence, GI tract conditions, spermatogenesis, vascular protection after injury, endometriosis, learning and memory, CNS effects, plasma lipid levels, acne, hirsutism, other solid cancers (such as colon, lung, ovarian, testis, melanoma, CNS, and renal), multiple myeloma, lymphoma, prostatic carcinomas, obesity, hot flashes, skin effects, mood swings, memory loss, and/or adverse reproductive effects associated with exposure to environmental chemicals. In other embodiments, methods are disclosed for inhibiting a cyctokine, such as IL-6 and GM-CSF, in an animal in need thereof, as well as methods for treating cancer associated therewith.

These and other aspects of this invention will be evident upon reference to the attached drawings and the following detailed description. To that end, certain references are cited herein each of which are hereby incorporated by reference in their entirety.

BRIEF DESCRIPTION OF THE DRAWINGS

FIGS. 1A and 1B illustrate proliferation of Tamoxifen resistant LCC1 and LCC2 breast cancer cell lines when exposed to a representative compound of this invention.

DETAILED DESCRIPTION OF THE INVENTION

As mentioned above, the present invention is directed to compounds that have activity as estrogen antagonists and/or agonists, as well as pharmaceutical compositions containing one or more of such compounds and methods related to the same. As estrogen antagonists and/or agonists, the compounds of this invention have utility in the treatment of a wide range of estrogen-related conditions. In this context, the term "treatment" includes both treatment and/or prevention of an estrogen-related condition. Thus, the compounds of this invention may be administered as a therapeutic and/or prophylactic agent. An estrogen "agonist" is a compound that binds to ER and mimics the action of estrogen in one or more tissues, while an "antagonist" binds to ER and blocks the action of estrogen in one or more tissues. Further, the term "estrogen-related condition" encompasses any condition associated with elevated or depressed levels of estrogen, a selective estrogen receptor modulators (SERM), ER-α or ER-β.

Accordingly, the compounds of the present invention may also be used within a method for treating estrogen-related conditions, including (but not limited to) breast cancer, osteoporosis, endometriosis, cardiovascular disease, hypercholesterolemia, prostatic hypertrophy, prostatic carcinomas, obesity, hot flashes, skin effects, mood swings, memory loss, menopausal syndromes, hair loss (alopecia), type-II diabetes, Alzheimer's disease, urinary incontinence, GI tract conditions, spermatogenesis, vascular protection after injury, endometriosis, learning and memory, CNS effects, plasma lipid levels, acne, hirsutism, other solid cancers (such as colon, lung, ovarian, testi, melanoma, CNS, and renal), multiple myeloma, cataracts, lymphoma, and adverse reproductive effects associated with exposure to environmental chemicals.

In one aspect of this invention, it has been found that the compounds of this invention are selective estrogen receptor modulators and, more specifically, are selective to ER-β. Accordingly, in this aspect of the invention, the compounds have utility as agents for treatment of osteoporosis, hormonally regulated cancer, combination treatment of cancer (such as with taxol cisplatin or chemotherapy), women's gynecologic health issues, and health conditions resulting from exposure to environmental chemicals.

The compounds of this invention have the following structure (I):

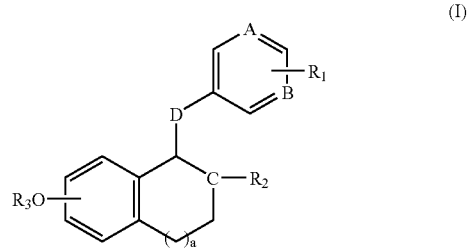

including stereoisomers and pharmaceutically acceptable salts thereof,
wherein
  a is 0, 1 or 2;
  A, B and C are independently CH, CR or N;
  D is —(CH$_2$)$_r$— or —(CH$_2$)$_n$C(=O)(CH$_2$)$_m$—;
  R$_1$ represents one or two substituents independently selected from —X—Y;
  R$_2$ is C$_{1-8}$alkyl, C$_{6-12}$aryl, C$_{7-12}$aralkyl, —C(=O)R$_5$, a five- or six-membered heterocycle or heterocyclealkyl containing up to two heteroatoms selected from O, NR$_c$ and S(O)$_q$, or a bicyclic ring system contain a five- or six-membered heterocycle fused to phenyl, wherein each of the above groups are optionally substituted with one to three substituents independently selected from —X—Y or R$_4$; and
  R$_3$ is hydrogen, —R$_6$, —(CH$_2$)$_s$C(=O)R$_6$, —(CH$_2$)$_s$C(=O)OR$_6$, —(CH$_2$)$_s$C(=O)NR$_6$R$_7$, —(CH$_2$)$_s$C(=O)NR$_6$(CH$_2$)$_n$C(=O)R$_7$R$_8$, —(CH$_2$)$_s$NR$_6$C(=O)R$_7$, —(CH$_2$)$_s$NR$_6$C(=O)NR$_7$R$_8$, —(CH$_2$)$_s$NR$_6$R$_7$, —(CH$_2$)$_s$OR$_6$, —(CH$_2$)$_s$SO$_2$R$_6$ or —(CH$_2$)$_s$SO$_2$NR$_6$R$_7$;
and wherein
  R$_4$ is at each occurrence independently halogen, hydroxy, carboxy, C$_{1-6}$alkyl, C$_{1-4}$alkoxy, C$_{1-4}$haloalkyl, C$_{1-4}$acyloxy, C$_{1-4}$thio, C$_{1-4}$alkylsulfinyl, C$_{1-4}$alkylsulfonyl, (hydroxy)C$_{1-4}$alkyl, C$_{6-12}$aryl, C$_{7-12}$aralkyl, —C(=O)OH, —C(=O)OR, —OC(=O)R, —C(=O)NHR, —C(=O)NRR, —C(=O)NHOR, —SO$_2$NHR, —NHSO$_2$R, —CN, —NO$_2$, —NH$_2$, C$_{1-4}$alkylamino, C$_{1-4}$dialkylamino, —NHC(=O)R, NHC(=O)(CH$_2$)$_s$ (five- or six-membered heterocycle), a five- or six-membered heterocycle, or a five- or six-membered heterocycle fused to phenyl;

$R_5$, $R_6$, $R_7$ and $R_8$ are at each occurrence independently hydrogen, $C_{1-8}$alkyl, $C_{6-12}$aryl, $C_{7-12}$aralkyl, or a five- or six-membered heterocycle or heterocyclealkyl containing up to two heteroatoms selected from O, $NR_e$ and $S(O)_q$, wherein each of the above groups are optionally substituted with one to three substituents independently selected from $R_4$;

X is at each occurrence independently a direct bond;
—$(CH_2)_nZ(CH_2)_m$—;
—$O(CH_2)_nZ(CH_2)_m$—;
—$S(CH_2)_nZ(CH_2)_m$—;
—$NR_c(CH_2)_nZ(CH_2)_m$—;
—$O(CH_2)_nCR_aR_b$—;
—$NR_c(CH_2)_nCR_aR_b$—;
—$OCHR_cCHR_d$—; or
—$SCHR_cCHR_d$—;

Y is at each occurrence independently halogen;

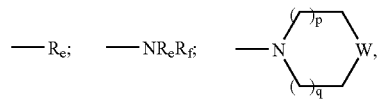

optionally fused on adjacent carbon atoms with one or two phenyl or cycloalkyl rings, and with each carbon optionally and independently substituted with carbonyl or with one or two substituents independently selected from $R_4$, with any two $R_4$ substituents on a single carbon atom optionally being taken together to form a five- or six-membered heterocycle, and with each nitrogen atom optionally and independently substituted with $R_4$, wherein W is —$NR_e$—, —O—, —S— or —$CR_eR_f$—; or a bridged or fused $C_{5-12}$bicyclic amine optionally substituted with one to three substituents independently selected from $R_4$;

or where —X—Y is

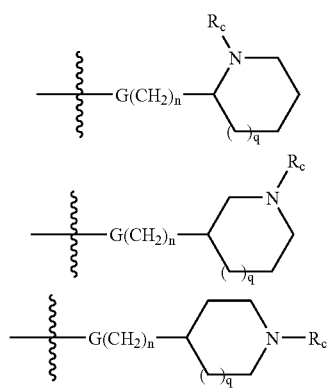

Z is $CH_2$, CH=CH, C—C, O, $NR_c$, $S(O)_q$, C(=O), $C(OH)R_c$, $C(=O)NR_c$, $NR_cC(=O)$, $C(=O)NR_c$, $NR_cC(=O)$ or

G is O, S or $NR_e$;

n and m are at each occurrence independently 0, 1, 2 or 3;

p is at each occurrence independently 1, 2 or 3;

q is at each occurrence independently 0, 1 or 2;

r is at each occurrence independently 1, 2, 3, 4 or 5;

s is at each occurrence independently 0, 1, 2, 3 or 4;

R is at each occurrence independently $C_{1-6}$alkyl;

$R_a$ and $R_b$ are at each occurrence independently $C_{1-8}$alkyl or taken together form a $C_{3-8}$acyclic alkyl;

$R_c$ and $R_d$ are at each occurrence independently hydrogen or $C_{1-4}$alkyl; and $R_e$ and $R_f$ are at each occurrence independently hydrogen, $C_{6-12}$aryl, $C_{1-8}$alkyl, $C_{7-12}$aralkyl, a five- or six-membered heterocycle, or a five- or six-membered heterocycle fused to phenyl; or wherein $R_e$ or $R_f$ form a 3-8 membered nitrogen-containing heterocyclic alkyl with $R_a$ or $R_b$; and wherein each $R_e$ and $R_f$ are optionally substituted with up to three substituents independently selected from $R_4$.

As used herein, the above terms have the following meaning:

"Halogen" means F, Cl, Br and I.

"$C_{1-4}$alkyl", "$C_{1-6}$alkyl" and "$C_{1-8}$alkyl" means a straight chain or branched, cyclic or non-cyclic, saturated or unsaturated carbon chain having from 1 to 4, 6 or 8 carbon atoms, respectively. In one embodiment, the $C_{1-X}$alkyl (where X is 4, 6 or 8 as disclosed above) is a fully saturated, straight chain alkyl such as methyl, ethyl, n-propyl, r-butyl, n-pentyl, n-hexyl and the like. In another embodiment, the $C_{1-X}$alkyl is a fully saturated cyclic alkyl such as cyclopropyl, cyclobutyl, cyclopentyl, cyclohexyl, and the like, or an alkyl(cycloalkyl) moiety such as methylenecyclopropyl, methylenecyclobutyl, methylenecyclopentyl, methylenecyclohexyl, and the like, or an unsaturated cyclic alkyl. In still a further embodiment, the $C_{1-X}$ alkyl is a fully saturated, branched alkyl such as iso-propyl, iso-butyl, tert-butyl, iso-pentyl, iso-hexyl, and the like. In yet another embodiment, the $C_{1-X}$alkyl is an unsaturated straight chain alkyl such as ethylenyl, propylenyl, 1-butenyl, 1-pentenyl, 1-hexenyl, and the like.

"$C_{6-12}$aryl" means a carbocyclic aromatic moiety containing from 6 to 12 carbon atoms. In one embodiment, the $C_{6-12}$aryl is phenyl, tetralinyl or napthalenyl, and typically is phenyl.

"$C_{7-12}$aralkyl" means an arene containing from 7 to 12 carbon atoms, and has both aliphatic and aromatic components. In one embodiment, the $C_{7-12}$ aralkyl is benzyl, ethylenephenyl, propylenephenyl, and the like.

"Five- or six-membered heterocycle" means a heterocyclic ring containing up to two heteroatoms selected from O, $NR_c$ and $S(O)_q$, and wherein the number of carbon and heteroatoms of the ring total 5 or 6, including both saturated and unsaturated, aromatic and non-aromatic ring systems, such as pyridinyl, pyrimidinyl, furanyl, thienyl, triazenyl, imidazolyl, thiazolyl, pyrazolyl, pyridazinyl, pyrazinyl, and the like.

"Five- or six-membered heterocyclealkyl" means a $C_{1-6}$alkyl having at least one hydrogen replaced with a five- or six-membered heterocycle, such as —$CH_2$(hererocycle), and the like.

"$C_{1-X}$alkoxy" means a —$O(C_{1-X}$alkyl), where x is 4, 6 or 8.

"$C_{1-4}$acyloxy" means —$OC(=O)C_{1-4}$alkyl.

"$C_{1-4}$thio" means —$SC_{1-4}$alkyl.

"$C_{1-4}$alkylsulfinyl" means —$SOC_{1-4}$alkyl.

"$C_{1-4}$alkylsulfonyl" means —$SO_2C_{1-4}$alkyl.

"(hydroxy)$C_{1-4}$alkyl" means $C_{1-4}$alkyl wherein a hydrogen atom has been substituted by hydroxyl.

"$C_{1-4}$alkylamino" means —$NHC_{1-4}$alkyl.

"$C_{1-4}$dialkylamino" means —$N(C_{1-4}$alkyl)($C_{1-4}$alkyl).

"$C_{1-4}$haloalkyl" means a $C_{1-4}$alkyl having at least one hydrogen replaced with halogen, such as trifluoromethyl and the like.

In one aspect of structure (I), A and B are both CH, C is N, D is —$CH_2$—, and the compounds of this invention have the following structure (IIa) when a is 1, (IIb) when a is 0, and (IIc) when a is 2:

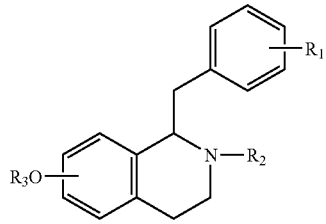
(IIa)

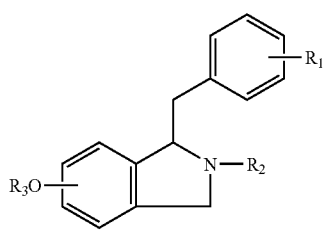
(IIb)

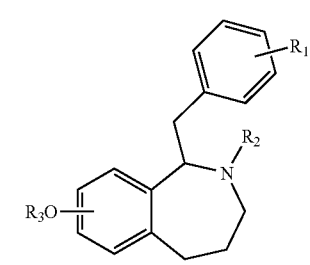
(IIc)

In other aspects of this invention, the compounds of structure (I) have the following structures (III), (IV), (V) or (VI):

(III)

(IV)

-continued

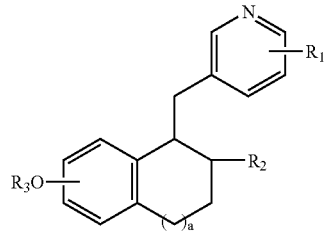
(V)

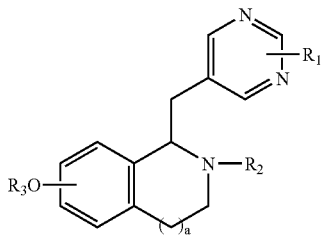
(VI)

In one embodiment of structure (IIa), $R_2$ is phenyl optionally substituted with one, two or three substituents independently selected from $R_4$, $R_3$ is hydrogen, and the compounds of this invention have the following structure (IIa-1):

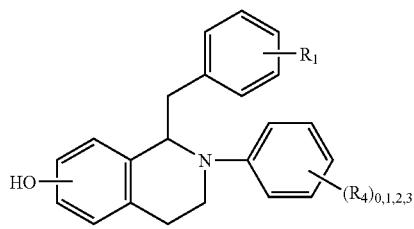
(IIa-1)

In another embodiment of structure (IIa), $R_2$ is pyridinyl optionally substituted with one, two or three substituents independently selected from $R_4$, $R_3$ is hydrogen, and the compounds of this invention have the following structures (IIa-2) or (IIa-3):

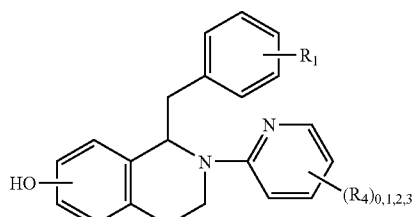
(IIa-2)

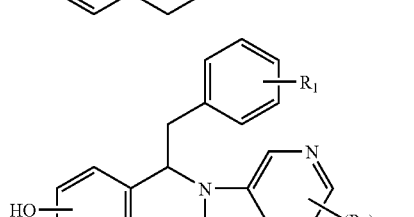
(IIa-3)

In another embodiment of structure (IIa), $R_1$ is

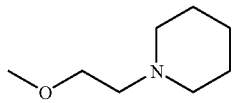

at the 4-position, $R_3$ is hydrogen, and the compounds of this invention have the following structure (IIa-4):

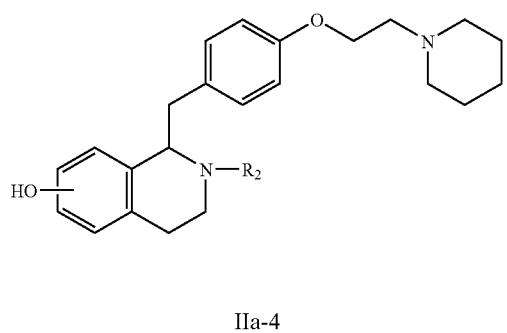

IIa-4

In yet further embodiments, the compounds of this invention have the following structure (IIa-5) or (IIa-6):

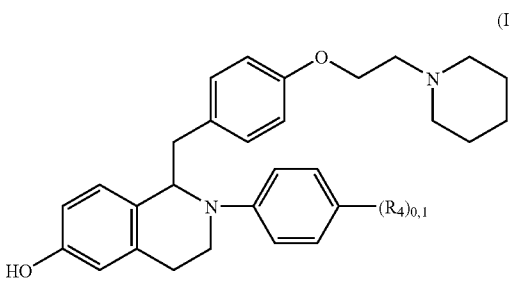

(IIa-5)

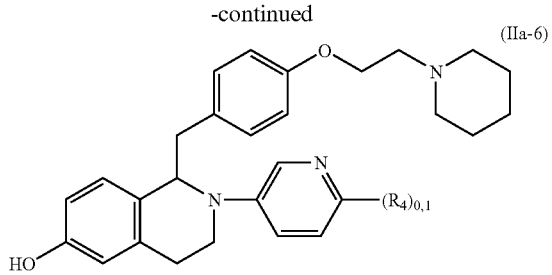

(IIa-6)

In still further embodiments, the compounds of this invention have the following structure (IIa-7):

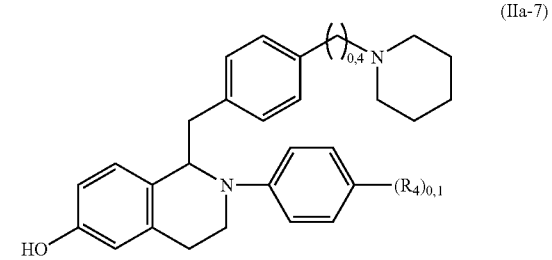

In another embodiment, compounds of this invention have the following structure (VII):

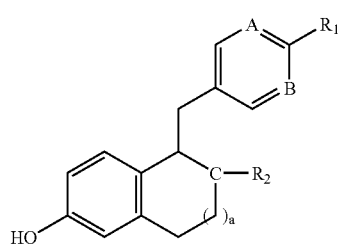

For purpose of illustration, representative compounds of structure (VII) are set forth in the Table 1.

TABLE 1

| | Representative Compounds of Structure (VII) | | | | | |
|---|---|---|---|---|---|---|
| Cpd No. | a | A | B | C | $R_1$ | $R_2$ |
| 100 | 1 | CH | CH | N | Halogen | Phenyl |
| 101 | 1 | CH | CH | N | ⌇O-CH2CH2-N(piperidine) | Phenyl |
| 102 | 1 | CH | CH | N | ⌇O-CH2CH2-N(piperidine) | 4-Fluorophenyl |

TABLE 1-continued
Representative Compounds of Structure (VII)
| Cpd No. | a | A | B | C | R₁ | R₂ |
|---|---|---|---|---|---|---|
| 103 | 1 | CH | CH | N | 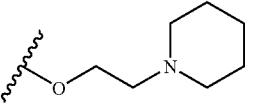 | 2-Methoxypyridin-5-yl |
| 104 | 2 | CH | CH | N | 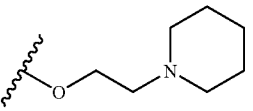 | 4-Fluorophenyl |
| 105 | 0 | CH | CH | N | 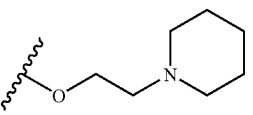 | 4-Fluorophenyl |
| 106 | 1 | CH | CH | N | 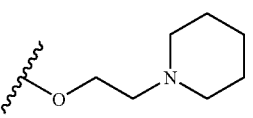 | 2-Hydroxypyridin-5-yl |
| 107 | 1 | CH | CH | N | 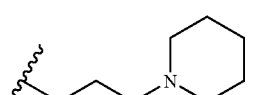 | 2-Aminopyridin-5-yl |
| 108 | 1 | CH | CH | N | 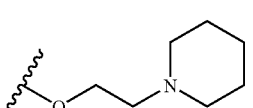 | 4-Methoxyphenyl |
| 109 | 1 | CH | CH | N | 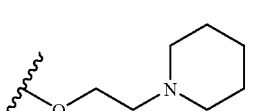 | 4-Hydroxyphenyl |
| 110 | 1 | CH | CH | N | 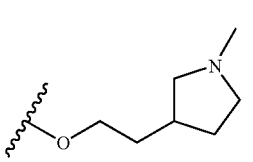 | 4-Fluorophenyl |
| 111 | 1 | CH | CH | N | 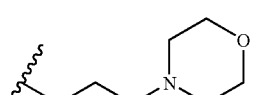 | 4-Fluorophenyl |
| 112 | 1 | CH | CH | N | 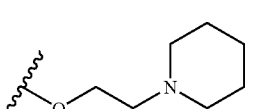 | Cyclohexyl |
| 113 | 1 | CH | CH | N | 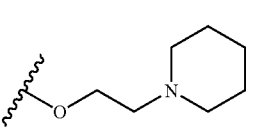 | Benzyl |
| 114 | 1 | CH | CH | N |  | 2-Thienyl |

TABLE 1-continued
Representative Compounds of Structure (VII)
| Cpd No. | a | A | B | C | R₁ | R₂ |
|---|---|---|---|---|---|---|
| 115 | 1 | CH | CH | N | 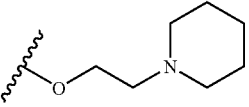 | 3-Thienyl |
| 116 | 1 | N | CH | N | 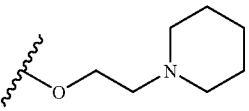 | 4-Fluorophenyl |
| 117 | 1 | N | N | N | 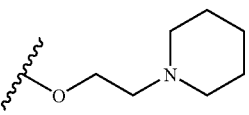 | 4-Fluorophenyl |
| 118 | 1 | CH | CH | N | 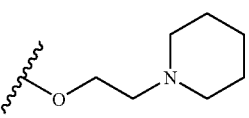 | Isopropyl |
| 119 | 1 | CH | CH | N | 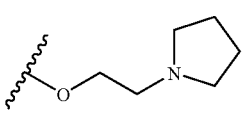 | 4-Fluorophenyl |
| 120 | 1 | CH | CH | N | 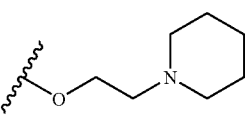 | 3-Fluoro-4-hydroxyphenyl |
| 121 | 1 | CH | CH | N | 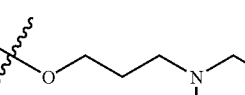 | 4-Fluorophenyl |
| 122 | 1 | CH | CH | N | 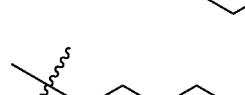 | 4-Fluorophenyl |
| 123 | 1 | CH | CH | N | 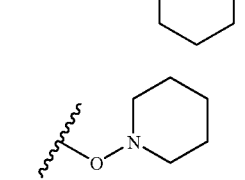 | 4-Fluorophenyl |
| 124 | 1 | CH | CH | N |  | 4-Fluorophenyl |
| 125 | 1 | CH | CH | N |  | 4-Fluorophenyl |
| 126 | 1 | CH | CH | N |  | 4-Fluorophenyl |

TABLE 1-continued
Representative Compounds of Structure (VII)
| Cpd No. | a | A | B | C | R₁ | R₂ |
|---|---|---|---|---|---|---|
| 127 | 1 | CH | CH | N | 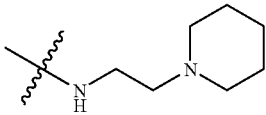 | 4-Fluorophenyl |
| 128 | 1 | CH | CH | N | 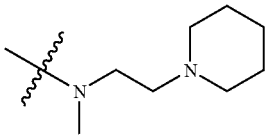 | 4-Fluorophenyl |
| 129 | 1 | CH | CH | N | 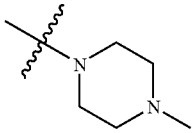 | 4-Fluorophenyl |
| 130 | 1 | CH | CH | N | 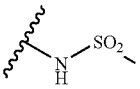 | 4-Fluorophenyl |
| 131 | 1 | CH | CH | N | 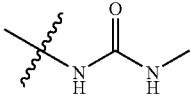 | 4-Fluorophenyl |
| 132 | 1 | CH | CH | N | 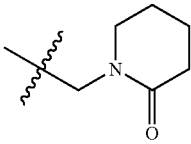 | 4-Fluorophenyl |
| 133 | 1 | CH | CH | N |  | 4-Fluorophenyl |
| 134 | 1 | CH | CH | N | 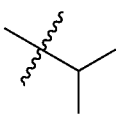 | 4-Fluorophenyl |
| 135 | 1 | CH | CH | N | 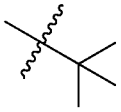 | 4-Fluorophenyl |
| 136 | 1 | CH | CH | N | 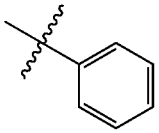 | 4-Fluorophenyl |
| 137 | 1 | CH | CH | N | 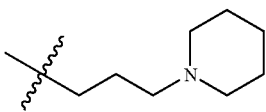 | 4-Fluorophenyl |

TABLE 1-continued

Representative Compounds of Structure (VII)

| Cpd No. | a | A | B | C | R₁ | R₂ |
|---|---|---|---|---|---|---|
| 138 | 1 | CH | CH | N | propyl-piperidinyl | 4-Fluorophenyl |
| 139 | 1 | CH | CH | N | methyl-piperidinyl | 4-Fluorophenyl |
| 140 | 1 | CH | CH | N | piperidinyl (direct) | 4-Fluorophenyl |

In still a further embodiment, D of structure (I) is carbonyl—that is, $-(CH_2)_nC(=O)(CH_2)_m-$ wherein both n and m are zero—and the compounds of this invention have the following structure (VIII):

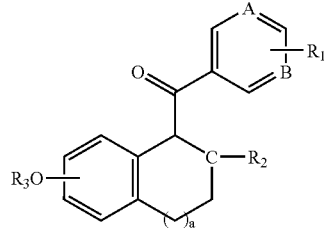

(VIII)

In one aspect of this embodiment, $R_3$ is hydrogen and compounds of this invention have the following structure (VIIIa):

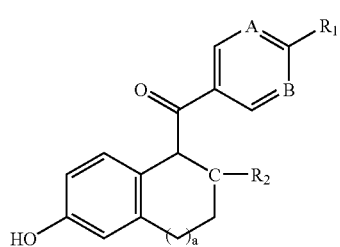

(VIIIa)

For purposes of illustration, representative compounds of structure (VIIIa) are set forth in Table 2.

TABLE 2

Representative Compounds of Structure (VIIIa)

| Cpd. No. | a | A | B | C | R₁ | R₂ |
|---|---|---|---|---|---|---|
| 141 | 1 | CH | CH | N | —O—CH₂CH₂-piperidinyl | Phenyl |
| 142 | 1 | CH | CH | N | —O—CH₂CH₂-piperidinyl | 4-Fluorophenyl |
| 143 | 1 | CH | CH | N | —O—CH₂CH₂-piperidinyl | 2-Methyl-4-fluorophenyl |
| 144 | 1 | CH | CH | N | —O—CH₂CH₂-piperidinyl | 2-Methoxypyridin-5-yl |
| 145 | 1 | CH | CH | N | —O—CH₂CH₂-piperidinyl | Pyrimidin-5-yl |

TABLE 2-continued

Representative Compounds of Structure (VIIIa)

| Cpd. No. | a | A | B | C | R₁ | R₂ |
|---|---|---|---|---|---|---|
| 146 | 1 | CH | CH | N |  | 4-Fluorophenyl |
| 147 | 1 | CH | CH | N |  | 4-Fluorophenyl |
| 148 | 1 | CH | CH | N |  | 4-Fluorophenyl |
| 149 | 1 | CH | CH | N | 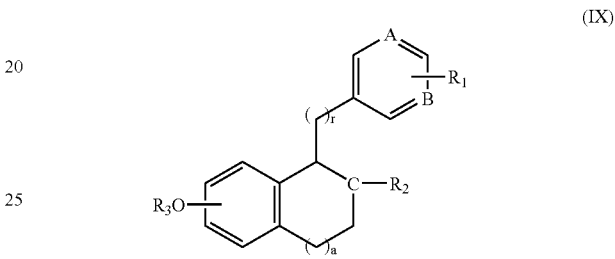 | 4-Fluorophenyl |
| 150 | 1 | CH | CH | N | 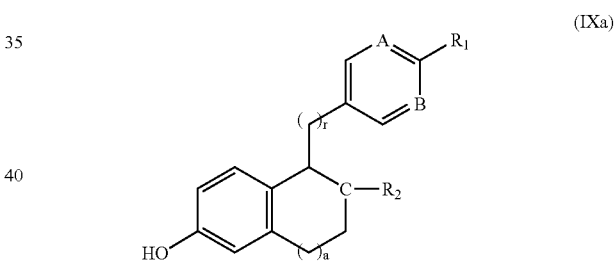 | 4-Fluorophenyl |
| 151 | 1 | N | CH | N |  | 4-Fluorophenyl |
| 152 | 1 | N | N | N |  | 4-Fluorophenyl |

In yet a further embodiment, D of structure (I) is —(CH₂)$_r$— and the compounds of this invention have the following structure (IX):

$$\text{(IX)}$$

In one aspect of this embodiment, R₃ is hydrogen and compounds of this invention have the following structure (IXa):

$$\text{(IXa)}$$

For purposes of illustration, representative compounds of structure (IXa) are set forth in Table 3.

TABLE 3

Representative Compounds of Structure (IXa)

| Cpd. No. | a | A | B | C | r | R₁ | R₂ |
|---|---|---|---|---|---|---|---|
| 153 | 1 | CH | CH | N | 2 | | 4-Fluorophenyl |
| 154 | 1 | CH | CH | N | 2 | | 2-Thienyl |

TABLE 3-continued

Representative Compounds of Structure (IXa)

| Cpd. No. | a | A | B | C | r | R₁ | R₂ |
|---|---|---|---|---|---|---|---|
| 155 | 1 | CH | CH | N | 2 | 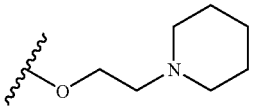 | 2-Methyl-4-fluorophenyl |
| 156 | 1 | CH | CH | N | 2 | Hydrogen | Phenyl |
| 157 | 1 | CH | CH | N | 3 | 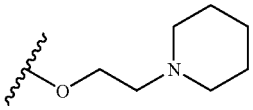 | 4-Fluorophenyl |
| 158 | 1 | CH | CH | N | 3 | —OCH₃ | 4-Fluorophenyl |
| 159 |   | CH | CH | N | 4 | —F | 4-Fluorophenyl |
| 160 |   | CH | CH | N | 4 | 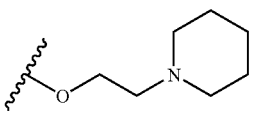 | 4-Fluorophenyl |
| 161 |   | CH | CH | N | 5 | Hydrogen | 4-Fluorophenyl |
| 162 |   | CH | CH | N | 5 | 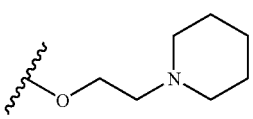 | 4-Fluorophenyl |

As noted above, compounds of this invention have structure (I), wherein a is 1, 2 or 3, yielding a fused, bicyclic six-five-, six-six- or six-seven-membered ring system. In a typical embodiment, a is 1.

With regard to the A and B moieties, in a typical embodiment both A and B are CH, yielding a benzene ring substituted with the $R_1$ moiety. Other representative groups in this regard include those embodiments wherein either A or B is nitrogen, or wherein both A and B are nitrogen.

Representative C moieties include both nitrogen and CH. In a typical embodiment, the C moiety is nitrogen.

D moieties of this invention include —(CH$_2$)$_r$— and —(CH$_2$)$_n$C(=O)(CH$_2$)$_m$—. When D is —(CH$_2$)$_r$—, r is typically 1 or 2, and more typically 1—such that D moiety is methylene. In the embodiment wherein D is —(CH$_2$)$_n$C(=O)(CH$_2$)$_m$—, n and m are typically 0, 1 or 2. In one embodiment, both n and m are zero, and D is carbonyl.

$R_1$ groups of this invention have the formula —X—Y. As used herein, $R_1$ designates either one or two $R_1$ substuents. In the case of two $R_1$ substituents, each of the $R_1$ substituents may be the same or different. Typically, $R_1$ refers to a single substituent as represented by —X—Y.

In one embodiment, X is —(CH$_2$)$_n$Z(CH$_2$)$_m$— and Y has the following structure:

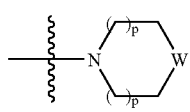

Representative $R_1$ groups in this regard include those wherein n is zero and Z is oxygen, and having the following structure:

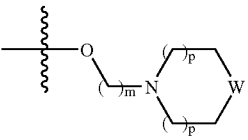

For example, when W is oxygen, p and q are both 1, representative $R_1$ groups include the following (wherein m is, for example, 2 or 3):

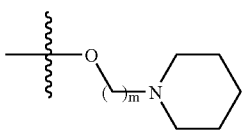

Other embodiments in this regard include those wherein Y is —NR$_e$R$_f$, and having the following structure:

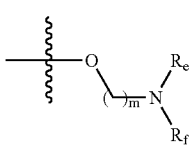

Further embodiments of $R_1$ include the following structures:

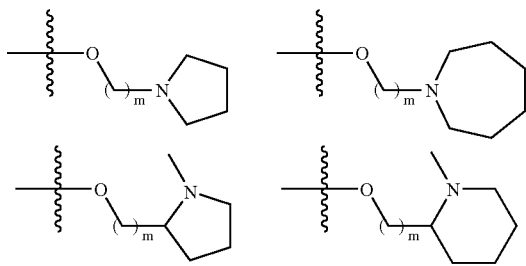

Representative $R_1$ groups also include those having the following structure:

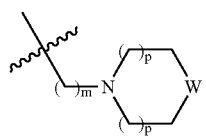

In a further embodiment, $R_1$ is hydrogen, halogen (such as fluorine, bromine or chloribne) or hydroxyl. This embodiment results in compounds of the present invention being highly selective for ER-β over ER-α, particularly when $R_1$ is halogen or hydroxy. Further representative $R_1$ groups include those set forth below in Examples 1-139.

Representative $R_2$ groups include substituted or unsubstitued $C_{6-12}$aryl, and typically substituted phenyl. In one embodiment, $R_2$ is phenyl substituted with one or two substituents selected from halogen, such as fluorine Again, further representative $R_2$ groups include those as set forth below in Examples 1-139.

Representative $R_3$ groups include hydrogen and $C_{1-4}$alkyl, and $R_3$ is typically hydrogen or methyl.

The compounds of this invention may be made by the procedures and techniques disclosed in the Examples, as well as by known organic synthesis techniques, including the techniques disclosed in published PCT WO 96/21656 (which reference is incorporated herein in its entirety) but utilizing the corresponding benzyl starting materials rather than the phenyl compounds. For example, the compounds of this invention may be made by the following general reaction schemes.

Reaction Scheme 1:

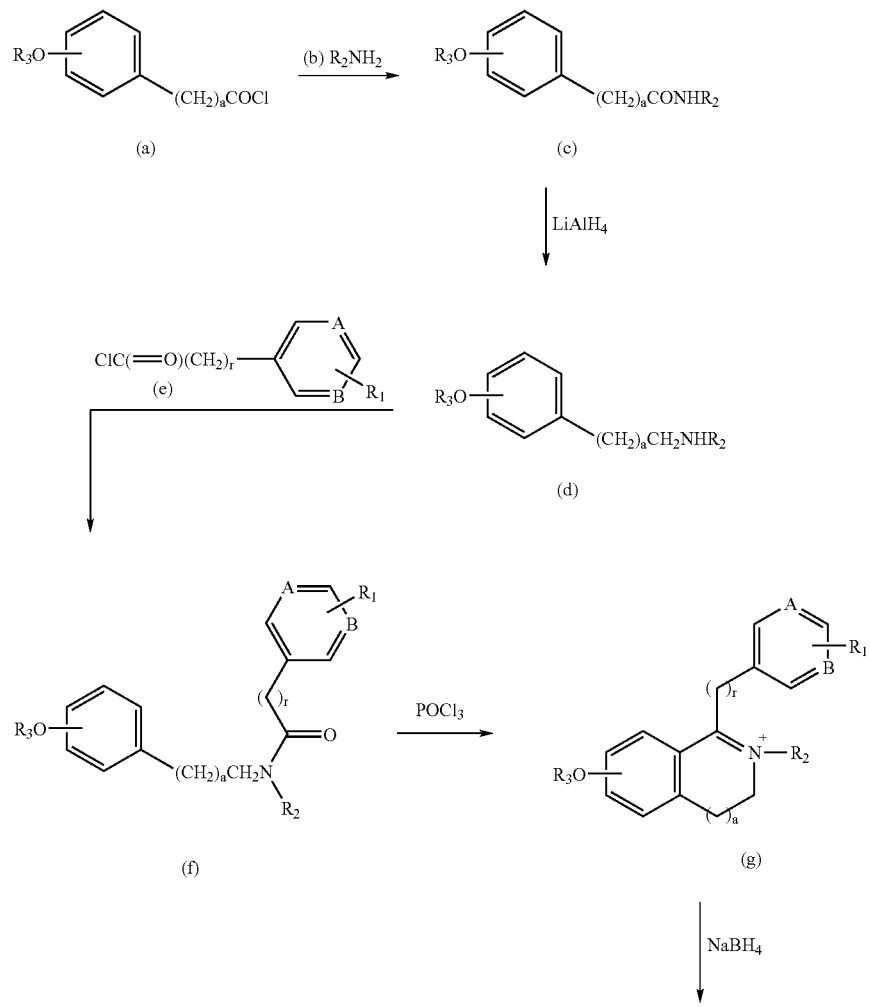

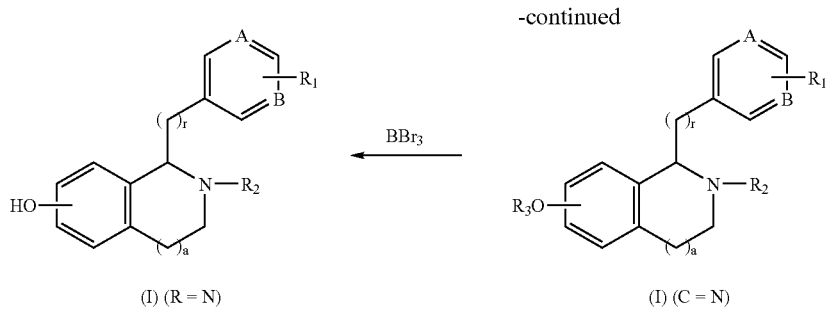

In the above Reaction Scheme 1, aryl acid chloride (a), on treatment with primary amine (b) affords aryl secondary amide (c), which is reduced with lithium aluminum hydride in ethereal solvents to yield secondary amine (d). Subsequent acylation of (d) with acid chloride (e) leads to tertiary amide (f), which is cyclized in hot phosphorus oxychloride to yield dihydroisoquinolinium salt (g). Reduction of (g) with sodium borohydride yields compounds of structure (I) where C is N, which upon demethylation with boron tribromide in methylene chloride affords compounds of structure (I) where $R_3$ is hydrogen.

Reaction Scheme 2:

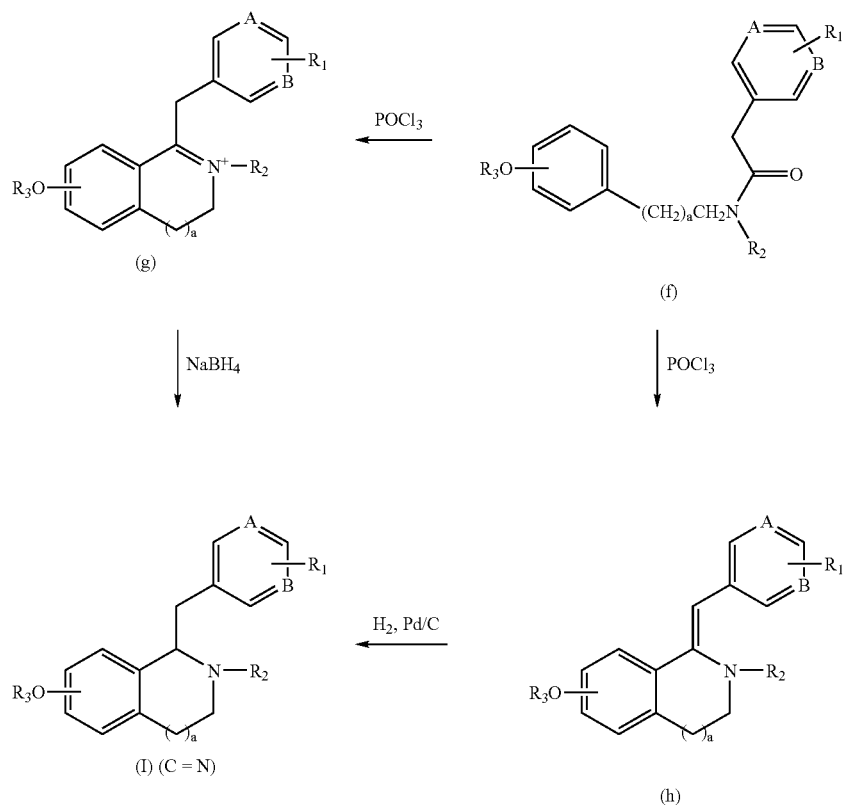

In Reaction Scheme 2, tertiary amide (f) as prepared in Reaction Scheme 1 is cyclized upon heating in phosphorous oxychloride. The cyclized product—that is, the imine salt (g) or the enamine (h)—is $R_2$ dependent. Reduction of (g) with sodium borohydride or reduction of (h) with hydrogen and palladium on carbon affords compounds of structure (I).

Reaction Scheme 3:

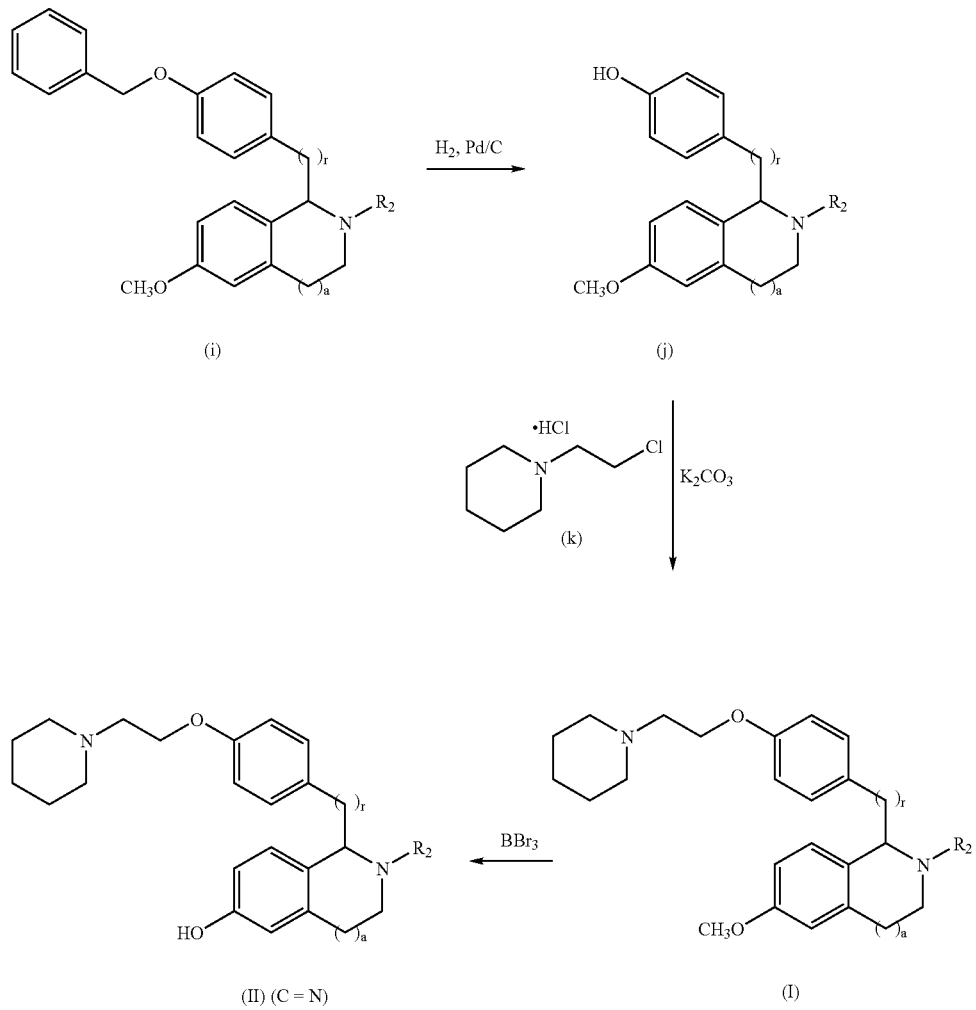

In Reaction Scheme 3, debenzylation of (i) using hydrogen and palladium on carbon provides the hydroxybenzyltetrahydroisoquinoline (j). Alkylation with 2-chloroethyl-peperidinehydrochloride using potassium carbonate yields (I), which is the demethylated using boron tribromide to provide compounds of structure (II).

Reaction Scheme 4:

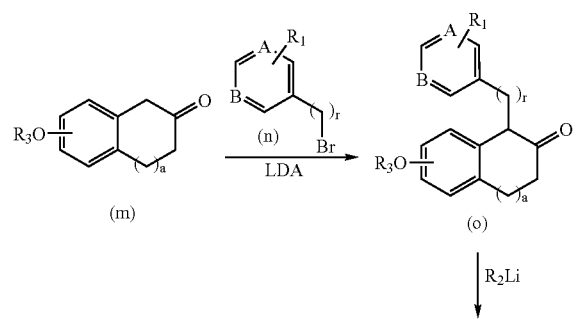

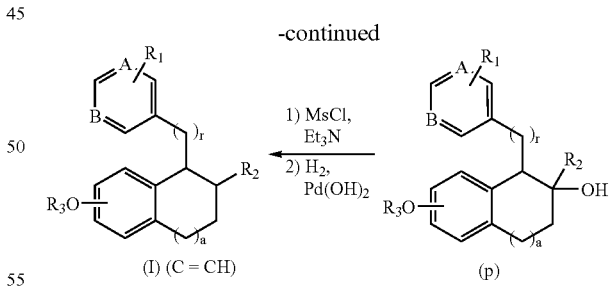

The above Reaction Scheme 4 illustrates the synthesis of compounds of structure (I) wherein C is CH. In this scheme, tetralone (m) is deprotonated with a base, such as LDA, and alkylated with a benzylbromide (n)—or a corresponding heterocylic compound when A and B are other than CH—to yield the adduct (p). Treatment of (p) with mesylchloride and triethylamine followed by treatment with hydrogen and palladium hydroxide (or palladium on carbon) affords compounds of structure (I) wherein C is CH.

Reaction Scheme 5:
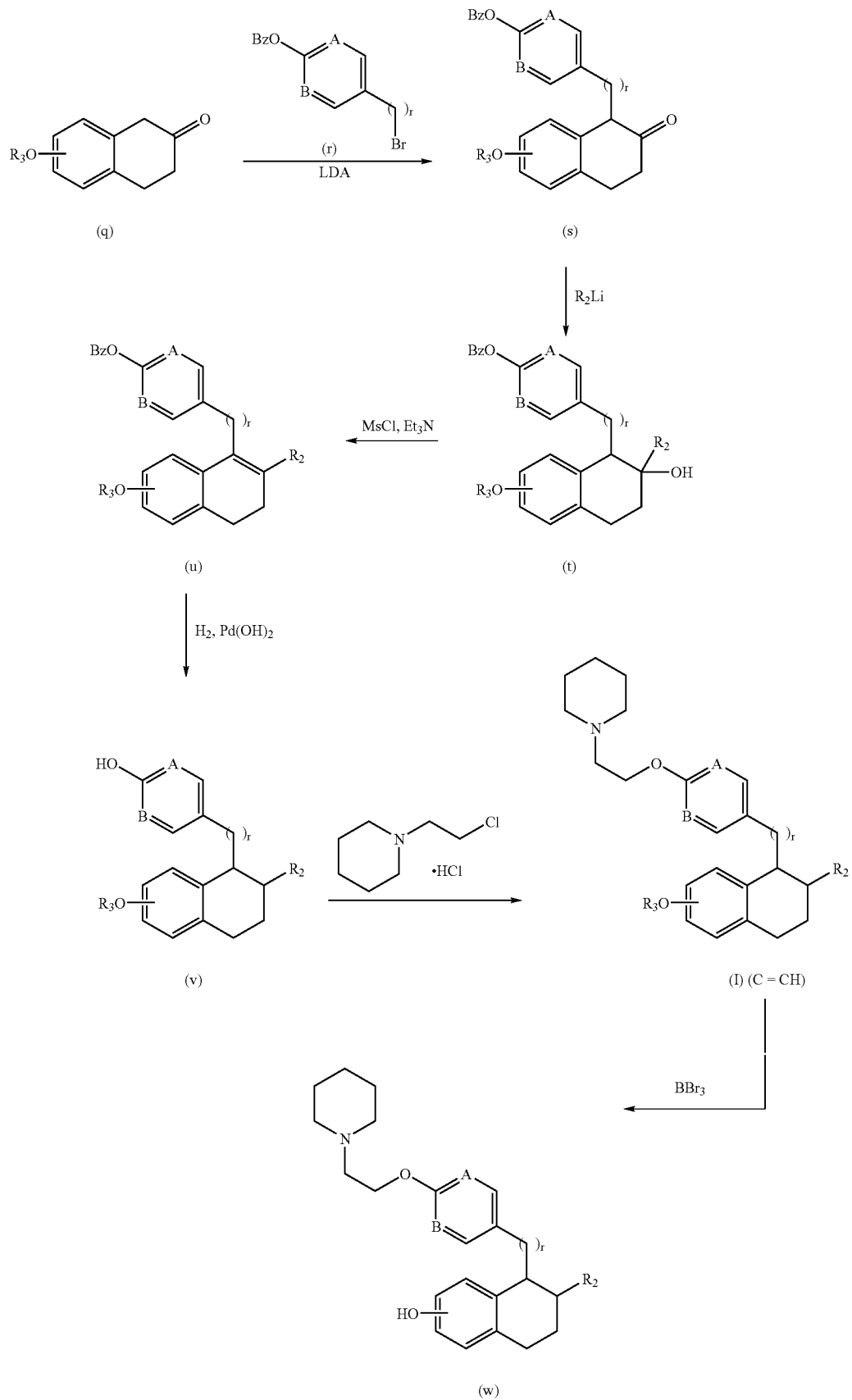

In Reaction Scheme 5, compounds of structure (I) where C is CH may be made according to the above reaction scheme. Alkyloxy tetralone (q) is deprotonated with a base, such as LDA, and alkylated with a benzylbromide (r) to yield the benzyl adduct (s). Treatment of (s) with an organolithium provides the hydroxy intermediate (t), which is then reacted with mesylchloride and triethylamine to afford the dehydrated product (u). Reduction and debenzylation of (u) using hydrogen and palladium hydroxide on carbon affords (v). Subsequent alkylation using 2-chloroethylpiperidine hydrochloride and base yields compounds of structure (I) where C=CH, which can be converted to the corresponding hydroxyl (w) by dealkylation using boron tribromide. (w)

Reaction Scheme 6:

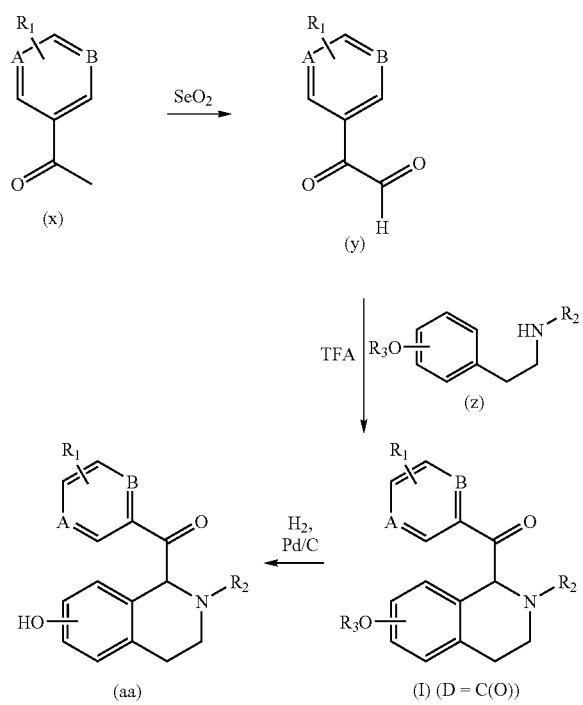

In Reaction Scheme 6, compounds of structure (I) where D is carbonyl may be made according to the above reaction scheme. Ketone (x) is oxidized with selenium dioxide to yield the glyoxal (y). Treatment of (y) with secondary amine (z) and trifluoroacetic acid provides compounds of structure (I) wherein D is carbonyl, which can be converted to the corresponding hydroxyl (aa) by debenzylation using hydrogen and palladium on carbon.

Reaction Scheme 7:

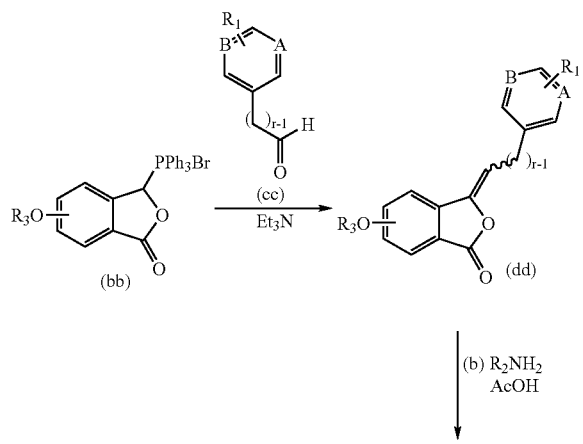

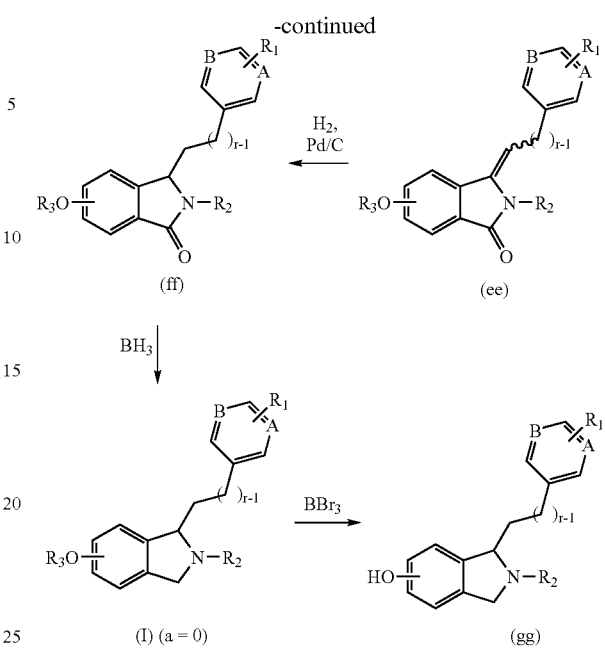

The above Reaction Scheme 7 illustrates the synthesis of compounds of structure (I) wherein a is 0. The dihydroisobenzofuran (bb) is prepared as described by Sakamoto et al. (*Chem. Pharm. Bull.* 31, 2698-2707, 1983). Treatment of (bb) with aldehyde (cc) provides the adduct (dd), which upon reaction with primary amine (b) yields the isoindolinone (ce). The double bond of (cc) is reduced using hydrogen and palladium on carbon to yield the corresponding isoindolinone (ff). Subsequent reduction of the carbonyl of (ff) with borane provides compounds of structure (I) where a=0, which can be converted to the corresponding hydroxyl (gg) upon treatment with boron tribromide.

One of ordinary skill in this field will recognize that certain compounds of this invention will contain atoms which may be in a particular optical or geometric configuration. Likewise, one will recognize that various pharmaceutically acceptable esters and salts may be prepared from certain compounds of this invention. All of such stereoisomers, esters and salts are included in this invention.

The methods for treating estrogen-related conditions of this invention—such as breast cancer, osteoporosis, endometriosis, cardiovascular disease, hypercholesterolemia, prostatic hypertrophy, prostate cancer, obesity, hot flashes, skin effects, mood swings, memory loss, menopausal syndromes, type-II diabetes, Alzheimer's disease, urinary incontinence, GI tract conditions, spermatogenesis, vascular protection after injury, endometriosis, learning and memory, CNS effects, plasma lipid levels, acne, hirsutism, other solid cancers (such as colon, lung, ovarian, testis, melanoma, CNS, and renal), multiple myeloma, lymphoma, and adverse reproductive effects associated with exposure to environmental chemicals—include administration of an effective amount of a compound of structure (I), or a salt or ester thereof, as the active ingredient. Pharmaceutically acceptable salts of the compounds of structure (I) are typically salts of non-toxic type commonly used, such as salts with organic acids (e.g., formic, acetic, trifluoroacetic, citric, maleic, tartaric, methanesulfonic, benzenesulfonic or toluenesulfonic acids), inorganic acids (e.g., hydrochloric, hydrobromic, sulfuric or phosphoric acids), and amino acids (e.g., aspartic or glutamic acids). These salts may be prepared by the methods known to chemists of ordinary skill.

The compounds of this invention may be administered to animals (including humans) orally or parenterally in the conventional form of preparations, such as capsules, microcapsules, tablets, granules, powder, troches, pills, suppositories, injections, suspensions and syrups. Suitable formulations may be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The amount of the active ingredient in the medical composition may be at a level that will exercise the desired therapeutical effect; for example, about 0.1 mg to 100 mg in unit dosage for both oral and parenteral administration.

The active ingredient may be usually administered one to four times a day with a unit dosage of 0.1 mg to 100 or 200 mg in human patients, but the above dosage may be properly varied depending on the age, body weight and medical condition of the patient and the type of administration. A preferred dose is 0.25 mg to about 60 mg in human patients. One dose per day is preferred.

The compounds of this invention have utility as estrogen agonists and antagonists, as well as pharmaceutical agents or intermediates thereto. Those which are estrogen agonists are useful for oral contraception; relief for the symptoms of menopause; prevention of threatened or habitual abortion; relief of dysmenorrhea; relief of dysfunctional uterine bleeding; relief of endometriosis; an aid in ovarian development; treatment of acne; diminution of excessive growth of body hair in women (hirsutism); the prevention and treatment of cardiovascular disease; prevention and treatment of atherosclerosis; prevention and treatment of osteoporosis; treatment of benign prostatic hyperplasia and prostatic carcinoma obesity; and suppression of post-partum lactation. These agents also have a beneficial effect on plasma lipid levels and as such are useful in treating and preventing hypercholesterolemia. Those which are estrogen antagonists are useful as antiestrogens in, for example, breast and ovarian tissue and thus are useful in the treatment and prevention of breast and ovarian cancer.

Pharmaceutical chemists will easily recognize that physiologically active compounds which have accessible hydroxy groups are frequently administered in the form of pharmaceutically acceptable esters. The literature concerning such compounds, such as estradiol, provides a great number of instances of such esters. The compounds of this invention are no exception in this respect, and can be effectively administered as an ester, formed on the hydroxy groups, just as one skilled in pharmaceutical chemistry would expect. It is believed that esters are metabolically cleaved in the body, and that the actual drug, which such form is administered, is the hydroxy compound itself. It is possible, as has long been known in pharmaceutical chemistry, to adjust the rate or duration of action of the compound by appropriate choices of ester groups.

The pharmaceutically acceptable acid addition salts of the compounds of this invention may be formed of the compound itself, or of any of its esters, and include the pharmaceutically acceptable salts which are often used in pharmaceutical chemistry. For example, salts may be formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, trifluoroacetate salt, acetic acid and propionic acid. It is usually preferred to administer a compound of this invention in the form of an acid addition salt, as it is customary in the administration of pharmaceuticals bearing a basic group such as the pyrrolidino ring.

The compounds of this invention, as discussed above, are very often administered in the form of acid addition salts. The salts are conveniently formed, as is usual in organic chemistry, by reacting the compound of this invention with a suitable acid, such as have been described above. The salts are quickly formed in high yields at moderate temperatures, and often are prepared by merely isolating the compound from a suitable acidic wash in the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A typical technique for preparing hydrochlorides is to dissolve the free base in a suitable solvent and dry the solution thoroughly, as over molecular sieves, before bubbling hydrogen chloride gas through it.

The dose of a compound of this invention to be administered to a human is rather widely variable and subject to the judgment of the attending physician. It should be noted that it may be necessary to adjust the dose of a compound when it is administered in the form of a salt, such as a laureate, the salt forming moiety of which has an appreciable molecular weight. The general range of effective administration rates of the compounds is from about 0.05 mg/day to about 200 mg/day. A preferred rate range is from about 0.25 mg/day to 60 mg/day. Of course, it is often practical to administer the daily dose of compound in portions, at various hours of the day. However, in any given case, the amount of compound administered will depend on such factors as the solubility of the active component, the formulation used and the route of administration.

The route of administration of the compounds of this invention is not critical. The compounds are known to be absorbed from the alimentary tract, and so it is usually preferred to administer a compound orally for reasons of convenience. However, the compounds may equally effectively be administered percutaneously, or as suppositories for absorption by the rectum, if desired in a given instance.

The compounds of this invention are usually administered as pharmaceutical compositions which are important and novel embodiments of the invention because of the presence of the compounds. All of the usual types of compositions may be used, including tablets, chewable tablets, capsules, solutions, parenteral solutions, troches, suppositories and suspensions. Compositions are formulated to contain a daily dose, or a convenient fraction of daily dose, in a dosage unit, which may be a single tablet or capsule or convenient volume of a liquid.

Any of the compounds may be readily formulated as tablets, capsules and the like; it is preferable to prepare solutions from water-soluble salts, such as the hydrochloride salt. In general, all of the compositions are prepared according to methods usual in pharmaceutical chemistry. Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is typically necessary in a tablet formulation to prevent the tablet and punches from sticking in the die. The lubricant is chosen from such slippery solids as talc, magnesium and calcium stearate, stearic acid and hydrogenated vegetable oils. Tablet disintegrators are substances which swell when- wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, may be used as well as sodium lauryl sulfate. Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

The following examples are offered by way of illustration, not limitation.

EXAMPLES

Example 1

SYNTHESIS OF 1-(4-BROMOBENZYL)-6-METHOXY-2-PHENYL-1,2,3,4TETRAHYDROISOQUINOLINE

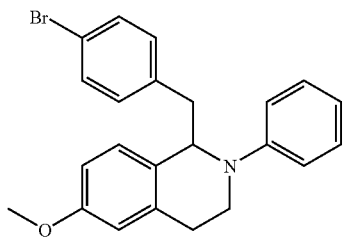

A. 2-(3-Methoxyphenyl)-N-phenylacetamide

To a solution of 3-methoxyphenylacetyl chloride (2.3 g, 12.5 mmol) in ethyl acetate (30 mL) was added a solution of aniline (1.16 g, 12.5 mmol) in ethyl acetate (30 mL). After 3 hours, the reaction was poured into water (50 mL). The organic layer was separated, dried over $MgSO_4$, filtered and concentrated to provide the title compound (2.67 g, 89% yield): EI-MS (m/z) 241.

B. {2-(3-Methoxyphenyl)ethyl}phenylamine

To a solution of 2-(3-methoxyphenyl)-N-phenylacetamide (2.0 g, 8.3 mmol) in anhydrous tetrahydrofuran (30 mL) under nitrogen was added lithium aluminum hydride (1.59 g, 42 mmol) in small portions over a 1 hour period. After 16 hours, the reaction was poured over ice and the crude product extracted with ethyl acetate (2×100 mL). The organic layer was dried over $MgSO_4$, filtered and concentrated to provide the title compound (1.3 g, 69% yield): EI-MS (m/z) 227.

C. 2-(4-Bromophenyl)-N-{2-(3-methoxyphenyl)ethyl}-N-phenylacetamide

To a solution of {2-(3-methoxyphenyl)ethyl}phenylamine (1.06 g, 4.65 mmol) in ethyl acetate (80 mL) under nitrogen was added a solution of 4-bromophenylacetyl chloride (1.06 g, 4.65 mmol) in ethyl acetate (20 mL), the bromophenylacetyl chloride being prepared from the corresponding carboxylic acid (1 g, 4.65 mmol) and oxalyl chloride (0.61 mL, 6.98 mmol) in $CH_2Cl_2$ (20 mL). After 1 hour, the reaction was poured into water (50 mL). The organic layer was dried over $MgSO_4$, filtered and concentrated to provide the title compound (1.92 g, 98% yield): EI-MS (m/z) 423.

D. 1-(4-Bromobenzyl)-6-methoxy-2-phenyl-1,2,3,4-tetrahydroisoquinoline

A solution of 2-(4-bromophenyl)-N-{2-(3-methoxyphenyl)ethyl}-N-phenylacetamide (1.0 g, 2.4 mmol) in phosphorous oxychloride (10 mL) under nitrogen was heated to 80° C. After 15 hours, the reaction was cooled to RT and slowly poured over ice. Potassium iodide (0.78 g, 4.7 mmol) was then added to the mixture, and after 30 minutes, the quinolinium salt was extracted with ethyl acetate (2×100 mL). The organic layer was dried over $MgSO_4$, filtered and concentrated. The residue was then dissolved in methanol (25 mL), and sodium borohydride (0.27 g, 7.2 mmol) was slowly added. After 30 minutes, the reaction was concentrated and partitioned between ethyl acetate and water. The organic layer was dried over MgSO$_4$, filtered and concentrated to provide the title compound (0.20 g, 21% yield): $^1$H NMR (CDCl$_3$) 6.6-7.4 (m, 12H), 4.82 (t, 1H), 3.60 (s, 3H), 3.58 (m, 2H), 2.6-3.2 (m 4H); EI-MS (m/z) 407.

Example 2

SYNTHESIS OF 1-(4-BROMOBENZYL)-2PHENYL-1,2,3,4-TETRAHYDROISOQUINOLIN-6-OL

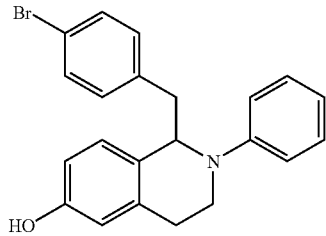

To a solution of 1-(4-bromobenzyl)-6-methoxy-2-phenyl-1,2,3,4-tetrahydroisoquinoline (0.10 g, 0.25 mmol) in CH$_2$Cl$_2$ (15 mL) at 0° C. under nitrogen was added boron tribromide (1.47 mL, 1.47 mmol). The reaction was allowed to reach RT. After 8 hours, the reaction was poured into water (10 mL) and neutralized with saturated sodium bicarbonate. Additional CH$_2$Cl$_2$ (25 mL) was added, the organic layer was separated, dried over MgSO$_4$, filtered and concentrated. The residue was then chromatographed (SiO$_2$, 2:1, hexanes/ethyl acetate) to provide the title compound (0.010 g, 10% yield): $^1$H NMR (CDCl$_3$) 7.33 (d, 2H), 7.24 (dd, 2H), 6.97 (d, 1H), 6.88 (d, 2H), 6.80 (d, 2H), 6.75 (dd, 2H), 6.66 (m, 1H), 6.27 (s, 1H), 4.78 (t, 1H), 3.53 (m 2H), 3.13 (dd, 1H), 2.96 (m, 2H), 2.62 (m, 1H); ES-MS (m/z) 392 [M–H]$^-$.

Example 3

SYNTHESIS OF 2-PHENYL-1-{4-[(2-PIPERIDYL)ETHOXY]BENZYL}-1,2,3,4-TETRAHYDROISOQUINOLIN-6-OL

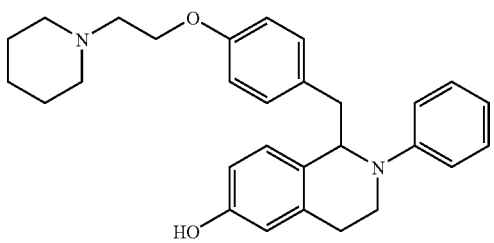

A. N-{2-(3-Methoxyphenyl)ethyl}-N-phenyl-2-{4-(phenylmethoxy)phenyl}acetamide

The title compound was prepared as described in Example 1.C, using 4-benzyloxyphenylacetyl chloride (2.28 g, 8.27 mmol) prepared from the corresponding carboxylic acid (2.0 g, 8.27 mmol) and oxalyl chloride (5.25 mL, 41.4 mmol) in CH$_2$Cl$_2$ (50 mL) (3.36 g, 90% yield): ES-MS (m/z) 452 [M+H]$^+$.

B. 1-{4-(Phenylmethoxy)benzyl}-6-methoxy-2-phenyl-1,2,3,4-tetrahydroisoquinoline The title compound was prepared as described in Example 1.D, using N-{2-(3-methoxyphenyl)ethyl}-N-phenyl-2-{4-(phenylmethoxy)phenyl}acetamide (0.5 g, 1.11 mmol) to afford the title compound (0.19 g, 39% yield): ES-MS (m/z) 436 [M+H]$^+$.

C. 1-(4-Hydroxybenzyl)-6-methoxy-2-phenyl-1,2,3,4-tetrahydroisoquinoline

A solution of 1-{4-(phenylmethoxy)benzyl}-6-methoxy-2-phenyl-1,2,3,4-tetrahydroisoquinoline (0.60 g, 1.38 mmol), palladium (5% wt. oil activated carbon, 0.06 g), and glacial acetic acid (3 drops) in ethanol (30 mL) was stirred under hydrogen for 15 hours. The reaction was filtered and concentrated to provide the title compound (0.30 g, 63% yield): ES-MS (m/z) 346 [M+H]$^+$.

D. 6-Methoxy-2-phenyl-1-{4-[(2-piperidyl)ethoxy]benzyl}-1,2,3,4-tetrahydroisoquinoline A solution of 1-(4-hydroxybenzyl)-6-methoxy-2-phenyl-1,2,3,4-tetrahydroisoquinoline (0.30 g, 0.87 mmol), 2-chloroethylpiperidine hydrochloride (0.32 g, 1.74 mmol) and potassium carbonate (0.24 g, 1.74 mmol) in dimethyl formamide (15 mL) was heated to 80° C. After 6 hours, the mixture was cooled to RT, poured into water (30 mL), and neutralized using a saturated solution of ammonium chloride. The product was extracted with ethyl acetate (2×75 mL), dried over MgSO$_4$, filtered and concentrated. The residue was then chromatographed (SiO$_2$, 10:1 ethyl acetate/ethanol) to provide the title compound (0.20 g, 47% yield): ES-MS (m/z) 457 [M+H]$^+$.

E. 2-Phenyl-1-{4-[(2-piperidyl)ethoxy]benzyl}-1,2,3,4-tetrahydroisoquinoline-6-ol The title compound was prepared as described in Example 2, using 6-methoxy-2-phenyl-1-{4-[(2-piperidyl)ethoxy]benzyl}-1,2,3,4-tetrahydro-isoquinoline (0.08 g, 0.16 mmol) to afford 6-hydroxy-2-phenyl-1-{4-[(2-piperidyl)ethoxy]benzyl}-1,2,3,4-tetrahydroisoquinoline (0.030 g, 42% yield): $^1$H NMR (CD$_3$OD) 7.13 (dd, 2H), 7.03 (d, 2H), 6.94 (d, 2H), 6.91 (dd, 4H), 6.64 (m, 2H), 4.78 (t, 1H), 4.29 (m, 2H), 3.3-36 (m, 6H), 3.11 (dd, 1H), 3.00 (dd, 1H), 2.80 (m, 1H), 2.57 (m, 1H), 1.84 (m, 6H), 1.15 (t, 2H); ES-MS (m/z) 443 [M+H]$^+$.

Example 4

SYNTHESIS OF 2-(4-FLUOROPHENYL)-6-METHOXY-1-{4-[(2-PIPERIDYL)ETHOXY]BENZYL}-1,2,3,4-TETRAHYDROISOQUINOLINE

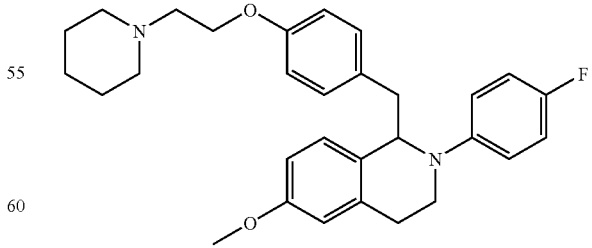

A. N-(4-Fluorophenyl)-2-(3-methoxyphenyl)acetamide

The title compound was prepared as described in Example 1.A, using 3-methoxyphenylacetyl chloride (3.29 g, 18.0 mmol) and 4-fluoroaniline (1.98 g, 18.0 mmol) to afford the title compound (4.57 g, 98% yield): ES-MS (m/z) 259.

B. (4-Fluorophenyl){2-(3-methoxyphenyl)ethyl}amine

The title compound was prepared as described in Example 1.B, using N-(4-fluorophenyl)-2-(3-methoxyphenyl)acetamide (4.57 g, 17.6 mmol). Chromatography (SiO₂, 5:1 hexanes/ethyl acetate) of the crude mixture afforded the title compound (3.84 g, 52% yield): ES-MS (m/z) 245.

C. N-(4-Fluorophenyl)-N-{2-(3-methoxyphenyl)ethyl}-2-{4-(phenylmethoxy)phenyl}acetamide The title compound was prepared as described in Example 1.C, using (4-fluorophenyl){2-(3-methoxyphenyl)ethyl}amine (14.2 g, 58 mmol) and 4-benzyloxyphenylacetyl chloride (15.1 g, 58 mmol) prepared from the corresponding carboxylic acid (14.0 g, 58 mmol) and oxalyl chloride (6.5 mL, 75 mmol) in CH₂Cl₂ (150 mL) (19.1 g, 70% yield): ES-MS (m/z) 470 [M+H]⁺.

D. 2-(4-Fluorophenyl)-6-methoxy-1-{4-(phenylmethoxy)benzyl}-1,2,3,4-tetrahydroisoquinoline A solution of N-(4-fluorophenyl)-N-{2-(3-methoxyphenyl)ethyl}-2-{4-(phenylmethoxy)phenyl}acetamide (6.0 g, 12.8 mmol) in phosphorous oxychloride (130 mL) under nitrogen was heated to 80° C. After 20 hours, the reaction was cooled to RT and very slowly poured over ice with vigorous stirring. Ethyl acetate (500 mL) was then added and the layers were separated. The organic layer was washed with brine, dried over MgSO₄, filtered and concentrated to provide the title compound (4.61 g, 80% yield): ES-MS (m/z) 452 [M+H]⁺.

E. 2-(4-Fluorophenyl)-1-(4-hydroxybenzyl)-6-methoxy-1,2,3,4-tetrahydroisoquinoline The title compound was prepared as described in Example 3.C, using 2-(4-fluorophenyl)-6-methoxy-1-{4-(phenylmethoxy)phenylmethylene}-1,2,3,4-tetrahydroisoquinoline (4.0 g, 8.87 mmol). Chromatography (SiO₂, 2:1 hexanes/ethyl acetate) provided the title compound (1.0 g, 31% yield): ES-MS (m/z) 364 [M+H]⁺.

F. 2-(4-Fluorophenyl)-6-methoxy-1-{4-[(2-piperidyl)ethoxy]benzyl}-1,2,3,4-tetrahydroisoquinolin The title compound was prepared as described in Example 3.D, using 2-(4-fluorophenyl)-1-(4-hydroxybenzyl)-6-methoxy-1,2,3,4-tetrahydroisoquinoline (1.0 g, 2.75 mmol) to provide the title compound (1.28 g, 98% yield): ES-MS (m/z) 475 [M+H]⁺.

Example 5

SYNTHESIS OF 2-(4-FLUOROPHENYL)-1-{4-[(2-PIPERIDYL)ETHOXY]BENZYL}-1,2,3,4-TETRAHYDROISOQUINOLIN-6-OL

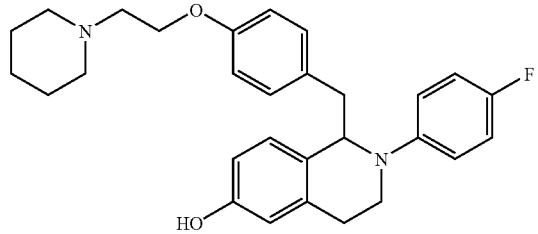

The title compound was prepared as described in Example 3.E, using 2-(4-fluorophenyl)-6-methoxy-1-{4-[(2-piperidyl)ethoxy]benzyl}-1,2,3,4-tetrahydroisoquinoline (1.28 g, 2.7 mmol) to afford the title compound (0.42 g, 34% yield): ¹H NMR (CDCl₃) 6.5-7.0 (m, 11H), 4.68 (t, 1H), 4.07 (m, 2H), 3.4-3.5 (m, 3H), 3.06 (m, 1H), 2.5-2.9 (m, 8H), 1.46 (m, 4H), 1.26 (m, 2H); ES-MS (m/z) 461 [M+H]⁺.

Example 6

SYNTHESIS OF 6-METHOXY-2-{5-(2-METHOXYPYRIDINE)}-1-{4-[(2-PIPERIDYL)ETHOXY]BENZYL}-1,2,3,4-TETRAHYDROISOQUINOLINE

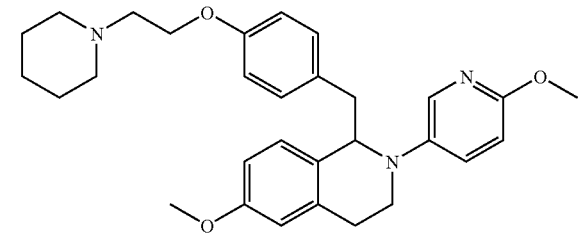

A. 2-(3-Methoxyphenyl)-N-{2-methoxy(5-pyridyl)}acetamide

The title compound was prepared as described in Example 1.A, using 3-methoxyphenylacetyl chloride (4.8 g, 26.0 mmol) and 5-amino-2-methoxypyridine (3.23 g, 26.0 mmol) to afford the title compound (7.0 g, 99% yield): ES-MS (m/z) 272.

B. {2-(3-Methoxyphenyl)ethyl}-N-{2-methoxy(5-pyridyl)}amine

The title compound was prepared as described in Example 1.B, using 2-(3-methoxyphenyl)-N-{2-methoxy(5-pyridyl)}acetamide (7.0 g, 25.7 mmol). Chromatography (SiO₂, 5:1 hexanes/ethyl acetate) afforded the title compound (3.96 g, 60% yield): ES-MS (m/z) 258.

C. N-{2-Methoxy(5-pyridyl)}-N-{2-(3-methoxyphenyl)ethyl}-2-{4-(phenylmethoxy)phenyl}acetamide The title compound was prepared as described in Example 3.A, using {2-(3-methoxyphenyl)ethyl}-N-{2-methoxy(5-pyridyl)}amine (3.3 g, 12.8 mmol) to afford the title compound (5.0 g, 81% yield): ES-MS (m/z) 483 [M+H]$^+$.

D. 1-{4-(Phenylmethoxy)benzyl}-6-methoxy-2-{5-(2-methoxypyridyl)}-1,2,3,4-tetrahydroisoquinoline The title compound was prepared as described in Example 1.D, using N-{2-methoxy(5-pyridyl)}-N-{2-(3-methoxyphenyl)ethyl}-2-{4-(phenylmethoxy)phenyl}acetamide (3.67 g, 7.61 mmol) to provide the title compound (2.7 g, 76% yield): ES-MS (m/z) 467 [M+H]$^+$.

E. 1-(4-Hydroxybenzyl)-6-methoxy-2-{5-(2-methoxypyridyl)}-1,2,3,4-tetrahydroisoquinoline The title compound was prepared as described in Example 3.C, using 1-{4-(phenylmethoxy)benzyl}-6-methoxy-2-{5-(2-methoxypyridyl)}-1,2,3,4-tetrahydroisoquinoline (0.87 g, 1.86 mmol) to afford the title compound (0.63 g, 90% yield): ES-MS (m/z) 377 [M+H]$^+$.

F. 6-Methoxy-2-{5-(2-methoxypyridine)}-1-{4-[(2-piperidyl)ethoxy]benzyl}-1,2,3,4-tetrahydroisoquinoline The title compound was prepared as described in Example 3.D, using 1-(4-hydroxybenzyl)-6-methoxy-2-{5-(2-methoxypyridyl)}-1,2,3,4-tetrahydroisoquinoline (0.60 g, 1.6 mmol) to afford the title compound (0.61 g, 78% yield): ES-MS (m/z) 488 [M+H]$^+$.

Example 7

SYNTHESIS OF 2-{5-(2-METHOXYPYRIDINE)}-1-{4-[(2-PIPERIDYL)ETHOXY]BENZYL}-1,2,3,4-TETRAHYDROISOQUINOLIN-6-OL

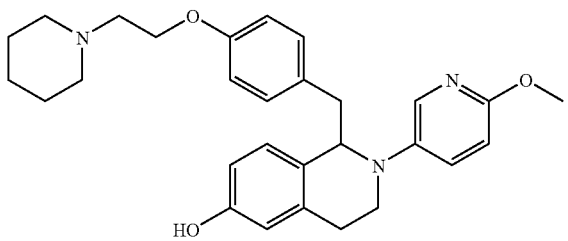

The title compound was prepared as described in Example 2, using 6-methoxy-2-{5-(2-methoxypyridine)}-1-{4-[(2-piperidyl)ethoxy]benzyl}-1,2,3,4-tetrahydroisoquinoline (0.2 g, 0.41 mmol) to afford the title compound (0.017 g, 9% yield): ES-MS (m/z) 474 [M+H]$^+$.

Example 8

SYNTHESIS OF 2-FLUOROPHENYL-1{4-[(2-PIPERIDYL)ETHOXY]BENZYL}-1H, 3H, 4H, 5H-BENZO(E)AZEPIN-7-YL

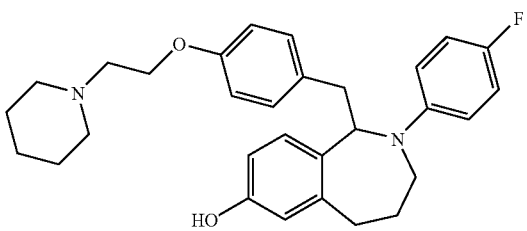

A. N-(4-Fluorophenyl)-3-(3-methoxyphenyl)propanamide

The title compound was prepared as described in Example 1.A, using 3-methoxyphenylpropionylchloride (6.62 g, 33.3 mmol) and 4-fluoroaniline (3.70 g, 33.3 mmol) to afford N-(4-fluorophenyl)-3-(3-methoxyphenyl)propanamide (8.85 g, 97% yield): ES-MS (m/z) 273.

B. (4-Fluorophenyl)[3-(3-methoxyphenyl)propyl]amine

The title compound was prepared as described in Example 1.B, using N-(4-fluorophenyl)-3-(3-methoxyphenyl)propanamide (2.0 g, 7.32 mmol) to afford (4-fluorophenyl)[3-(3-methoxyphenyl)propyl]amine (1.85 g, 97% yield): ES-MS (m/z) 259.

C. N-(4-Fluorophenyl)-2-(4-methoxyphenyl)-N-[3-(3-methoxyphenyl)propyl]acetamide The title compound was prepared as described in Example 1.C, using (4-fluorophenyl)[3-(3-methoxyphenyl)propyl]amine (1.0 g, 4.13 mmol) to afford N-(4-fluorophenyl)-2-(4-methoxyphenyl)-N-[3-(3-methoxyphenyl)propyl]acetamide (1.84 g, 92% yield): ES-MS (m/z) 484 [M+H]$^+$.

D. 2-Fluorophenyl-7-methoxy-1-{4-[(2-piperidyl)ethoxy]benzyl}-1H, 3H, 4H, 5H-benzo(e)azepine The title compound was prepared as described in Example 4.D, using N-(4-fluorophenyl)-2-(4-methoxyphenyl)-N-[3-(3-methoxyphenyl)propyl]acetamide (0.80 g, 1.65 mmol) to afford 1-{[2-(4-fluorophenyl)-7-methoxy(3H,4H,5H-benzo[e]azepinylidene)]methyl}-4-(phenylmethoxy)benzene (0.50 g, 65% yield): ES-MS (m/z) 466 [M+H]$^+$.

E. 2-Fluorophenyl-1-(4-hydroxybenzyl)-1-{4-[(2-piperidyl)ethoxy]benzyl}-1H,3H,4H,5H-benzo(e)azepine The title compound was prepared as described in Example 3.C, using 1-{[2-(4-fluorophenyl)-7-methoxy(3H,4H,5H-benzo[e]azepinylidene)]methyl}-4-(phenylmethoxy)benzene (0.30 g, 0.64 mmol) to afford the title compound (0.168 g, 69% yield): ES-MS (m/z) 378 [M+H]$^+$.

F. 2-Fluorophenyl-7-methoxy-1-{4-[2-piperidyl) ethoxy]benzyl}-1H,3H,4H,5H-benzo[e]azepine The title compound was prepared as described in Example 3.D, using 2-fluorophenyl-1-(4-hydroxybenzyl)-1-{4-[(2-piperidyl)ethoxy]benzyl}-1H, 3H, 4H, 5H-benzo(e)azepine (0.15 g, 0.397 mmol) to afford the title compound (0.164 g, 87% yield): ES-MS 489 (m/z) [M+H]$^+$.

G. 2-fluorophenyl-1 {4-[(2-piperidyl)ethoxy]benzyl}-1H,3H,4H,5H-benzo(e)azepin-7-yl The title compound was prepared as described in Example 3.E, using 2-fluorophenyl-7-methoxy-1-{4-[2-piperidyl)ethoxy]benzyl}-1H,3H,4H,5H-benzo[e]azepine (0.8 g, 0.41 mmol) to afford the title compound (0.033 g, 42% yield): ES-MS (m/z) 475 [M+H]$^+$.

Example 9

SYNTHESIS OF 2-(4-FLUOROPHENYL)-1-{4-[(2-DIETHYLAMINO)ETHOXY]BENZYL}-1,2,3,4-TETRAHYDROISOQUINOLIN-6-OL

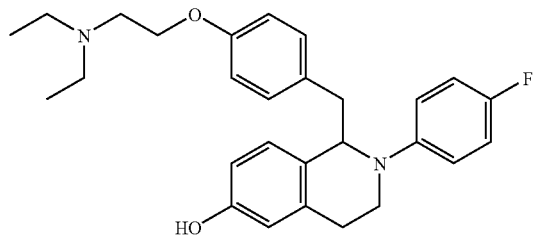

A. 2-(4-Fluorophenyl)-6-methoxy-1-{4-[(2-diethylamino)ethoxy]benzyl}-1,2,3,4-tetrahydroisoquinoline The title compound was prepared as described in Example 3.D. using 2-(4-fluorophenyl)-1-(4-hydroxybenzyl)-6-methoxy-1,2,3,4-tetrahydroisoquinoline (0.13 g, 0.36 mmol) and 2-(diethylamino)ethylchloride hydrochloride (0.074 g, 0.429 mmol) to provide the title compound (0.101 g, 61% yield): ES-MS (m/z) 463 [M+H]$^+$.

B. 2-(4-Fluorophenyl)-1-{4-[(2-diethylamino)ethoxy]benzyl}-1,2,3,4-tetrahydroisoquinolin-6-ol The title compound was prepared as described in Example 2 using 2-(4-fluorophenyl)-6-methoxy-1-{4-[(2-diethylamino)ethoxy]benzyl}-1,2,3,4-tetrahydroisoquinoline (0.101 g, 0.218 mmol) to provide the title compound (0.021 g, 20% yield): ES-MS (m/z) 449 [M+H]$^+$.

Example 10

SYNTHESIS OF 2-(4-FLUOROPHENYL)-1-{4-[(2-DIISOPROPYLAMINO)ETHOXY]BENZYL}-1,2,3,4-TETRAHYDROISOQUINOLIN-6-OL

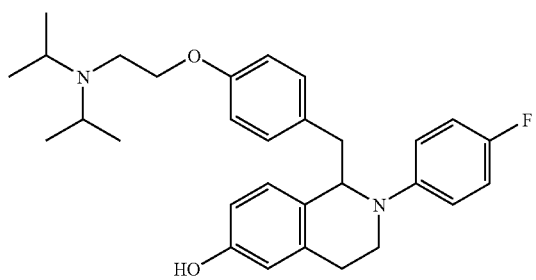

A. 2-(4-Fluorophenyl)-6-methoxy-1-{4-[(2-diisopropylamino)ethoxy]benzyl}-1,2,3,4-tetrahydroisoquinoline The title compound was prepared as described in Example 3.D. using 2-(4-fluorophenyl)-1-(4-hydroxybenzyl)-6-methoxy-1,2,3,4-tetrahydroisoquinoline (0.13 g, 0.36 mmol) and 2-(diisopropylamino)ethylchloride hydrochloride (0.086 g, 0.429 mmol) to provide the title compound (0.091 g, 52% yield): ES-MS (m/z) 491 [M+H]$^+$.

B. 2-(4-Fluorophenyl)-1-{4-[(2-diisopropylamino)ethoxy]benzyl}-1,2,3,4-tetrahydroisoquinolin-6-ol The title compound was prepared as described in Example 2 using 2-(4-fluorophenyl)-6-methoxy-1-{4-[(2-diisopropylamino)ethoxy]benzyl}-1,2,3,4-tetrahydroisoquinoline (0.091 g, 0.185 mmol) to provide the title compound (0.032 g, 36% yield): ES-MS (m/z) 477 [M+H]$^+$.

Example 11

SYNTHESIS OF 2-(4-FLUOROPHENYL)-1-{4-[(2-(1-METHYLPYRROLIDIN-2-YL))ETHOXY]BENZYL}-1,2,3,4-TETRAHYDROISOQUINOLIN-6-OL

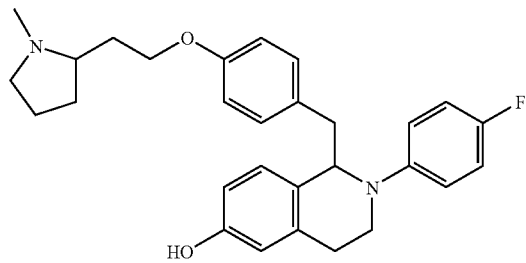

A. 2-(4-Fluorophenyl)-6-methoxy-1-{4-[(2-(1-methylpyrrolidin-2-yl))ethoxy]benzyl}-1,2,3,4-tetrahydroisoquinoline The title compound was prepared as described in Example 3.D. using 2-(4-fluorophenyl)-1-(4-hydroxybenzyl)-6-methoxy-1,2,3,4-tetrahydroisoquinoline (0.13 g, 0.36 mmol) and 2-(2-chloroethyl)-1-methylpyrrolidine hydrochloride (0.079 g, 0.429 mmol) to provide the title compound (0.076 g, 45% yield): ES-MS (m/z) 475 [M+H]+.

B. 2-(4-Fluorophenyl)-1-{4-[(2-(1-methylpyrrolidin-2-yl))ethoxy]benzyl}-1,2,3,4-tetrahydroisoquinolin-6-ol The title compound was prepared as described in Example 2 using 2-(4-fluorophenyl)-6-methoxy-1-{4-[(2-(1-methylpyrrolidin-2-yl))ethoxy]benzyl}-1,2,3,4-tetrahydroisoquinoline (0.076 g, 0.160 mmol) to provide the title compound (0.011 g, 15% yield: ES-MS (m/z) 461 [M+H]+.

Example 12

SYNTHESIS OF 2-(4-FLUOROPHENYL)-1-{4-[(2-PYRROLIDINYL)ETHOXY]BENZYL}-1,2,3,4-TETRAHYDROISOQUINOLIN-6-OL

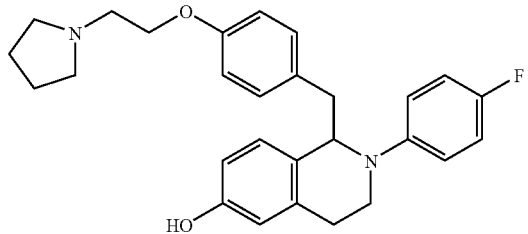

A. 2-(4-Fluorophenyl)-6-methoxy-1-{4-[(2-pyrrolidinyl)ethoxy]benzyl}-1,2,3,4-tetrahydroisoquinoline The title compound was prepared as described in Example 3.D. using 2-(4-fluorophenyl)-1-(4-hydroxybenzyl)-6-methoxy-1,2,3,4-tetrahydroisoquinoline (0.13 g, 0.36 mmol) and 1-(2-chloroethyl)pyrrolidine hydrochloride (0.073 g, 0.429 mmol) to provide the title compound (0.109 g, 66% yield): ES-MS (m/z) 461 [M+H]+.

B. 2-(4-Fluorophenyl)-1-{4-[(2-pyrrolidinyl)ethoxy]benzyl}-1,2,3,4-tetrahydroisoquinolin-6-ol The title compound was prepared as described in Example 2 using 2-(4-fluorophenyl)-6-methoxy-1-{4-[(2-pyrrolidinyl)ethoxy]benzyl}-1,2,3,4-tetrahydroisoquinoline (0.109 g, 0.237 mmol) to provide the title compound (0.036 g, 34% yield): ES-MS (m/z) 447 [M+H]+.

Example 13

SYNTHESIS OF 1-{4-[(2-AZAPERHYDROEPINYL)ETHOXY]BENZYL}-2-(4-FLUOROPHENYL)-1,2,3,4-TETRAHYDROISOQUINOLIN-6-OL

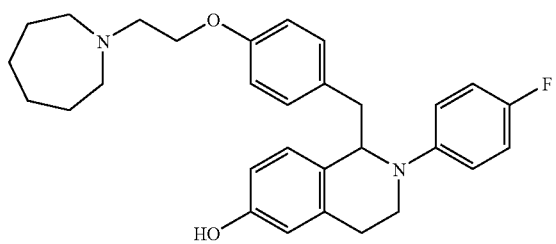

A. 1-{4-[(2-Azaperhydroepinyl)ethoxy]benzyl}-2-(4-fluorophenyl)-6-methoxy-1,2,3,4-tetrahydroisoquinoline The title compound was prepared as described in Example 3.D. using 2-(4-fluorophenyl)-1-(4-hydroxybenzyl)-6-methoxy-1,2,3,4-tetrahydroisoquinoline (0.13 g, 0.36 mmol) and 2-(hexamethylimino)ethylchloride hydrochloride (0.085 g, 0.429 mmol) to provide the title compound (0.105 g, 60% yield): ES-MS (m/z) 489 [M+H]+.

B. 1-{4-[(2-Azaperhydroepinyl)ethoxy]benzyl}-2-(4-fluorophenyl)-1,2,3,4-tetrahydroisoquinolin-6-ol The title compound was prepared as described in Example 2 using 1-{4-[(2-azaperhydroepinyl)ethoxy]benzyl}-2-(4-fluorophenyl)-6-methoxy-1,2,3,4-tetrahydroisoquinoline (0.105 g, 0.215 mmol) to provide the title compound (0.020 g, 20% yield: ES-MS (m/z) 475 [M+H]+.

Example 14

SYNTHESIS OF 2-(METHYLETHYL)-1-{4-[(2-PIPERIDYL)ETHOXY]BENZYL}-1,2,3,4-TETRAHYDROISOQUINOLIN-6-OL TRIFLUOROACETATE

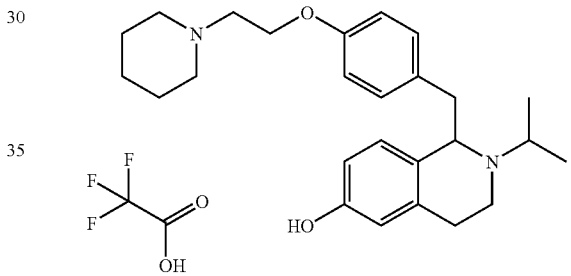

Reaction Scheme
Scheme for Examples 14, 15, 16, 19 and 20

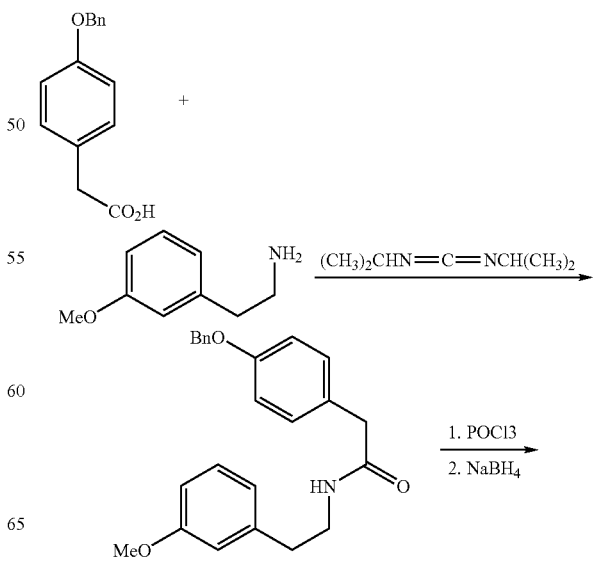

49

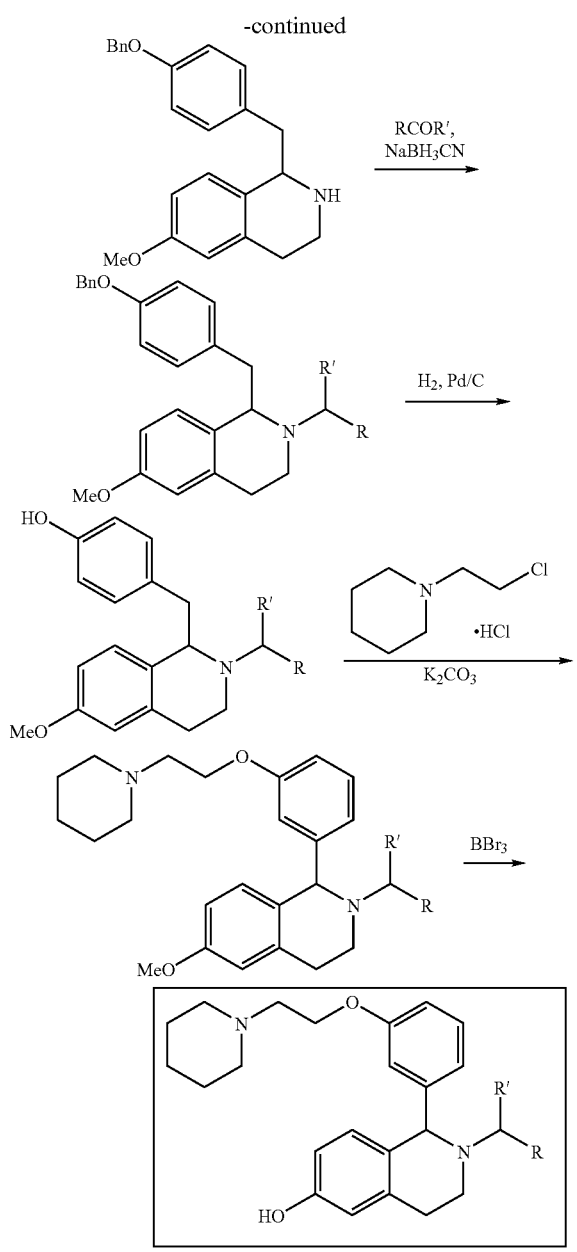

A. N-[2-(3-Methoxyphenyl)ethyl]-2-[4-(phenylmethoxy)phenyl]acetamide

To a solution of 4-benzyloxyphenylacetic acid (4.85 g 20 mmol) in dimethylformamide (30 mL) under nitrogen was added 1,3-diisopropylcarbodiimide. After 2 hours, to the solution was added 2-(3-methoxyphenyl)ethylamine (3.02 g, 20 mmol) and stirred at room temperature for 20 hours. The reaction was quenched with a saturated sodium carbonate solution and extracted with ethyl acetate. The organic layer was dried over MgSO$_4$, filtered, and concentrated. The residue was then purified by chromatography (SiO$_2$, 30-70% ethyl acetate/hexane) to provide the title compound (5.74 g, 76% yield): $^1$H NMR (CDCl$_3$) 7.38 (m, 5H), 7.14 (t, 1H), 7.07 (d, 2H), 6.91 (d, 2H), 6.74 (dd, 1H), 6.62 (m, 2H), 5.37 (br, 1H), 5.06 (s, 2H), 3.77 (s, 3H), 3.47 (s, 2H), 3.44 (t, 2H), 2.70 (t, 2H); ES-MS (m/z) 376 [M+H]$^+$.

50

B. 6-Methoxy-1-[4-(phenylmethoxy)benzyl]-1,2,3,4-tetrahydroisoquinoline

A solution of N-[2-(3-methoxyphenyl)ethyl]-2-[4-(phenylmethoxy)phenyl]acetamide (5.739 g, 15.3 mmol) and phosphorous oxychloride (15 mL) in acetonitrile (40 mL) under nitrogen was heated at 80° C. for 5 hours. Solvents were evaporated. Ethyl acetate was added and evaporated three times. The residue was dissolved in methanol (50 mL) and sodium borohydride (2.00 g, 52.9 mmol) was carefully added to the solution in small portions. After 2 hours, the reaction was quenched with water and extracted with CH$_2$Cl$_2$. The organic layer was dried over MgSO$_4$, filtered, and concentrated. The residue was then purified by chromatography (SiO$_2$, 0-10% methanol/CH$_2$Cl$_2$) to provide the title compound (1.54 g, 28% yield): $^1$H NMR (CDCl$_3$) 7.36 (m, 6H), 7.12 (d, 2H), 6.91 (d, 2H), 6.73 (dd, 1H), 6.62 (m, 1H), 5.04 (s, 2H), 4.97 (t, 1H), 4.17 (br, 1H), 3.78 (s, 3H), 3.73 (m, 1H), 3.16 (m, 2H), 2.83 (m, 3H); ES-MS (m/z) 360 [M+H]$^+$.

C. 6-Methoxy-2-(methylethyl)-1-[4-(phenylmethoxy)benzyl]-1,2,3,4-tetrahydroisoquinoline To a mixture of 6-methoxy-1-[4-(phenylmethoxy)benzyl]-1,2,3,4-tetrahydroisoquinoline (0.36 g, 1 mmol), acetone (3 mL), and sodium dihydrogenphosphate (0.4 g) in methanol (5 mL) was added sodium cyanoborohydride (0.5 g, 8 mmol). After 48 hours, the reaction was quenched with water and extracted with CH$_2$Cl$_2$. The organic layer was dried over MgSO$_4$, filtered, and concentrated to give the title compound (0.321 g, 80% yield): ES-MS (m/z) 402 [M+H]$^+$.

D. 6-Methoxy-2-(methylethyl)-1-(4-hydroxybenzyl)-1,2,3,4-tetrahydroisoquinoline A suspension of 6-methoxy-2-(methylethyl)-1-[4-(phenylmethoxy)benzyl]-1,2,3,4-tetrahydroisoquinoline (0.3 g, 0.75 mmol), palladium (10% wt) on activated carbon (0.06 g) and acetic acid (5 drops) in ethyl acetate (10 mL) was stirred under hydrogen overnight. The reaction was filtered and concentrated to provide the title compound (0.212 g, 91% yield): ES-MS (m/z) 312 [M+H]$^+$.

E. 6-Methoxy-2-(methylethyl)-1-{4-[(2-piperidyl)ethoxy]benzyl}-1,2,3,4-tetrahydroisoquinoline A mixture of 6-methoxy-2-(methylethyl)-1-(4-hydroxybenzyl)-1,2,3,4-tetrahydroisoquinoline (0.212 g, 0.68 mmol), 2-chloroethylpiperidine hydrochloride (0.25 g, 1.36 mmol), and potassium carbonate (0.47 g, 3.4 mmol) in dimethylformamide (10 mL) was heated at 80° C. overnight. After cooling to room temperature, the mixture was poured into water and extracted with CH$_2$Cl$_2$. The organic layer was dried over MgSO$_4$, filtered, and concentrated. The residue was then purified by chromatography (SiO$_2$, 0-15% methanol/CH$_2$Cl$_2$) to provide the title compound (0.201 g, 70% yield): ES-MS (m/z) 423 [M+H]$^+$.

F. 2-(Methylethyl)-1-{4-[(2-piperidyl)ethoxy]benzyl}-1,2,3,4-tetrahydroisoquinolin-6-ol Trifluoroacetate To a solution of 6-methoxy-2-(methylethyl)-1-{4-[(2-piperidyl)ethoxy]benzyl}-1,2,3,4-tetrahydroisoquinoline (0.2 g, 0.47 mmol) in CH$_2$Cl$_2$ (8 mL) at −15° C. under nitrogen was added a solution of 1.0 M boron tribromide (1.4 mL, 1.4 mmol). After stirring at −15° C. for 2 hours and at 0° C. for 2 hours, the reaction was poured into an ice and saturated sodium bicarbonate solution and extracted with ethyl acetate. The organic layer was dried over MgSO$_4$, filtered, and concentrated. The residue was then purified by HPLC (C-18 column, 10-100% acetonitrile/water with 0.1% trifluoroacetic acid) to provide the title compound (0.084 g, 43% yield): $^1$H NMR (DMSO-d$_6$) 9.65 (br, 2H), 6.93-7.06 (m, 4H), 6.66 (s, 1H), 6.33 (m, 2H), 4.62 (t, 1H), 4.34 (m, 3H), 3.96-3.00 (m 12H), 1.76 (m, 4H), 1.47 (m, 2H), 1.30 (d, 6H); ES-MS (m/z) 409 [M+H]$^+$.

Example 15

SYNTHESIS OF 2-CYCLOPENTYL-1-{4-[(2-PIPERIDYL)ETHOXY]BENZYL}-1,2,3,4-TETRAHYDROISOQUINOLIN-6-OL TRIFLUOROACETATE

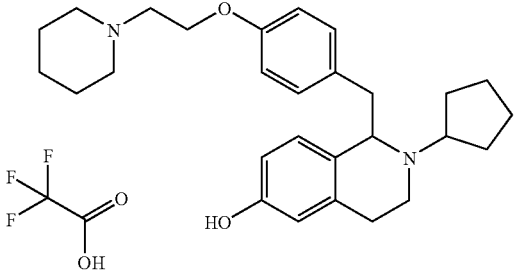

A. 2-Cyclopentyl-1-methoxy-1-[4-(phenylmethoxy)benzyl]-1,2,3,4-tetrahydroisoquinoline The title compound was prepared as described in Example 14.C, using 6-methoxy-1-[4-(phenylmethoxy)benzyl]-1,2,3,4-tetrahydroisoquinoline (0.5 g, 1.39 mmol) and cyclopentanone (0.951 g, 11.3 mmol) to provide the title compound (0.495 g, 83% yield): ES-MS (m/z) 428 [M+H]$^+$.

B. 2-Cyclopentyl-6-1-(4-hydroxybenzyl)-6-methoxy-1,2,3,4-tetrahydroisoquinoline

The title compound was prepared as described in Example 14.D, using 2-cyclopentyl-6-methoxy-1-[4-(phenylmethoxy)benzyl]-1,2,3,4-tetrahydroisoquinoline (0.495 g, 1.15 mmol) to provide the title compound (0.311 g, 79% yield): ES-MS (m/z) 338 [M+H]$^+$.

C. 2-Cyclopentyl-6-methoxy-1-{4-[(2-piperidyl)ethoxy]benzyl}-1,2,3,4-tetrahydroisoquinoline The title compound was prepared as described in Example 14.E, using 2-(cyclopentyl)-1-(4-hydroxybenzyl)-6-methoxy-1,2,3,4-tetrahydroisoquinoline (0.31 g, 0.92 mmol) to provide the title compound (0.313 g, 76% yield): ES-MS (m/z) 449 [M+H]$^+$.

D. 2-Cyclopentyl-1-{4-[(2-piperidyl)ethoxy]benzyl}-1,2,3,4-tetrahydroisoquinolin-6-ol Trifluoroacetate The title compound was prepared as described in Example 14.F, using 2-cyclopentyl-6-methoxy-1-{4-[(2-piperidyl)ethoxy]benzyl}-1,2,3,4-tetrahydroisoquinoline (0.31 g, 0.7 mmol) to provide the title compound (0.16 g, 53% yield): $^1$H NMR (DMSO-d$_6$) 9.87 (br, 1H), 9.56 (br, 1H), 6.87-7.06 (m, 4H), 6.62 (s, 1H), 6.36 (dd, 1H), 6.15 (dd, 1H), 4.48 (t, 1H), 4.29 (t, 2H), 3.94 (m, 1H), 2.8-3.8 (m 12H), 1.98-2.22 (m, 2H), 1.4-1.8 (m, 12H); ES-MS (m/z) 435 [M+H]$^+$.

Example 16

SYNTHESIS OF 1-{4-[(2-PIPERIDYL)ETHOXY]BENZYL}-2-(TETRAHYDROPYRAN-4-YL)-1,2,3,4-TETRAHYDROISOQUINOLIN-6-OL TRIFLUOROACETATE

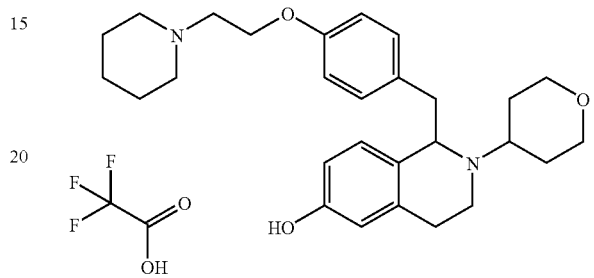

A. 6-Methoxy-1-[4-(phenylmethoxy)benzyl]-2-(tetrahydropyran-4-yl)-1,2,3,4-tetrahydroisoquinoline The title compound was prepared as described in Example 14.C, using 6-methoxy-1-[4-(phenylmethoxy)benzyl]-1,2,3,4-tetrahydroisoquinoline (0.5 g, 1.39 mmol) and tetrahydro-4H-pyran-4-one (1.084 g, 10.8 mmol) to provide the title compound (0.479 g, 78% yield): ES-MS (m/z) 444 [M+H]$^+$.

B. 1-(4-Hydroxybenzyl)-6-methoxy-2-(tetrahydropyran-4-yl)-1,2,3,4-tetrahydroisoquinoline The title compound was prepared as described in Example 14.D, using 6-methoxy-1-[4-(phenylmethoxy)benzyl]-2-(tetrahydropyran-4-yl)-1,2,3,4-tetrahydroisoquinoline (0.47 g, 0.1 mmol) to provide the title compound (0.324 g, 85% yield): ES-MS (m/z) 354 [M+H]$^+$.

C. 6-Methoxy-1-{4-[(2-piperidyl)ethoxy]benzyl}-2-(tetrahydropyran-4-yl)-1,2,3,4-tetrahydroisoquinoline The title compound was prepared as described in Example 14.E, using 1-(4-hydroxybenzyl)-6-methoxy-2-(tetrahydropyran-4-yl)-1,2,3,4-tetrahydroisoquinoline (0.32 g, 0.92 mmol) to provide the title compound (0.342 g, 80% yield): ES-MS (m/z) 465 [M+H]$^+$.

D. 1-{4-[(2-Piperidyl)ethoxy]benzyl}-2-(tetrahydropyran-4-yl)-1,2,3,4-tetrahydroisoquinolin-6-ol Trifluoroacetate The title compound was prepared as described in Example 14.F, using 6-methoxy-1-{4-[(2-piperidyl)ethoxy]benzyl}-2-(tetrahydropyran-4-yl)-1,2,3,4-tetrahydroisoquinoline (0.34 g, 0.73 mmol) to provide the title compound (0.156 g, 47% yield): $^1$H NMR (DMSO-d$_6$) 9.79 (br, 1H), 9.6 (br, 1H), 6.91-7.07 (m, 4H), 6.66 (s, 1H), 6.05-6.43 (m, 2H), 4.69 (t, 1H), 4.31 (t, 2H), 2.99-4.0 (m 12H), 2.2 (m, 1H), 2.06 (m, 4H), 1.5-1.86 (m, 8H), 1.41 (m, 2H); ES-MS (m/z) 451 [M+H]$^+$.

Example 17

SYNTHESIS OF 2-(4-FLUOROPHENYL)-1-{4-[(2-MORPHOLINYL)ETHOXY]BENZYL}-1,2,3,4-TETRAHYDROISOQUINOLIN-6-OL

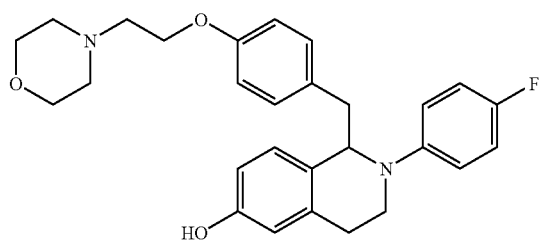

A. 2-(4-Fluorophenyl)-6-methoxy-1-{4-[(2-morpholinyl)ethoxy]benzyl}-1,2,3,4-tetrahydroisoquinoline The title compound was prepared as described in Example 3.D using 2-(4-fluorophenyl)-6-methoxy-1-{4-hydroxybenzyl}-1,2,3,4-tetrahydroisoquinoline (0.220 g, 0.6 mmol) and 4-(2-chloroethyl)morpholine hydrochloride (0.124 g, 0.67 mmol) to provide the title compound (0.23 g, 80% yield): ES-MS (m/z) 477 [M+H]$^+$.

B. 2-(4-Fluorophenyl)-1-{4-[(2-morpholinyl)ethoxy]benzyl}-1,2,3,4-tetrahydroisoquinolin-6-ol The title compound was prepared as described in Example 2, using 2-(4-fluorophenyl)-6-methoxy-1-{4-[(2-morpholinyl)ethoxy]benzyl}-1,2,3,4-tetrahydroisoquinoline (0.23 g, 0.48 mmol) to provide the title compound (0.130 g, 46% yield): $^1$H NMR (CDCl$_3$) 6.9(m, 4H), 6.75(m, 3H), 6.6(m, 4H), 4.7(t, 1H), 4.1(m, 2H), 3.74(m, 4H), 3.5(m, 2H), 3.1(m, 1H), 2.9(m, 2H), 2.8(m, 2H), 2.6(m, 1H), 2.6(m, 4H); ES-MS (m/z) 463 [M+H]$^+$.

Example 18

SYNTHESIS OF 2-(4-FLUOROPHENYL)-1-{3-[(2-PIPERIDYL)ETHOXY]BENZYL}-1,2,3,4-TETRAHYDROISOQUINOLIN-6-OL

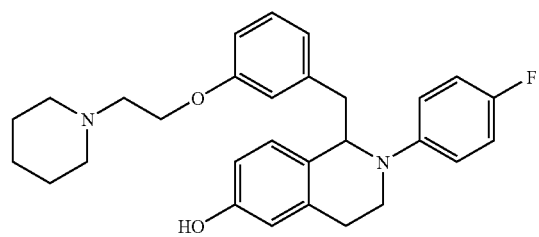

A. N-{2-(3-Methoxyphenyl)ethyl}-N-(4-fluorophenyl)-2-{3-hydroxyphenyl}-acetamide The title compound was prepared as described in Example 34.B using 3-hydroxyphenylacetic acid (0.456 g, 3 mmol) and 4-fluorophenyl)-{2-(3-methoxyphenyl)ethyl}amine (0.73 g, 3 mmol) to provide the title compound (0.7 g, 62% yield): ES-MS (m/z) 380 [M+H]$^+$.

B. 2-(4-Fluorophenyl)-1-(3-hydroxybenzyl)-6-methoxy-1,2,3,4-tetrahydroisoquinoline The title compound was prepared as described in Example 1.D, using N-{2-(3-methoxyphenyl)ethyl}-N-(4-fluorophenyl)-2-{3-hydroxyphenyl}acetamide (0.7 g, 1.8 mmol) to provide the title compound (0.15 g, 23% yield): ES-MS (m/z) 363 [M+H]$^+$.

C. 2-(4-Fluoropheny)-6-methoxy-1-{3-[(2-piperidyl)ethoxy]benzyl}-1,2,3,4-tetrahydroisoquinoline The title compound was prepared as described in Example 3.D, using 2-(4-fluorophenyl)-1-(3-hydroxybenzyl)-6-methoxy-1,2,3,4-tetrahydroisoquinoline (0.15 g, 0.4 mmol) to provide the title compound (0.17 g, 89% yield): ES-MS (m/z) 475 [M+H]$^+$.

D. 2-(4-Fluorophenyl)-1-{3-[(2-piperidyl)ethoxy]benzyl}-1,2,3,4-tetrahydroisoquinolin-6-ol The title compound was prepared as described in Example 2 using 2-(4-fluorophenyl)-6-methoxy-1-{3-[(2-piperidyl)ethoxy]benzyl}-1,2,3,4-tetrahydroisoquinoline (0.174 g, 0.37 mmol). Purification by column chromatography (SiO$_2$, ethyl acetate:ethanol, 8:2) provided the title compound (0.027 g, 16% yield): ES-MS (m/z) 461 [M+H]$^+$.

Example 19

SYNTHESIS OF 2-METHYL-1-{4-[(2-PIPERIDYL)ETHOXY]BENZYL}-1,2,3,4-TETRAHYDROISOQUINOLIN-6-OL TRIFLUOROACETATE

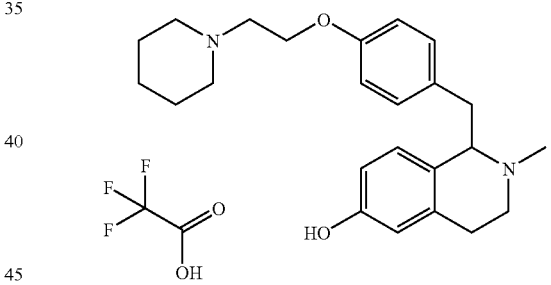

A. 6-Methoxy-2-methyl-1-[4-(phenylmethoxy)benzyl]-1,2,3,4-tetrahydroisoquinoline The title compound was prepared as described in Example 14.B, providing the title compound (0.854 g, 0.015% yield).

B. 1-(4-Hydroxybenzyl)-6-methoxy-2-methyl-1,2,3,4-tetrahydroisoquinoline

The title compound was prepared as described in Example 14.D, using 6-methoxy-2-methyl-1-[4-(phenylmethoxy)benzyl]-1,2,3,4-tetrahydroisoquinoline (0.84 g, 2.25 mmol) to provide the title compound (0.534 g, 84% yield): ES-MS (m/z) 284 [M+H]$^+$.

C. 6-Methoxy-2-methyl-1-{4-[(2-piperidyl)ethoxy]benzyl}-1,2,3,4-tetrahydroisoquinoline The title compound was prepared as described in Example 14.E, 1-(4-hydroxybenzyl)-6-methoxy-2-methyl-1,2,3,4-tetrahydroisoquinoline (0.534 g, 1.88 mmol) to provide the title compound (0.216 g, 29% yield): ES-MS (m/z) 395 [M+H]+.

D. 2-Methyl-1-{4-[(2-piperidyl)ethoxy]benzyl}-1,2,3,4-tetrahydroisoquinolin-6-ol Trifluoroacetate The title compound was prepared as described in Example 14.F, using 6-methoxy-2-methyl-1-{4-[(2-piperidyl)ethoxy]benzyl}-1,2,3,4-tetrahydroisoquinoline (0.20 g, 0.507 mmol) to provide the title compound (0.103 g, 54% yield): ES-MS (m/z) 381 [M+H]+.

Example 20

SYNTHESIS OF 2-CYCLOHEXYL-1-{4-[(2-PIPERIDYL)ETHOXY]BENZYL}-1,2,3,4-TETRAHYDROISOQUINOLIN-6-OL TRIFLUOROACETATE

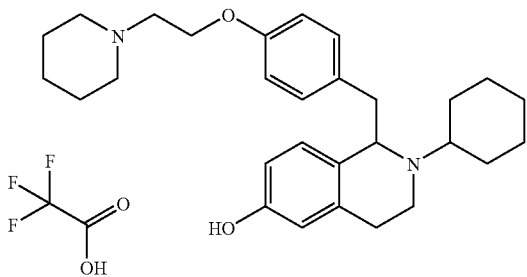

A. 2-Cyclohexyl-6-methoxy-1-[4-(phenylmethoxy)benzyl]-1,2,3,4-tetrahydroisoquinoline The title compound was prepared as described in Example 14.C, using 6-methoxy-1-[4-(phenylmethoxy)benzyl]-1,2,3,4-tetrahydroisoquinoline (0.5 g, 1.39 mmol) and cyclohexanone (0.588 g. 6.0 mmol) to provide the title compound (0.324 g, 53% yield): ES-MS (m/z) 442 [M+H]+.

B. 2-Cyclohexyl-1-(4-hydroxybenzyl)-6-methoxy-1,2,3,4-tetrahydroisoquinoline

The title compound was prepared as described in Example 14.D, using 2-cyclohexyl-6-methoxy-1-[4-(phenylmethoxy)benzyl]-1,2,3,4-tetrahydroisoquinoline (0.32 g, 0.73 mmol) to provide the title compound (0.124 g, 48% yield): $^1$H NMR (CDCl$_3$) 6.86 (d, 2H), 6.70 (d, 2H), 6.58 (m, 4H), 4.06 (t, 1H), 3.76 (s, 3H), 3.24 (m, 1H), 3.04 (m, 2H), 2.75 (m, 2H), 2.54 (m, 2H), 1.69-1.87 (m, 4H), 1.58 (m, 1H), 1.13-1.25 (m, 5H); ES-MS (m/z) 352 [M+H]+.

C. 2-Cyclohexyl-6-methoxy-1-{4-[(2-piperidyl)ethoxy]benzyl}-1,2,3,4-tetrahydroisoquinoline The title compound was prepared as described in Example 14.E, using 2-cyclohexyl-1-(4-hydroxybenzyl)-6-hydroxy-1,2,3,4-tetrahydroisoquinoline (0.124 g. 0.35 mmol) to provide the title compound (0.95 g, 59% yield): ES-MS (m/z) 463 [M+H]+.

D. 2-Cyclohexyl-1-{4-[(2-piperidyl)ethoxy]benzyl}-1,2,3,4-tetrahydroisoquinolin-6-ol Trifluoroacetate The title compound was prepared as described in Example 14.F, using 2-cyclohexyl-6-methoxy-1-{4-[(2-piperidyl)ethoxy]benzyl}-1,2,3,4-tetrahydroisoquinoline (0.95 g, 0.2 mmol) to provide the title compound (0.052 g, 57% yield): $^1$H NMR (CDCl$_3$) 11.65 (br, 1H), 11.2 (br, 1H), 6.79 (d, 2H), 6.73 (d, 1H), 6.67 (d, 2H), 6.54 (dd, 1H), 6.07 (d, 1H), 4.45 (dd, 1H), 4.28 (t, 2H), 3.70 (m, 3H), 3.55 (dd, 1H), 3.44 (t, 2H), 2.71-3.08 (m 6H), 1.87-2.16 (m, 9H), 1.6 (m, 4H), 1.4 (m, 1H), 1.2 (m, 3H); ES-MS (m/z) 449 [M+H]+.

Example 21

SYNTHESIS OF 1-{4-[(2-(N-BENZYL-N-ETHYL)AMINO)ETHOXY]BENZYL}-2-(4-FLUOROPHENYL)-1,2,3,4-TETRAHYDROISOQUINOLIN-6-OL

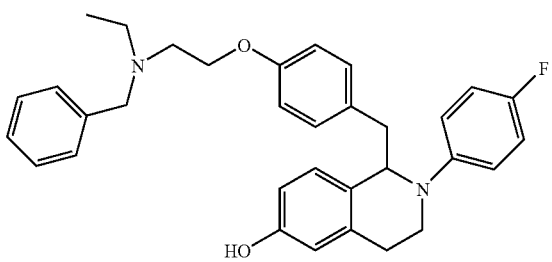

A. 1-{4-[(2-(N-benzyl-N-ethyl)amino)ethoxy]benzyl}-2-(4-fluorophenyl)-6-methoxy-1,2,3,4-tetrahydroisoquinoline The title compound was prepared as described in Example 3.D using N-(2-chloroethyl)-N-ethyl-benzylamine hydrochloride (0.115 g, 0.5 mmol) to provide the title compound (0.18 g, 77% yield): ES-MS (m/z) 525 [M+H]+.

B. 1-{4-[(2-(N-benzyl-N-ethyl)amino)ethoxy]benzyl}-2-(4-fluorophenyl)-1,2,3,4-tetrahydroisoquinolin-6-ol The title compound was prepared as described in Example 2 using 1-{4-[(2-(N-benzyl-N-ethyl)amino)ethoxy]benzyl}-6-methoxy-2-(4-fluoropheny)-1,2,3,4-tetrahydroisoquinoline (0.11 g, 0.2 mmol). Purification by preparative HPLC (C-18 column, 10-100% acetonitrile/water with 0.1% trifluoroacetic acid) provided the title compound (0.045 g, 20% yield): m.p. 47-49° C.; ES-MS (m/z) 511 [M+H]+.

Example 22

SYNTHESIS OF 2-(4-FLUOROBENZOYL)-1-{4-[(2-PIPERIDYL)ETHOXY]BENZYL}-1,2,3,4-TETRAHYDROISOQUINOLIN-6-OL TRIFLUOROACETATE

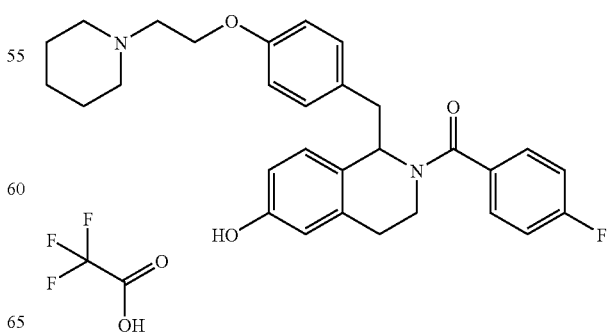

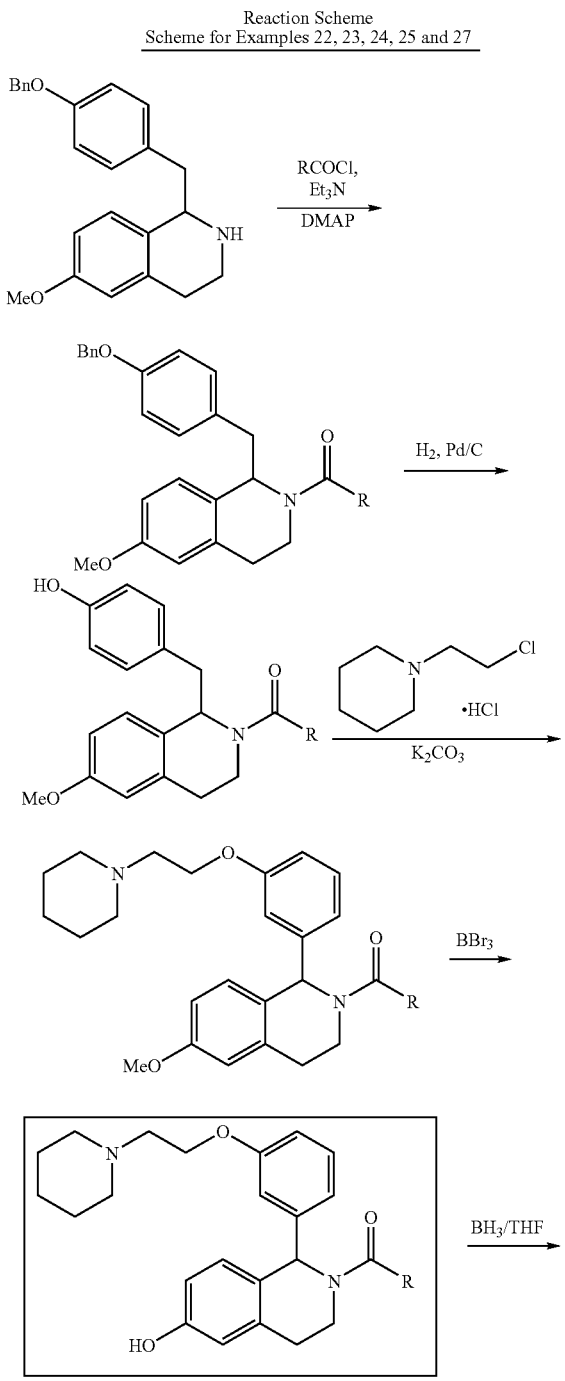

Reaction Scheme
Scheme for Examples 22, 23, 24, 25 and 27

Examples 22, 23, & 24

Examples 25 & 27

A. 2-(4-Fluorobenzoyl)-6-methoxy-1-[4-(phenylmethoxy)benzyl]-1,2,3,4-tetrahydroisoquinoline The title compound was prepared as described in Example 24.A, using 6-methoxy-1-[4-(phenylmethoxy)benzyl]-1,2,3,4-tetrahydroisoquinoline (0.72 g, 2.0 mmol) and 4-fluorobenzoyl chloride (0.475 g, 3.0 mmol) to provide the title compound (0.786 g, 82% yield): ES-MS (m/z) 482 [M+H]$^+$.

B. 2-(4-Fluorobenzoyl)-1-(4-hydroxybenzyl)-6-methoxy-1,2,3,4-tetrahydroisoquinoline The title compound was prepared as described in Example 14.D, using 2-(4-fluorobenzoyl)-6-methoxy-1-[4-(phenylmethoxy)benzyl]-1,2,3,4-tetrahydroisoquinoline (0.74 g, 1.54 mmol) to provide the title compound (0.563 g, 94% yield): $^1$H NMR (CDCl$_3$) 7.26-7.37 (m, 2H), 7.41 (br, 1H), 7.01-7.15 (m, 3H), 6.61-6.92 (m, 7H), 6.00 (dd, 1H), 4.87 (m, 1H), 3.82 (s, 3H), 3.71 (m, 1H), 3.47 (m, 1H), 2.62-3.24 (m, 4H); ES-MS (m/z) 392 [M+H]$^+$.

C. 2-(4-Fluorobenzoyl)-6-methoxy-1-{4-[(2-piperidyl)ethoxy]benzyl}-1,2,3,4-tetrahydroisoquinoline The title compound was prepared as described in Example 14.E, using 2-(4-fluorobenzoyl)-1-(4-hydroxybenzyl)-6-methoxy-1,2,3,4-tetrahydroisoquinoline (0.51 g, 1.3 mmol) to provide the title compound (0.601 g, 92% yield): ES-MS (m/z) 503 [M+H]$^+$.

D. 2-(4-Fluorobenzoyl)-1-{4-[(2-piperidyl)ethoxy]benzyl}-1,2,3,4-tetrahydroisoquinolin-6-ol Trifluoroacetate The title compound was prepared as described in Example 14.F, using 2-(4-fluorobenzoyl)-6-methoxy-1-{4-[(2-piperidyl)ethoxy]benzyl}-1,2,3,4-tetrahydroisoquinoline (0.60 g, 1.19 mmol) to provide the title compound (0.279 g, 48% yield): $^1$H NMR (DMSO-d$_6$) 9.55 (br, 2H), 7.21 (m, 2H), 6.92-7.10 (m, 5H), 6.52-6.64 (m, 3H), 5.69 (t, 1H), 4.6 (dd, 1H), 4.29 (t, 2H), 3.3-3.65 (m, 5H), 2.56-3.16 (m, 7H), 1.41-1.80 (m, 6H); ES-MS (m/z) 489 [M+H]$^+$.

Example 23

SYNTHESIS OF 2-(4-HYDROXYBENZOYL)-1-{4-[(2-PIPERIDYL)ETHOXY]BENZYL}-1,2,3,4-TETRAHYDROISOQUINOLIN-6-OL TRIFLUOROACETATE

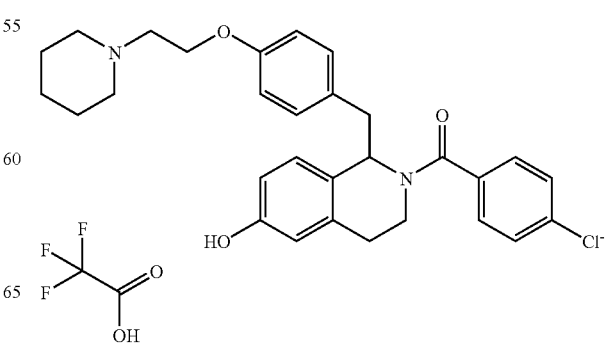

A. 6-Methoxy-2-(4-methoxybenzoyl)-1-[4-(phenyl-methoxy)benzyl]-1,2,3,4-tetrahydroisoquinoline The title compound was prepared as described in Example 24.A, using 6-methoxy-1-[4-(phenylmethoxy)benzyl]-1,2,3,4-tetrahydroisoquinoline (0.72 g, 2.0 mmol) and 4-methoxybenzoyl chloride (0.512 g, 3.0 mmol) to provide the title compound (0.717 g, 73% yield): ES-MS (m/z) 494 [M+H]$^+$.

B. 1-(4-Hydroxybenzyl)-6-methoxy-2-(4-methoxy-1benzoyl)-1,2,3,4-tetrahydroisoquinoline The title compound was prepared as described in Example 14.D, using 6-methoxy-2-(4-methoxy 1 benzoyl)-1-[4-(phenylmethoxy)benzyl]-1,2,3,4-tetrahydroisoquinoline (0.717 g, 1.45 mmol) to provide the title compound (0.533 g, 91% yield): $^1$H NMR (CDCl$_3$) 7.8 (br, 1H), 7.15-7.08 (m, 3H), 6.57-6.92 (m, 7H), 6.02 (dd, 1H), 4.90 (m, 1H), 3.81 (s, 3H), 3.79 (s, 3H), 3.73 (m, 1H), 3.47 (m, 1H), 2.61-3.20 (m, 4H); ES-MS (m/z) 404 [M+H]$^+$.

C. 6-Methoxy-2-(4-methoxybenzoyl)-1-{4-[(2-piperidyl)ethoxy]benzyl}-1,2,3,4-tetrahydroisoquinoline The title compound was prepared as described in Example 14.E, using 1-(4-hydroxybenzyl)-6-methoxy-2-(4-methoxybenzoyl)-1,2,3,4-tetrahydroisoquinoline (0.48 g, 1.19 mmol) to provide the title compound (0.541 g, 88% yield): ES-MS (m/z) 515 [M+H]$^+$.

D. 2-(4-Hydroxybenzoyl)-1-{4-[(2-piperidyl)ethoxy]benzyl}-1,2,3,4-tetrahydroisoquinolin-6-ol Trifluoroacetate The title compound was prepared as described in Example 14.F, using 6-methoxy-2-(4-methoxybenzoyl)-1-{4-[(2-piperidyl)ethoxy]benzyl}-1,2,3,4-tetrahydroisoquinoline (0.541 g, 1.05 mmol) to provide the title compound (0.174 g, 34% yield): $^1$H NMR (DMSO-d$_6$) 9.41 (br, 2H), 7.19 (d, 1H), 6.50-7.02 (m, 10H), 5.65 (t, 1H), 4.5 (m, 1H), 4.29 (t, 2H), 3.3-3.9 (m, 7H), 2.6-3.2 (m, 5H), 1.4-1.8 (m, 6H); ES-MS (m/z) 487 [M+H]$^+$.

Example 24

SYNTHESIS OF 2-BENZOYL-1-{4-[(2-PIPERIDYL)ETHOXY]BENZYL}-1,2,3,4-TETRAHYDROISOQUINOLIN-6-OL TRIFLUOROACETATE

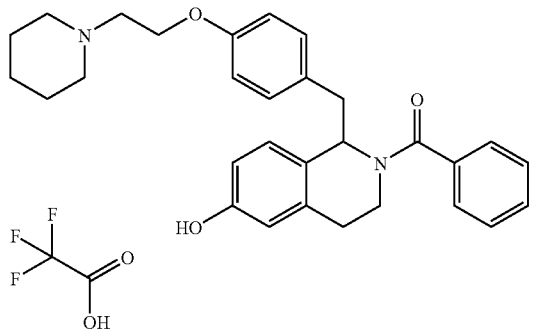

A. 2-Benzoyl-6-methoxy-1-[4-(phenylmethoxy)benzyl]-1,2,3,4-tetrahydroisoquinoline To a solution of 6-methoxy-1-[4-(phenylmethoxy)benzyl]-1,2,3,4-tetrahydroisoquinoline (0.72 g, 2.0 mmol), 4-dimethylaminopyridine (0.2 g), and triethylamine (1.5 mL) in CH$_2$Cl$_2$ (8 mL) at room temperature under nitrogen was added neat benzoyl chloride (0.42 g, 3.0 mmol) dropwise. The reaction was stirred overnight, quenched with a solution of saturated sodium bicarbonate, and extracted with CH$_2$Cl$_2$. The organic layer was dried over MgSO$_4$, filtered, and concentrated. The residue was purified by chromatography (SiO$_2$, 30-50% ethyl acetate/hexane) to provide the title compound (0.835 g, 90% yield): ES-MS (m/z) 464 [M+H]$^+$.

B 2-Benzoyl-1-(4-hydroxybenzyl)-6-methoxy-1,2,3,4-tetrahydroisoquinoline

The title compound was prepared as described in Example 14.D, using 2-benzoyl-6-methoxy-1-[4-(phenylmethoxy)benzyl]-1,2,3,4-tetrahydroisoquinoline (0.8 g, 1.72 mmol) to provide the title compound (0.624 g, 97% yield): $^1$H NMR (CDCl$_3$) 7.26-7.37 (m, 2H), 7.01-7.17 (m, 4H), 6.59-6.87 (m, 6H), 6.01 (t, 1H), 4.88 (m, 1H), 3.81 (s, 3H), 3.67 (m, 1H), 3.47 (m, 1H), 2.64-3.23 (m, 4H); ES-MS (m/z) 374 [M+H]$^+$.

C. 2-Benzoyl-6-methoxy-1-{4-[(2-piperidyl)ethoxy]benzyl}-1,2,3,4-tetrahydroisoquinoline The title compound was prepared as described in Example 14.E, using 2-benzoyl-1-(4-hydroxybenzyl)-6-methoxy-1,2,3,4-tetrahydroisoquinoline (0.60 g, 1.6 mmol) to provide the title compound (0.521 g, 67% yield).

D. 2-Benzoyl-1-{4-[(2-piperidyl)ethoxy]benzyl}-1,2,3,4-tetrahydroisoquinolin-6-ol Trifluoroacetate The title compound was prepared as described in Example 14.F, using 2-benzoyl-6-methoxy-1-{4-[(2-piperidyl)ethoxy]benzyl}-1,2,3,4-tetrahydroisoquinoline (0.50 g, 1.03 mmol) to provide the title compound (0.137 g, 28% yield): $^1$H NMR (DMSO-d$_6$) 9.5 (br, 2H), 7.3-7.41 (m, 2H), 7.08-7.23 (m, 4H), 6.82-6.95 (m, 3H), 6.51-6.64 (m, 2H), 5.69 (m, 1H), 4.59 (m, 1H), 4.29 (t, 2H), 3.3-3.9 (m, 5H), 2.5-3.17 (m 7H), 1.6-1.9 (m, 4H), 1.39 (m, 2H); ES-MS (m/z) 471 [M+H]$^+$.

Example 25

SYNTHESIS OF 2-(4-FLUOROBENZYL)-1-{4-[(2-PIPERIDYL)ETHOXY]BENZYL}-1,2,3,4-TETRAHYDROISOQUINOLIN-6-OL TRIFLUOROACETATE

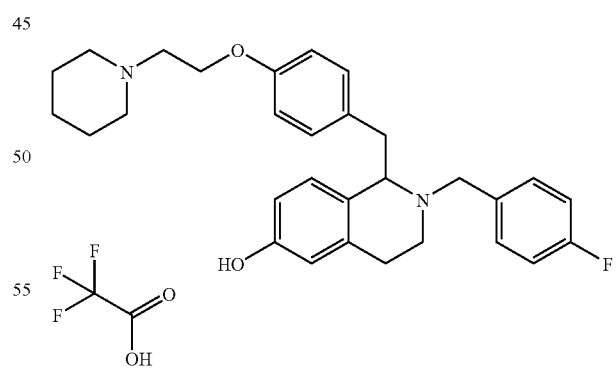

The title compound was prepared as described in Example 27.A, using 2-(4-fluorobenzoyl)-1-{4-[(2-piperidyl)ethoxy]benzyl}-1,2,3,4-tetrahydroisoquinolin-6-ol (0.10 g, 0.205 mmol) to provide the title compound (0.054 g, 56% yield): $^1$H NMR (DMSO-d$_6$) 10.0 (br, 2H), 7.32-7.75 (m, 4H), 6.95 (m, 4H), 6.66 (d, 1H), 6.40 (dd, 1H), 6.13 (dd, 1H), 4.6 (m, 1H), 4.43 (t, 2H), 2.6-3.9 (m, 10H), 2.0-1.4 (m, 10H); ES-MS (m/z) 475 [M+H]$^+$.

Example 26
SYNTHESIS OF 2-(4-FLUOROPHENYL)-1-{4-NITROBENZYL}-1,2,3,4-TETRAHYDROISOQUINOLIN-6-OL
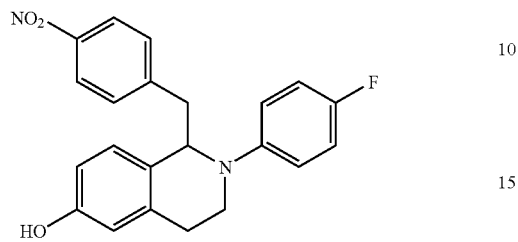
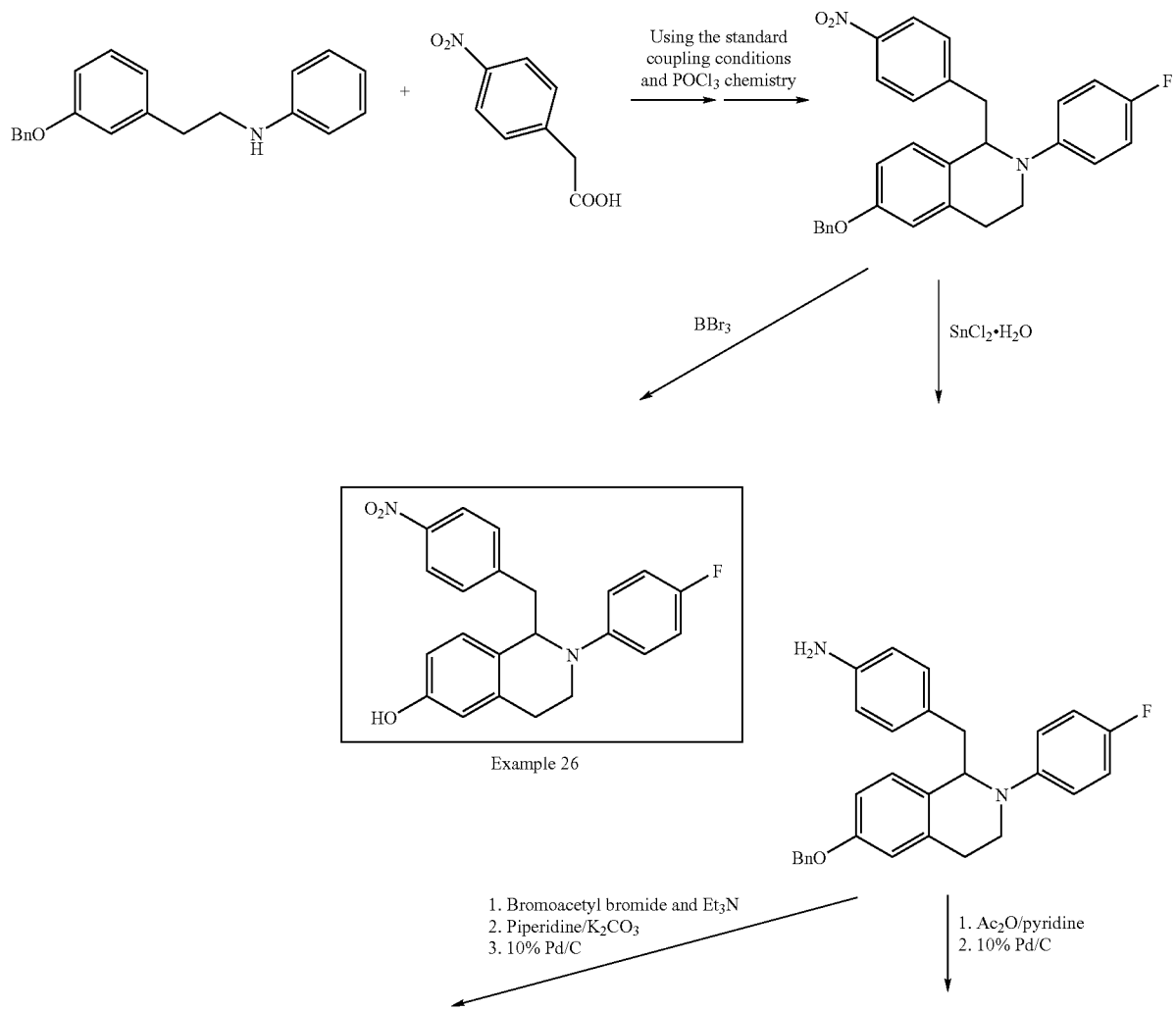
Reaction Scheme
Scheme for Example 26, 46, 49 (Nitrogen-containing sidechain analogs)

-continued

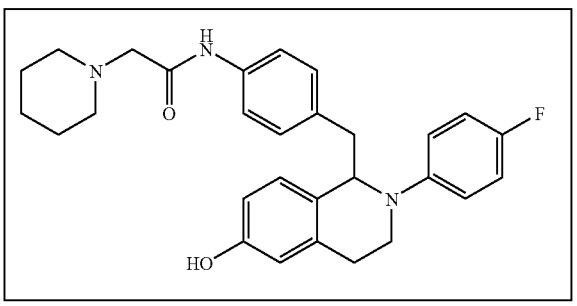

Example 49

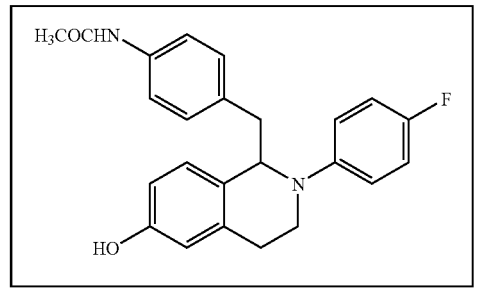

Example 46

A. N-{4-Fluorophenyl}-2-(4-nitrophenyl)-N-{2-[3-(phenylmethoxy)phenyl]ethyl}acetamide The title compound was prepared as described in Example 12.E using 4-nitrophenylacetic acid (5.1 g, 28 mmol) to provide the title compound (8.7 g, 90% yield): ES-MS (m/z) 485 [M+H]$^+$.

B. 2-(4-Fluorophenyl)-6-phenylmethoxy-1-(4-nitrobenzyl)-1,2,3,4-tetrahydroisoquinoline The title compound was prepared as described in Example 12.E using N-{4-fluorophenyl}-2-(4-nitrophenyl)-N-{2-[3-(phenylmethoxy)phenyl]ethyl}acetamide (8.7 g, 18 mmol) to provide the title compound (3.5 g, 41.5% yield): ES-MS (m/z) 469 [M+H]$^+$.

C. 2-(4-Fluorophenyl)-1-(4-nitrobenzyl)-1,2,3,4-tetrahydroisoquinolin-6-ol

The title compound was prepared as described in Example 3.D using 2-(4-fluorophenyl)-6-phenylmethoxy-1-(4-nitrobenzyl)-1,2,3,4-tetrahydroisoquinoline (0.11 g, 0.23 mmol). Purification by column chromatography (SiO$_2$, hexanes/ethyl acetate, 2:1) provided the title compound (0.029 g, 33% yield): ES-MS (m/z) 379 [M+H]$^+$.

Example 27

SYNTHESIS OF 2-BENZYL-1-{4-[(2-PIPERIDYL)ETHOXY]BENZYL}-1,2,3,4-TETRAHYDROISO-QUINOLIN-6-OL TRIFLUOROACETATE

A. 2-Benzyl-1-{4-[(2-piperidyl)ethoxy]benzyl}-1,2,3,4-tetrahydroisoquinolin-6-ol Trifluoroacetate To a solution of 2-Benzoyl-1-{4-[(2-piperidyl)ethoxy]benzyl}-1,2,3,4-tetrahydroisoquinolin-6-ol (0.1 g, 0.21 mmol) in tetrahydrofuran (10 mL) was added a solution of 1.0 M borane-tetrahydrofuran complex in tetrahydrofuran (0.21 mL, 0.21 mmol), and the reaction was heated at 80° C. for 3-4 hours. After cooling to room temperature, a 5% hydrochloride solution was added, and the mixture was stirred for another hour. The reaction was then basified with a solution of saturated sodium bicarbonate and extracted with CH$_2$Cl$_2$. The organic layer was dried over MgSO$_4$, filtered, and concentrated. The residue was purified by HPLC (C-18 column, 10-100% acetonitrile/water with 0.1% trifluoroacetic acid) to provide the title compound (0.047 g, 48% yield): $^1$H NMR (CDCl$_3$) 11.2 (br, 2H), 7.41 (m, 3H), 6.80 (d, 2H), 6.70 (d, 2H), 6.6 (m, 1H), 6.18 (m, 4H), 4.34 (m, 1H), 4.17 (t, 2H), 3.92 (m, 1H), 3.76 (m, 2H), 3.62 (m, 4H), 3.40 (m, 1H), 3.01 (t, 2H), 2.00 (m, 4H), 1.88 (m, 4H), 1.75 (m, 2H); ES-MS (m/z) 457 [M+H]$^+$.

Example 28

SYNTHESIS OF 2-(2-CHLOROPYRIMIDIN-4-YL)-1-{4-[(2-PIPERIDYL)ETHOXY]BENZYL}-1,2,3,4-TETRAHYDROISOQUINOLIN-6-OL TRIFLUOROACETATE

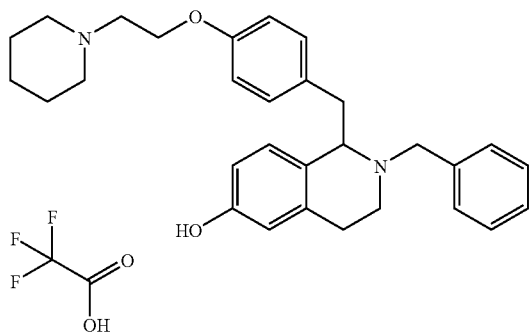

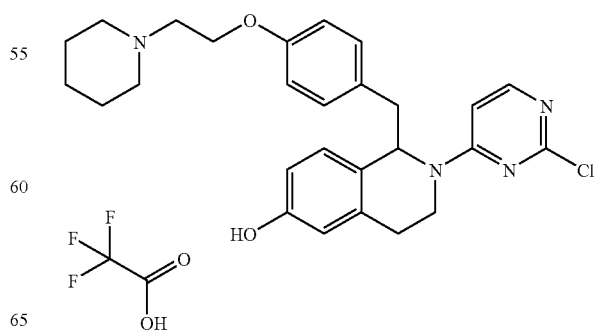

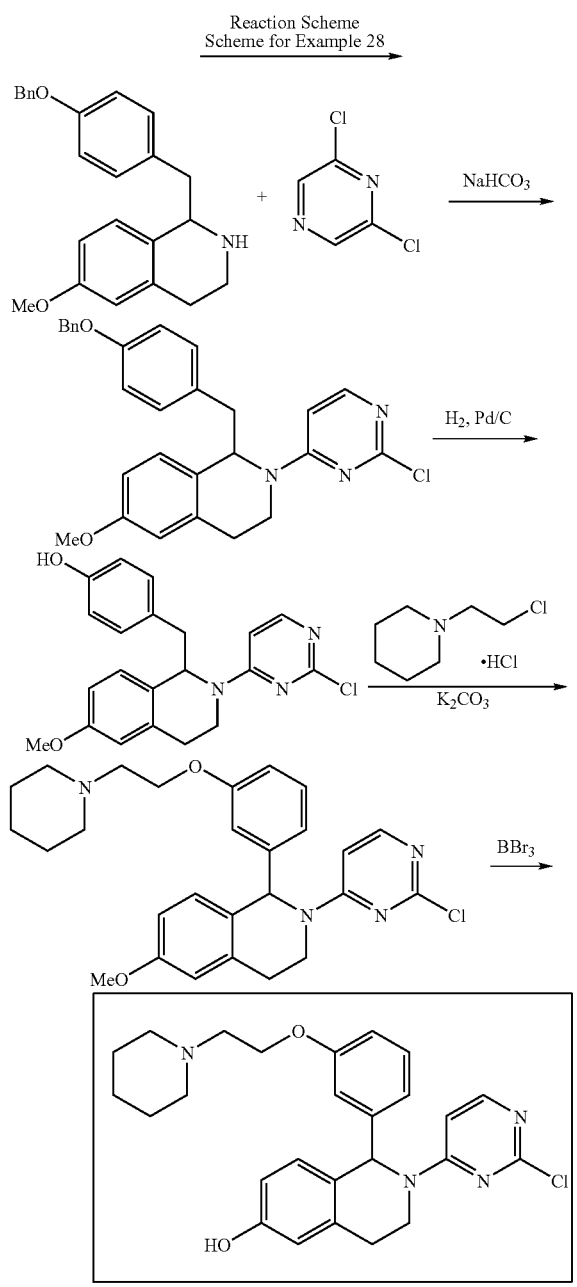

3H), 6.37 (m, 1H), 5.9 (d, 1H), 5.03 (s, 2H), 4.97 (m, 1H), 3.80 (s, 3H), 3.25-3.62 (m, 2H), 3.13 (m, 1H), 2.86 (m, 3H); ES-MS (m/z) 472 [M+H]+.

B. 2-(2-Chloropyrimidin-4-yl)-1-(4-hydroxybenzyl)-6-methoxy-1,2,3,4-tetrahydroisoquinoline The title compound was prepared as described in Example 14.D, using 2-(2-chloropyrimidin-4-yl)-6-methoxy-1-[4-(phenylmethoxy)benzyl]-1,2,3,4-tetrahydroisoquinoline (0.70 g, 1.48 mmol) to provide the title compound (0.089 g, 16% yield): 1H NMR (CDCl3) 7.91 (d, 1H), 6.91 (m, 3H), 6.71 (m, 4H), 6.37 (m, 1H), 5.85 (d, 1H), 4.75 (dd, 1H), 3.80 (s, 3H), 3.3-3.65 (m, 2H), 2.6-3.25 (m, 4H); ES-MS (m/z) 382 [M+H]+.

C. 2-(2-Chloropyrimidin-4-yl)-6-methoxy-1-{4-[(2-piperidyl)ethoxy]benzyl}-1,2,3,4-tetrahydroisoquinoline The title compound was prepared as described in Example 14.E, using 2-(2-chloropyrimidin-4-yl)-1-(4-hydroxybenzyl)-6-methoxy-1,2,3,4-tetrahydroisoquinoline (0.089 g, 0.23 mmol) to provide the title compound (0.11 g, 97% yield): ES-MS (m/z) 493 [M+H]+.

D. 2-(2-Chloropyrimidin-4-yl)-1-{4-[(2-piperidyl)ethoxy]benzyl}-1,2,3,4-tetrahydroisoquinolin-6-ol Trifluoroacetate The title compound was prepared as described in Example 14.F, using 2-(2-chloropyrimidin-4-yl)-6-methoxy-1-{4-[(2-piperidyl)ethoxy]benzyl}-1,2,3,4-tetrahydroisoquinoline (0.11 g, 0.22 mmol) to provide the title compound (0.84 g, 76% yield): 1H NMR (CDCl3) 11.9 (br, 2H), 8.58 (d, 1H), 8.1 (m, 1H), 7.8 (m, 1H), 7.06 (d, 1H), 6.96 (m, 1H), 6.87 (m, 1H), 6.64-6.7 (m, 2H), 5.98 (m, 1H), 5.00 (m, 1H), 4.31 (t, 2H), 3.41-3.73 (4H), 2.81-3.14 (m, 4H), 2.04 (m, 4H), 1.92 (m, 4H), 1.87 (m, 2H); ES-MS (m/z) 479 [M+H]+.

Example 29

SYNTHESIS OF 2-[(2-DIMETHYLAMINO)PYRIMIDIN-4-YL]-1-{4-[(2-PIPERIDYL)ETHOXY]BENZYL}-1,2,3,4-TETRAHYDROISOQUINOLIN-6-OL TRIFLUOROACETATE

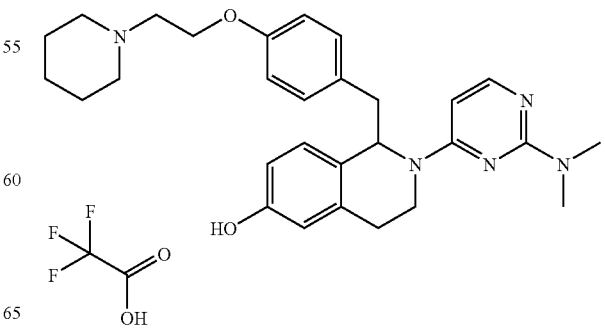

A. 2-(2-Chloropyrimidin-4-yl)-6-methoxy-1-[4-(phenylmethoxy)benzyl]-1,2,3,4-tetrahydroisoquinoline A mixture of 6-methoxy-1-[4-(phenylmethoxy)benzyl]-1,2,3,4-tetrahydroisoquinoline (0.72 g, 2.0 mmol), 2,4-dichloropyrimidine (0.298 g, 2.0 mmol), and sodium bicarbonate (0.2 g, 2.4 mmol) in ethanol (10 mL) was heated at 80° C. for 3 hours. It was quenched with water and extracted with CH2Cl2. The organic layer was dried over MgSO4, filtered, and concentrated. The residue was purified by chromatography (SiO2, 30-6-% ethyl acetate/hexane) to provide the title compound (0.749 g, 79% yield): 1H NMR (CDCl3) 7.95 (d, 1H), 7.32-7.41 (m, 4H), 6.94 (d, 2H), 6.83 (d, 2H), 6.69 (m, Reaction Scheme
Scheme for Example 29

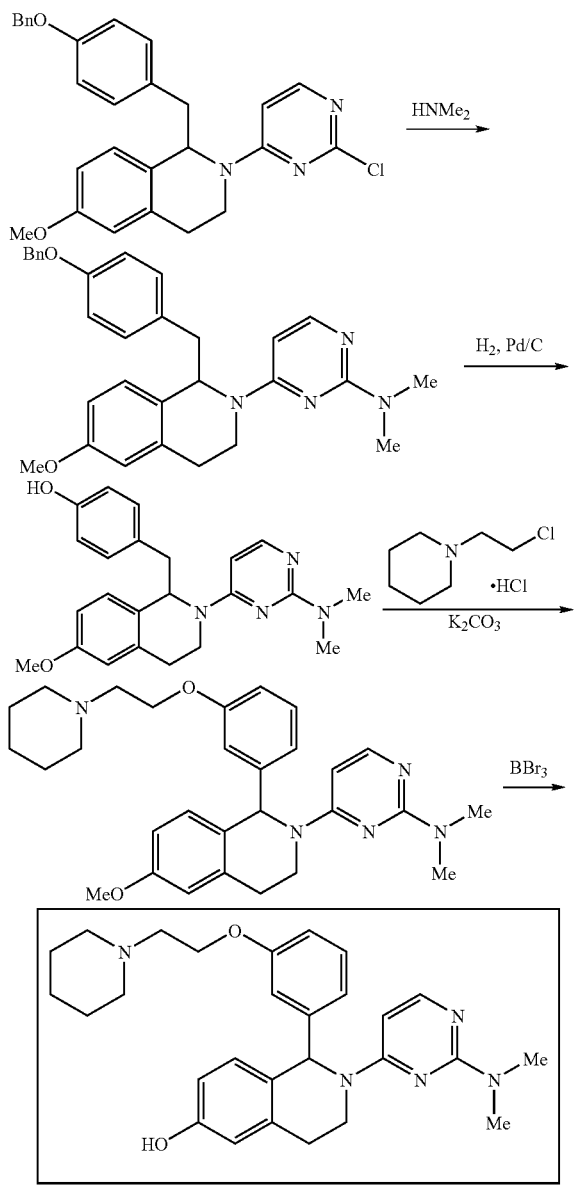

A. 2-[(2-Dimethylamino)pyrimidin-4-yl]-6-methoxy-1-[4-(phenylmethoxy)benzyl]-1,2,3,4-tetrahydroisoquinoline A solution of 2-(2-chloropyrimidin-4-yl)-6-methoxy-1-(4-(phenylmethoxy)benzyl)-1,2,3,4-tetrahydroisoquinoline (from Example 28) in 40% dimethylamine/water (15 mL) in a sealed tube was heated at 110° C. for 4 hours. The reaction was quenched with water and extracted with $CH_2Cl_2$. The organic layer was dried over $MgSO_4$, filtered, and concentrated to provide the title compound (0.683 g, 96% yield): $^1$H NMR ($CDCl_3$) 7.91 (d, 1H), 7.32-7.43 (m, 4H), 6.87 (d, 2H), 6.80 (d, 2H), 6.62-6.73 (m, 4H), 5.77 (d, 1H), 5.02 (s, 2H), 3.78 (s, 3H), 3.52 (m, 2H), 3.19 (s, 6H), 3.12 (m, 1H), 3.01 (m, 2H), 2.83 (m, 1H), 2.70 (m, 1H); ES-MS (m/z) 481 [M+H]$^+$.

B. 2-[(2-Dimethylamino)pyrimidin-4-yl]-1-(4-hydroxybenzyl)-6-methoxy-1,2,3,4-tetrahydroisoquinoline The title compound was prepared as described in Example 14.D, using 2-[(2-dimethylamino)pyrimidin-4-yl]-6-methoxy-1-[4-(phenylmethoxy)benzyl]-1,2,3,4-tetrahydroisoquinoline (0.68 g, 1.4 mmol) to provide the title compound (0.351 g, 64% yield): $^1$H NMR ($CDCl_3$) 7.82 (s, 1H), 6.82 (m, 3H), 6.66 (m, 5H), 5.71 (d, 1H), 3.78 (s, 3H), 3.51 (m, 2H), 3.17 (s, 6H), 2.66-3.21 (m, 5H); ES-MS (m/z) 391 [M+H]$^+$.

C. 2-[(2-Dimethylamino)pyrimidin-4-yl]-6-methoxy-1-{4-[(2-piperidyl)ethoxy]benzyl}-1,2,3,4-tetrahydroisoquinoline The title compound was prepared as described in Example 14.E, using 2-[(2-dimethylamino)pyrimidin-4-yl]-1-(4-hydroxybenzyl)-6-methoxy-1,2,3,4-tetrahydroisoquinoline (0.3 g, 0.77 mmol) to provide the title compound (0.298 g, 77% yield): $^1$H NMR ($CDCl_3$) 7.91 (d, 1H), 7.86 (d, 2H), 6.70-6.74 (m, 3H), 6.61-6.65 (m, 2H), 5.77 (d, 1H), 4.06 (t, 2H), 3.78 (s, 3H), 3.51 (m, 2H), 3.51 (m, 1H), 3.18 (s, 6H), 3.02 (m, 1H), 2.76 (t, 2H), 2.61-2.86 (m, 3H), 2.51 (m, 4H), 1.62 (m, 4H), 1.45 (m, 2H); ES-MS (m/z) 502 [M+H]$^+$.

D. 2-[(2-Dimethylamino)pyrimidin-4-yl]-1-{4-[(2-piperidyl)ethoxy]benzyl}-1,2,3,4-tetrahydroisoquinolin-6-ol Trifluoroacetate The title compound was prepared as described in Example 14.F, using 2-[(2-dimethylamino)pyrimidin-4-yl]-6-methoxy-1-{4-[(2-piperidyl)ethoxy]benzyl}-1,2,3,4-tetrahydroisoquinoline (0.295 g, 0.59 mmol) to provide the title compound (0.121 g, 42% yield): $^1$H NMR ($CDCl_3$) 11.7 (br, 2H), 7.83 (d, 1H), 7.45 (d, 1H), 6.89-6.96 (m, 2H), 6.65-6.80 (m, 4H), 5.35 (d, 1H), 4.31 (t, 2H), 3.63-3.69 (m, 3H), 3.43-3.58 (m, 4H), 3.24 (s, 3H), 3.21 (s, 3H), 3.02 (t, 2H), 2.82 (m, 4H), 1.91 (m, 4H), 1.87 (m, 2H); ES-MS (m/z) 488 [M+H]$^+$.

Example 30

SYNTHESIS OF 1-[(4-HYDROXYPHENYL)METHYL]-2-[4-(MORPHOLIN-4-YLACETAMIDO)PHENYL]-1,2,3,4-TETRAHYDROISOQUINOLIN-6-OL

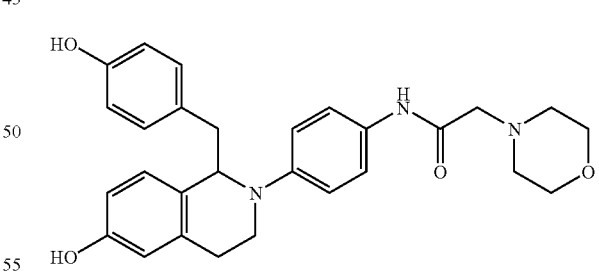

A. 6-Methoxy-2-(4-nitrophenyl)-1-[4-(phenylmethoxy)benzyl]-1,2,3,4-tetrahydroisoquinoline A solution of 6-methoxy-1-[4-(phenylmethoxy)benzyl]-1,2,3,4-tetrahydroisoquinoline (2.10 g, 5.84 mmol) and 1-fluoro-4-nitrobenzene (1.65 g, 11.7 mmol) in 40 mL of DMSO was treated with powdered $K_2CO_3$ (1.62 g, 11.7 mmol) and the reaction mixture was warmed at 120° C. for 12 h. The reaction mixture was cooled to room temperature and 300 mL of water was added. The aqueous layer was extracted with $CH_2Cl_2$ and the combined organic layer was washed with water, dried over MgSO$_4$, then concentrated under reduced pressure. The crude product was purified by flash chromatography to provide the title compound (2.50 g, 89%). ES-MS, (m/z) 481 [M+H]$^+$.

B. 2-(4-Aminophenyl)-6-methoxy-1-[4-(phenylmethoxy)benzyl]-1,2,3,4-tetrahydroisoquinoline A suspension of 6-methoxy-2-(4-nitrophenyl)-1-[4-(phenylmethoxy)benzyl]-1,2,3,4-tetrahydroisoquinoline (0.70 g, 1.46 mmol) and SnCl$_2$*H$_2$O (1.35 g, 6.0 mmol) in 20 mL of THF/HOAc (1:1) and 3 mL of water was heated at 60° C. for 3 h. The reaction mixture was concentrated under reduced pressure and the resulting residue was quenched by the addition of saturated aqueous NaHCO$_3$ (50 mL). The aqueous layer was extracted with EtOAc (3×50 mL) and the combined organic layer was dried over MgSO$_4$ then concentrated. The crude product was purified by flash chromatography to provide the title compound (0.63 g, 95% yield). ES-MS, (m/z) 451 [M+H]$^+$.

C. 6-Methoxy-2-[4-(morpholin-4-ylacetamide)phenyl]-1-[4-(phenylmethoxy)benzyl]-1,2,3,4-tetrahydroisoquinoline A solution of 2-(4-aminophenyl)-6-methoxy-1-[4-(phenylmethoxy)benzyl]-1,2,3,4-tetrahydroisoquinoline (0.225 g, 0.50 mmol) and TEA (0.061 g, 0.6 mmol) in 3 mL of CH$_2$Cl$_2$ at 0° C. was treated with bromoacetyl bromide (0.121 g, 0.60 mmol) in 1 mL of CH$_2$Cl$_2$. After 30 minutes, excess morpholine was added (0.20 mL) and the reaction mixture was warned to room temperature and stirred overnight. The reaction was quenched by the addition of saturated aqueous NaHCO$_3$ (0.5 mL) and the aqueous layer was extracted with CH$_2$Cl$_2$ (4×2 mL). The combined organic layer was dried over MgSO$_4$ and concentrated. The crude product was purified by flash chromatography to provide the title compound (0.263 g, 91% yield). ES-MS, (m/z) 578 [M+H]$^+$.

D. 1-[4-(hydroxyphenyl)methyl]-6-methoxy-2-[4-(morpholin-4-ylacetamide)phenyl]-1,2,3,4-tetrahydroisoquinoline A solution of 6-methoxy-2-[4-(morpholin-4-ylacetamide)phenyl]-1-[4-(phenylmethoxy)phenylmethyl]-1,2,3,4-tetrahydroisoquinoline (0.24 g, 0.42 mmol) in 2 mL of EtOH/THF (1:1) was degassed and placed under a H$_2$ atmosphere. Palladium (10% wt. on activated carbon, 0.050 g) in 0.5 mL of EtOH was introduced and the reaction mixture was stirred overnight. The mixture was filtered through celite and the filter cake was rinsed with CH$_2$Cl$_2$. The solution was concentrated and the crude product purified by column chromatography to provide the title compound (0.18 g, 89% yield). ES-MS, (m/z) 488 [M+H]$^+$.

E. 1-(4-Hydroxybenzyl)-2-[4-(morpholin-4-ylacetamido)phenyl]-1,2,3,4-tetrahydroisoquinolin-6-ol A solution of 1-(4-hydroxybenzyl)-6-methoxy-2-[4-(morpholin-4-ylacetamide)phenyl]-1,2,3,4-tetrahydroisoquinoline (0.060 g, 0.123 mmol) in 1 mL of CH$_2$Cl$_2$ at 0° C. was treated with BBr$_3$ (1M in CH$_2$Cl$_2$, 0.5 mL, 0.5 mmol). The reaction mixture was stirred for 1 hour at 0° C. then it was quenched by the addition of saturated aqueous NaHCO$_3$ (2 mL). The aqueous layer was extracted with CH$_2$Cl$_2$ (4×2 mL) and the combined organic layer was dried over MgSO$_4$ then concentrated. The crude product was purified by column chromatography to provide the title compound (0.035 g, 60% yield). ES-MS, (m/z) 474 [M+H]$^+$.

Example 31

SYNTHESIS OF 2-(4-ACETAMIDOPHENYL)-1-(4-HYDROXYBENZYL)-1,2,3,4-TETRAHYDROISOQUINOLIN-6-OL

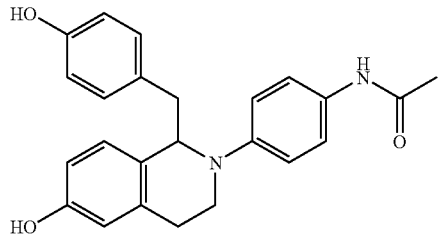

A. 2-(4-Acetamidophenyl)-6-methoxy-1-[4-(phenylmethoxy)benzyl]-1,2,3,4-tetrahydroisoquinoline A solution of 2-(4-aminophenyl)-6-methoxy-1-[4-(phenylmethoxy)benzyl]-1,2,3,4-tetrahydroisoquinoline (0.205 g, 0.46 mmol) and TEA (0.060 g, 0.6 mmol) in 1 mL of CH$_2$Cl$_2$ at 0° C. was treated with acetyl chloride (0.043 g, 0.55 mmol). The reaction mixture was warmed to room temperature and stirred for 3 hours. The reaction was quenched by the addition of saturated aqueous NaHCO$_3$ (0.5 mL). The organic layer was separated and the aqueous layer was extracted with CH$_2$Cl$_2$ (3×2 mL). The combined organic layer was dried over MgSO$_4$ then concentrated. The crude product was purified by column chromatography to provide the title compound (0.195 g, 87% yield). ES-MS, (m/z) 493 [M+H]$^+$.

B. 2-(4-Acetamidophenyl)-1-(4-hydroxybenzyl)-6-methoxy-1,2,3,4-tetrahydroisoquinoline A solution of 2-(4-acetamidophenyl)-6-methoxy-1-[4-(phenylmethoxy)benzyl]-1,2,3,4-tetrahydroisoquinoline (0.190 g, 0.386 mmol) in 2 mL of EtOH/THF (1:1) was debenzylated with 10% Pd/C under an H$_2$ atmosphere as described in Example 30.F to provide the title compound (0.148 g, 95% yield): ES-MS (m/z) 403 [M+H]$^+$.

C. 2-(4-Acetamidophenyl)-1-(4-hydroxybenzyl)-1,2,3,4-tetrahydroisoquinolin-6-ol A solution of 2-(4-acetamidophenyl)-1-(4-hydroxybenzyl)-6-methoxy-1,2,3,4-tetrahydroisoquinoline (0.025 g, 0.062 mmol) in 1 mL of CH$_2$Cl$_2$ was demethylated with BBr$_3$ as described in Example 30.G to provide the title compound (0.018 g, 75% yield). ES-MS, (m/z) 389 [M+H]$^+$.

Example 32

SYNTHESIS OF 2-(4-ACETAMIDOPHENYL)-1-{[4-(2-PIPERIDYLETHOXY)PHENYL]METHYL}-1,2,3,4-TETRAHYDROISOQUINOLIN-6-OL

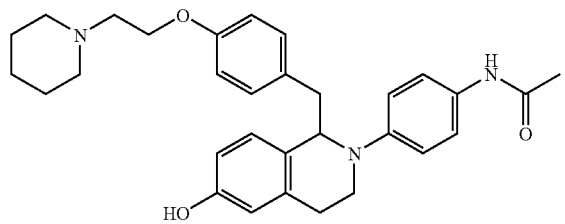

A. 2-(4-Acetamidophenyl)-6-methoxy-1-{[4-(2-piperidyl)ethoxy]benzyl}-1,2,3,4-tetrahydroisoquinoline A solution of 2-(4-acetamidophenyl)-1-(4-hydroxybenzyl)-1,2,3,4-tetrahydroisoquinolin-6-ol (0.120 g, 0.298 mmol) in 2 mL of DMF was O-alkylated with 1-(2-chloroethyl)piperidine monohydrochloride and $K_2CO_3$ as described in Example 3.D to provide the title compound (0.102 g, 67% yield): ES-MS, (m/z) 514 $[M+H]^+$.

B. 2-(4-Acetamidophenyl)-1-{[4-(2-piperidyl)ethoxy]benzyl}-1,2,3,4-tetrahydroisoquinolin-6-ol A solution of N-[4-(6-methoxy-1-{[4-(2-piperidyl)ethoxy]benzyl}-2-1,2,3,4-tetrahydroisoquinolyl)phenyl]acetamide (0.102 g, 0.199 mmol) was demethylated with $BBr_3$ in $CH_2Cl_2$ as described in Example 30.G to provide the title compound (0.062 g, 62%). ES-MS, (m/z) 500 $[M+H]^+$.

Example 33

SYNTHESIS OF 2-[4-(MORPHOLIN-4-YLACETAMIDO)PHENYL]-1-{[4-(2-PIPERIDYL)ETHOXY]BENZYL}-1,2,3,4-TETRAHYDROISOQUINOLIN-6-OL

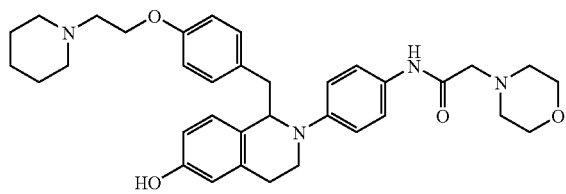

A. 6-Methoxy-2-[4-(morpholin-4-ylacetamido)phenyl]-1-{[4-(2-piperidyl)ethoxy]benzyl}-1,2,3,4-tetrahydroisoquinoline A suspension of N-(4-{1-[(4-hydroxyphenyl)methyl]-6-methoxy-2-(1,2,3,4-tetrahydro-isoquinolyl)}-phenyl)-2-morpholin-4-ylacetamide (0.120 g, 0.246 mmol), $K_2CO_3$ (0.086 g, 0.62 mmol), and 1-(2-chloroethyl)piperidine monohydrochloride (0.052 g, 0.28 mmol) in 1 mL of DMF was warmed at 90° C. for 8 hours. The solvent was removed under vacuum and the residue was suspended in 10 mL of $CH_2Cl_2$/MeOH (5:1). The resulting suspension was filtered through celite and the filtrate was concentrated. The crude product was purified by flash chromatography to provide the title compound (0.121 g, 8.2% yield). ES-MS, (m/z) 599 $[M+H]^+$.

B. 2-[4-(Morpholin-4-ylacetamido)phenyl]-1-{[4-(2-piperidyl)ethoxy]benzyl}-1,2,3,4-tetrahydroisoquinolin-6-ol A solution of 6-methoxy-2-[4-(morpholin-4-ylacetamido)phenyl]-1-{[4-(2-piperidyl)ethoxy]benzyl}-1,2,3,4-tetrahydroisoquinoline (0.080 g, 0.134 mmol) in 1 mL of $CH_2Cl_2$ was demethylated with $BBr_3$ as described in Example 30.G to provide the title compound after flash chromatography (0.038 g, 48% yield): ES-MS, (m/z) 585 $[M+H]^+$.

Example 34

SYNTHESIS OF 2-(NAPHTHYL)-1-{4-[(2-PIPERIDYL)ETHOXY]BENZYL}-1,2,3,4-TETRAHYDROISOQUINOLIN-6-OL

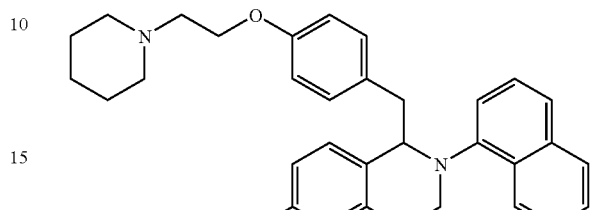

Reaction Scheme
Scheme for Examples 34, 36, 38, 39 and 43

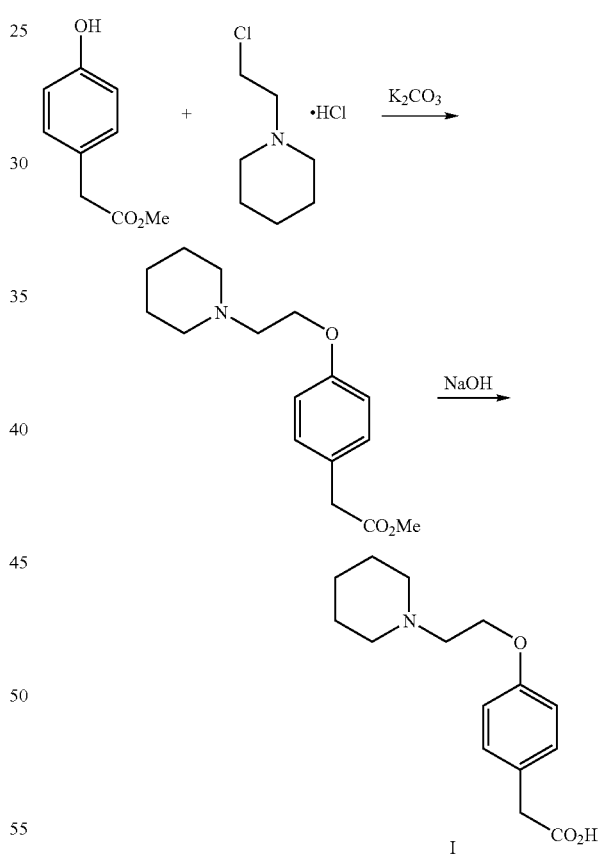

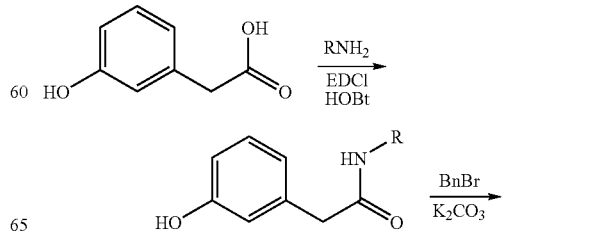

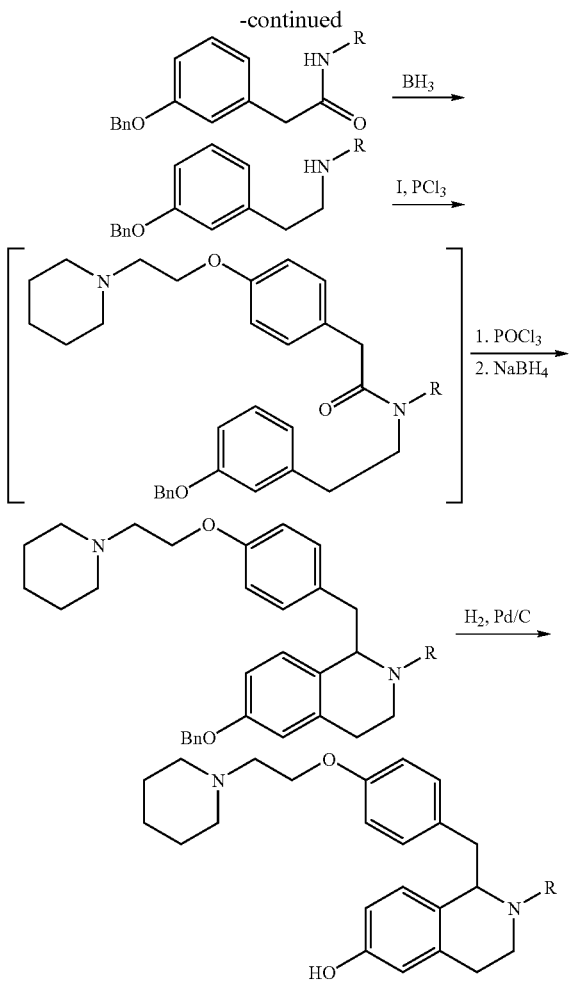

A. 2-{[4-(2-Piperidyl)ethoxy]phenyl}acetic Acid

A mixture of methyl 4-hydroxyphenylacetate (4.985 g, 30 mmol), 2-chloroethylpiperidine hydrochloride (6.624 g, 36 mmol), and potassium carbonate (10.35 g, 75 mmol) in dimethylformamide (30 mL) was heated at 80° C. overnight. After cooling to room temperature, the mixture was poured into water and extracted with ethyl acetate. The organic layer was washed with brine, dried over MgSO$_4$, filtered, and concentrated. The residue was dissolved in methanol (30 mL) and 5 N sodium hydroxide (15 mL) then heated at 90° C. for 1.5 hour. Methanol was evaporated and the basic solution was acidified with 6 N hydrochloride solution. Water was evaporated, and the residue was extracted with methanol and concentrated. The residue was then extracted with CH$_2$Cl$_2$ and concentrated to provide the title compound (6.002 g, 76% yield): $^1$H NMR (CDCl$_3$) 12.04 (br, 1H), 7.19 (d, 2H), 6.82 (d, 2H), 4.49 (m, 1H), 3.38-3.67 (m 5H), 2.83 (m, 4H), 2.22 (m, 2H), (1.87 (m, 3H), 1.42 (m, 1H); ES-MS (m/z) 264 [M+H]$^+$.

B. 2-(3-Hydroxyphenyl)-N-naphthylacetamide

To a solution of 3-hydroxyphenylacetic acid (3.04 g, 20 mmol) in dimethylformamide (30 mL) and 1-hydroxybenzotriazole (3.24 g, 24 mmol) at 0° C. under nitrogen was added 1-(3-dimethylaminopropyl)-3-ethylcarbodiimide hydrochloride (4.60 g, 24 mmol). After 30 minutes, 1-aminonaphthyline (2.86 g, 20 mmol) was added, and the mixture was stirred overnight at room temperature. The reaction was quenched with 5% hydrochloride and extracted with ethyl acetate. The organic layer was washed with a 10% sodium carbonate solution, washed with brine, dried over MgSO$_4$, filtered, and concentrated to provide the title compound (5.239 g, 94% yield): $^1$H NMR (DMSO-d$_6$) 9.66 (br, 1H), 9.04 (s, 1H), 7.96 (dd, 1H), 7.85 (dd, 1H), 7.74 (dd, 1H), 7.68 (d, 1H), 7.18-7.49 (m, 3H), 7.16 (t, 1H), 6.92 (m 2H), 6.73 (d, 1H), 3.76 (s, 2H); ES-MS (m/z) 278 [M+H]$^+$.

C. N-Naphthyl-2-[3-(phenylmethoxy)phenyl]acetamide

A mixture of 2-(3-hydroxyphenyl)-N-naphthylacetamide (5.00 g, 18.03 mmol), benzyl bromide (3.76 g, 220 mmol), and potassium carbonate (4.14 g, 30.0 mmol) in acetone (50 mL) was heated to reflux overnight. The reaction was quenched with water and extracted with ethyl acetate. The organic layer was dried over MgSO$_4$, filtered, and concentrated to provide the title compound (3.176 g, 48% yield): $^1$H NMR (DMSO-d$_6$) 10.13 (br, 1H), 8.06 (m, 1H), 7.94 (m, 1H), 7.77 (d, 1H), 7.67 (d, 1H), 7.26-7.56 (m, 9H), 6.92-7.11 (m, 3H), 5.11 (s, 2H), 3.79 (s, 2H); ES-MS (m/z) 368 [M+H]$^+$.

D. Naphthyl{2-[3-(phenylmethoxy)phenyl]ethyl}amine

To a solution of N-naphthyl-2-[3-(phenylmethoxy)phenyl]acetamide (3.00 g, 8.16 mmol) in tetrahydrofuran (25 mL) under nitrogen was added a solution of 1.0 M borane-tetrahydrofuran complex in tetrahydrofuran (12.3 mL, 12.3 mmol) and heated to reflux for 5 hours. The reaction was quenched with a 5% hydrochloride solution. After stirring 30 minutes, the reaction was basified with a 10% sodium carbonate solution and extracted with CH$_2$Cl$_2$. The organic layer was dried over MgSO$_4$, filtered, and concentrated to provide the title compound (2.724 g, 94% yield): $^1$H NMR (CDCl$_3$) 7.78 (d, 1H), 7.67 (d, 1H), 7.18-7.46 (m, 10H), 6.89 (m, 3H), 6.66 (d, 1H), 5.01 (s, 2H), 4.40 (br, 1H), 3.55 (t, 2H), 3.05 (t, 2H); ES-MS (m/z) 354 [M+H]$^+$.

E. 2-Naphthyl-6-(phenylmethoxy)-1-{4-[(2-piperidyl)ethoxy]benzyl}-1,2,3,4-tetrahydroisoquinoline To a solution of naphthyl{2-[3-(phenylmethoxy)phenyl]ethyl}amine (0.42 g, 1.19 mmol) and 2-([4-(2-piperidyl)ethoxy]phenylacetic acid (0.316 g, 1.20 mmol) in chlorobenzene (6 mL) under nitrogen was added a solution of 2.0 M phosphorus trichloride in CH$_2$Cl$_2$ (0.6 mL, 1.2 mmol), The reaction was heated at 140° C. for 12 hours. After cooling to room temperature, the solvent was evaporated. Methanol and ethyl acetate were added and concentrated several times to provide a residue (0.508 g).

The residue was dissolved in acetonitrile (8 mL) and phosphorus oxychloride (2 mL), and then heated at 80° C. for 16 hours. After cooling to room temperature, the solvents were evaporated. Ethyl acetate was added and evaporated several times. The residue was dissolved in methanol (10 mL) and sodium borohydride (0.6 g, 15.8 mmol) was added in small portions. After stirring at room temperature overnight, the reaction was quenched with a solution of saturated sodium bicarbonate and extracted with ethyl acetate. The organic layer was dried over MgSO$_4$, filtered, and concentrated. The residue was purified by chromatography (SiO$_2$, 0-10% methanol/CH$_2$Cl$_2$) to provide the title compound (0.217 g, 31% yield): $^1$H NMR (CDCl$_3$) 8.06 (d, 1H), 7.79 (d, 1H), 7.33-7.51 (m, 8H), 7.20 (m, 1H), 6.68-6.96 (m, 8H), 5.06 (s, 2H), 4.66 (t, 1H), 4.11 (m, 1H), 4.01 (t, 2H), 3.76 (m, 1H), 3.45 (dd, 1H), 3.18 (m 1H), 2.90 (dd, 1H), 2.69-2.78 (m and t, 3H), 2.48 (m, 4H), 1.59 (m, 4H), 1.43 (m, 2H); ES-MS (m/z) 483 [M+H]+.

F. 2-Naphthyl-1-{4-[(2-piperidyl)ethoxy]benzyl}-1,2,3,4-tetrahydroisoquinolin-6-ol The title compound was prepared as described in Example 14.D, using 2-naphthyl-6-(phenylmethoxy)-1-{4-[(2-piperidyl)ethoxy]benzyl}-1,2,3,4-tetrahydroisoquinoline (0.21 g, 0.36 mmol) to provide the title compound (0.127 g, 72% yield): ): $^1$H NMR (CDCl$_3$) 8.04 (d, 1H), 7.78 (d, 1H), 7.37-7.47 (m, 4H), 7.22 (m, 1H), 6.92 (m, 3H), 6.54-6.91 (m, 5H), 4.61 (t, 1H), 4.02 (t, 2H), 3.60-3.79 (m, 3H), 3.37 (m, 1H), 3.16 (m 1H), 2.93 (m, 1H), 2.74 (t, 2H), 2.52 (m, 4H), 1.61 (m, 4H), 1.44 (m, 2H); ES-MS (m/z) 493 [M+H]+.

Example 35

SYNTHESIS OF 2-[(4-FLUORO-2-METHYL)PHENYL]-1-{4-[(2-PIPERIDYL)ETHOXY]BENZYL}-1,2,3,4-TETRAHYDROISOQUINOLIN-6-OL

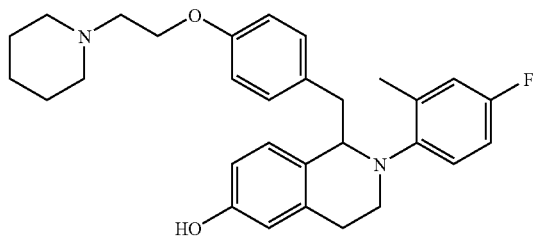

A. 2-(3-Hydroxyphenyl)-N-[(4-fluoro-2-methyl)phenyl]acetamide

The title compound was prepared as described in Example 34.B using 2-methyl-4-fluoro aniline (2.5 g, 20 mmol) to provide the title compound (4.2 g, 81% yield): ES-MS (m/z) 260 [M+H]+.

B. 2-[3-(Phenylmethoxy)phenyl]-N-[(4-fluoro-2-methyl)phenyl]acetamide

The title compound was prepared as described in Example 34.C using 2-(3-hydroxyphenyl)-N-[(4-fluoro-2-methyl)phenyl]acetamide (4 g, 15.4 mmol) to provide the title compound (4.4 g, 82% yield): ES-MS (m/z) 350 [M+H]+.

C. {2-[3-(Phenylmethoxy)phenyl]ethyl}[4-fluoro-2-methylphenyl]amine

The title compound was prepared as described in Example 34.D using 2-[3-(phenylmethoxy)phenyl]-N-[(4-fluoro-2-methyl)phenyl]acetamide (4.3 g, 12.3 mmol) to provide the title compound (3.47 g, 84% yield): ES-MS (m/z) 336 [M+H]+.

D. N-{(4-Fluoro-2-methyl)phenyl}-2-(4-hydroxyphenyl)-N-[2-{3-(phenylmethoxy)phenyl}ethyl]acetamide The title compound was prepared as described in Example 34.B from {2-[3-(phenylmethoxy)phenyl]ethyl}[4-fluoro-2-methylphenyl]amine (1 g, 3 mmol) to provide the title compound (0.7 g, 50% yield): ES-MS (m/z) 470 [M+H]+.

E. 2-[(4-Fluoro-2-methyl)phenyl]-6-phenylmethoxy-1-(4-hydroxybenzyl)-1,2,3,4-tetrahydroisoquinoline The title compound was prepared as described in Example 1.D using N-{(4-fluoro-2-methyl)phenyl}-2-(4-hydroxyphenyl)-N-[2-{3-(phenylmethoxy) phenyl}ethyl]acetamide (0.7 g., 1.5 mmol). Purification by column chromatography (SiO$_2$, ethylacetate/hexanes, 5:1) provided the title compound (0.124 g, 18% yield): ES-MS (m/z) 454 [M+H]+.

F. 2-[(4-Fluoro-2-methyl)phenyl]-6-phenylmethoxy-1-{4-[(2-piperidyl)ethoxy]benzyl}-1,2,3,4-tetrahydroisoquinoline The title compound was prepared as described in Example 3.D from 2-[(4-fluoro-2-methyl)phenyl]-6-phenylmethoxy-1-(4-hydroxybenzyl)-1,2,3,4-tetrahydroisoquinoline (0.124 g, 0.27 mmol) to provide the title compound (0.12 g, 80% yield): ES-MS (m/z) 565 [M+H]+.

G. 2-[(4-Fluoro-2-methyl)phenyl]-1-1-{4-[(2-piperidyl)ethoxy]benzyl}-1,2,3,4-tetrahydroisoquinolin-6-ol The title compound was prepared as described in Example 14.D using 2-[(4-fluoro-2-methyl]phenyl)-6-phenylmethoxy-1-{4-[(2-piperidyl)ethoxy]benzyl}-1,2,3,4-tetrahydroisoquinoline (0.12 g, 0.2 mol) to provide the title compound (0.1 g, 77% yield): ES-MS (m/z) 475 [M+H]+.

Example 36

SYNTHESIS OF 1-{4-[(2-PIPERIDYL)ETHOXY]BENZYL}-2-[(4-TRIFLUOROMETHYL)PHENYL]-1,2,3,4-TETRAHYDROISOQUINOLIN-6-OL

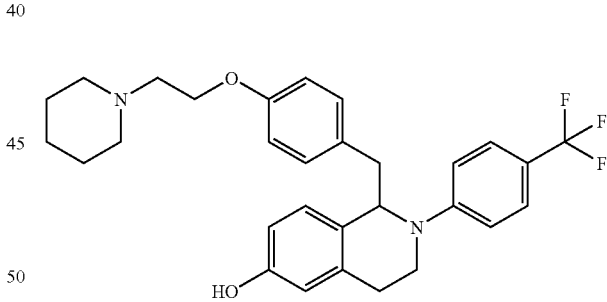

A. 2-(3-Hydroxyphenyl)-N-[4-(trifluoromethyl)phenyl]acetamide

The title compound was prepared as described in Example 34.B, using 4-(trifluoromethyl)aniline (1.61 g, 10.0 mmol) to provide the title compound (2.67 g, 90% yield): ES-MS (m/z) 296 [M+H]+.

B. 2-[3-(Phenylmethoxy)phenyl]-N-[4-(trifluoromethyl)phenyl]acetamide

The title compound was prepared as described in Example 34.C, using 2-(3-hydroxyphenyl)-N-[4-(trifluoromethyl)phenyl]acetamide (2.10 g, 7.11 mmol) to provide the title compound (2.104 g, 77% yield): $^1$H NMR (CDCl$_3$) 7.52 (s, 5H), 7.31-7.44 (m, 5H), 7.23 (br, 1H), 6.95 (m, 3H), 5.09 (s, 2H), 3.73 (s, 2H); ES-MS (m/z) 386 [M+H]$^+$.

C. {2-[3-(Phenylmethoxy)phenyl]ethyl}[4-(trifluoromethyl)phenyl]amine

The title compound was prepared as described in Example 34.D, using 2-[3-(phenylmethoxy)phenyl]-N-[4-(trifluoromethyl)phenyl]acetamide (2.0 g, 5.19 mmol) to provide the title compound (1.745 g, 91% yield): $^1$H NMR (CDCl$_3$) 7.33-7.45 (m, 6H), 7.23-7.28 (m, 1H), 6.81-6.88 (m, 3H), 6.59 (d, 2H), 5.06 (s, 2H), 4.00 (t, 1H), 4.42 (m, 2H), 2.89 (t, 2H); ES-MS (m/z) 372 [M+H]$^+$.

D. 6-(Phenylmethoxy)-1-{4-[(2-piperidyl)ethoxy]benzyl}-2-[4-(trifluoromethyl)phenyl]-1,2,3,4-tetrahydroisoquinoline The title compound was prepared as described in Example 34.E, using {2-[3-(phenylmethoxy)phenyl]ethyl}[4-(trifluoromethyl)phenyl]amine (0.55 g, 1.48 mmol) to provide the title compound (0.317 g, 36% yield): $^1$H NMR (CDCl$_3$) 7.40-7.45 (m, 6H), 6.71-6.88 (m, 9H), 6.63 (dd, 1H), 5.04 (s, 2H), 4.83 (t, 1H), 4.83 (m, 3H), 3.60 (m, 1H), 3.49 (m, 1H), 3.13 (dd, 1H), 2.91 (m, 1H), 2.74 (m and t, 3H), 2.51 (m, 4H), 1.61 (m, 4H), 1.45 (m, 2H); ES-MS (m/z) 601 [M+H]$^+$.

E. 1-{4-[(2-Piperidyl)ethoxy]benzyl}-2-[4-(trifluoromethyl)phenyl]-1,2,3,4-tetrahydroisoquinolin-6-ol The title compound was prepared as described in Example 14.D, using 6-(phenylmethoxy)-1-{4-[(2-piperidyl)ethoxy]benzyl}-2-[4-(trifluoromethyl)phenyl]-1,2,3,4-tetrahydroisoquinoline (0.30 g, 0.5 mmol) to provide the title compound (0.231 g, 91% yield): $^1$H NMR (CDCl$_3$) 7.45 (d, 2H), 6.81 (m, 4H), 6.51-6.73 (m, 6H), 4.79 (dd, 1H), 4.08 (t, 2H), 3.56 (m, 1H), 3.43 (m, 1H), 3.09 (dd, 1H), 2.77-2.94 (m, 4H), 2.66 (m, 1H), 2.61 (m, 4H), 1.64 (m, 4H), 1.46 (m, 2H); ES-MS (m/z) 511 [M+H]$^+$.

Example 37

SYNTHESIS OF 2-(4-CHLOROPHENYL)-1-BENZYL-1,2,3,4-TETRAHYDROISOQUINOLIN-6-OL

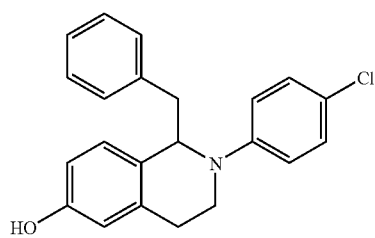

A. 3-[2-[(4-Chlorophenyl)amino]ethyl]phenol

The title compound was prepared as described in Example 34.D, using N-(4-chlorophenyl)-2-(3-hydroxyphenyl)acetamide (2.0 g, 7.64 mmol) to provide the title compound (1.569 g, 83% yield): $^1$H NMR (CDCl$_3$) 7.19 (dd, 1H), 7.10-7.14 (m, 2H), 6.78 (m, 1H), 6.69-6.73 (m, 2H), 6.50-6.55 (m, 2H), 3.66 (br, 1H), 3.36 (t, 2H), 2.86 (t, 2H), 2.05 (s, 1H); ES-MS (m/z) 248 [M+H]$^+$.

B. 2-(4-Chlorophenyl)-1-benzyl-1,2,3,4-tetrahydroisoquinolin-6-ol

To a solution of 3-{2-[(4-chlorophenyl)amino]ethyl}phenol (0.20 g, 0.8 mmol) and phenylacetaldehyde (0.194 g, 1.6 mmol) in CH$_2$Cl$_2$ (6 mL) was added trifluoroacetic acid (0.148 g, 1.6 mmol). After stirring at room temperature overnight, the reaction was quenched with saturated sodium bicarbonate and extracted with CH$_2$Cl$_2$. The organic layer was dried over MgSO$_4$, filtered, and concentrated. The residue was purified by chromatography (SiO$_2$, 15-30% ethyl acetate/hexane) to provide the title compound (0.203 g, 72% yield): $^1$H NMR (CDCl$_3$) 7.19-7.24 (m, 4H), 7.16 (m, 1H), 7.14 (m, 1H), 6.70 (m, 2H), 6.71 (m, 2H), 6.61 (m, 2H), 6.54 (dd, 1H), 4.77 (t, 1H), 3.58 (ddd, 1H), 3.47 (ddd, 1H), 3.17 (dd, 1H), 2.86-2.99 (m, 2H), 2.67 (m, 1H); ES-MS (m/z) 350 [M+H]$^+$.

Example 38

SYNTHESIS OF 2-(3-FLUOROPHENYL)-1-{4-[(2- PIPERIDY)ETHOXY]BENZYL}-1,2,3,4-TETRAHYDROISOQUINOLIN-6-OL

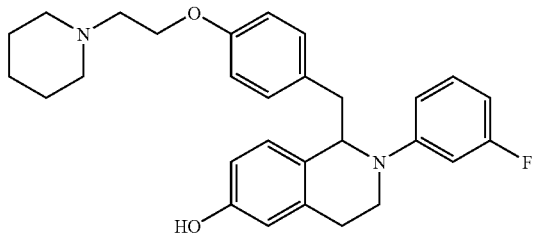

A. N-(3-Fluorophenyl)-2-(3-hydroxyphenyl)acetamide

The title compound was prepared as described in Example 34.B, using 3-fluoroaniline (1.11 g, 10.0 mmol) to provide the title compound (2.339 g, 95% yield): $^1$H NMR (CDCl$_3$) 7.42 (dt, 1H), 7.30 (d, 1H), 7.21 (dd, 1H), 7.12 (br, 1H), 7.02 (dd, 1H), 6.89 (d, 1H), 6.77-6.83 (m, 3H), 5.09 (s, 1H), 3.69 (s, 2H); ES-MS (m/z) 246 [M+H]$^+$.

B. N-(3-Fluorophenyl)-2-[3-(phenylmethoxy)phenyl]acetamide

The title compound was prepared as described in Example 34.C, N-(3-fluorophenyl)-2-(3-hydroxyphenyl)acetamide (2.20 g, 8.97 mmol) to provide the title compound (2.639 g, 88% yield): ES-MS (m/z) 336 [M+H]$^+$.

C. (3-Fluorophenyl){2-[3-(phenylmethoxy)phenyl]ethyl}amine

The title compound was prepared as described in Example 34.D, using N-(3-fluorophenyl)-2-[3-(phenylmethoxy)phenyl]acetamide (2.50 g, 7.45 mmol) to provide the title compound (1.441 g, 60% yield): ES-MS (m/z) 322 [M+H]$^+$.

D. 2-(3-Fluorophenyl)-6-(phenylmethoxy)-1-{4-[(2-piperidyl)ethoxy]benzyl}-1,2,3,4-tetrahydroisoquinoline The title compound was prepared as described in Example 34.E, using (3-fluorophenyl){2-[3-(phenylmethoxy)phenyl]

ethyl}amine (0.642 g, 2.0 mmol) to provide the title compound (0.297 g, 27% yield): ES-MS (m/z) 551 [M+H]+.

E. 2-(3-Fluorophenyl)-1-{4-[(2-piperidyl)ethoxy]benzyl}-1,2,3,4-tetrahydroisoquinolin-6-ol The title compound was prepared as described in Example 14.D, using 2-(3-fluorophenyl)-6-(phenylmethoxy)-1-{4-[(2-piperidyl)ethoxy]benzyl}-1,2,3,4-tetrahydroisoquinoline (0.29 g, 0.53 mmol) to provide the title compound (0.187 g, 77% yield): ): $^1$H NMR (CDCl$_3$) 7.18 (dd, 1H), 6.83 (m, 2H), 6.72 (d, 2H), 6.37-6.66 (m, 7H), 4.72 (dd, 1H), 4.10 (t, 2H), 3.39-3.70 (m, 3H), 3.11 (dd, 1H), 2.80-2.92 (m, 4H), 2.60-2.70 (m, 4H), 1.66 (m, 4H), 1.48 (m, 2H); ES-MS (m/z) 461 [M+H]+.

Example 39

SYNTHESIS OF 2-(4-METHOXYPHENYL)-1-{4-[(2-PIPERIDYL)ETHOXY]BENZYL}-1,2,3,4-TETRAHYDROISOQUINOLIN-6-OL

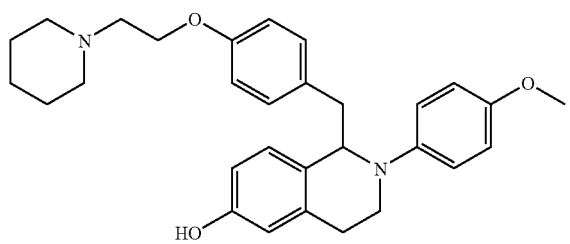

A. 2-(3-Hydroxyphenyl)-N-(4-methoxyphenyl) acetamide

The title compound was prepared as described in Example 34.B, using p-anisidine (1.23 g, 10.0 mmol) to provide the title compound (2.307 g, 90% yield): $^1$H NMR (CDCl$_3$) 7.32 (d, 1H), 7.30 (s, 1H), 6.98 (br, 1H), 6.94 (d, 1H), 6.81 (m, 5H). 5.14 (s, 1H), 3.71 (s, 3H), 3.68 (s, 2H); ES-MS (m/z) 258 [M+H]+.

B. N-(4-Methoxyphenyl)-2-[3-(phenylmethoxy)phenyl]acetamide

The title compound was prepared as described in Example 34.C, using 2-(3-hydroxyphenyl)-N-(4-methoxyphenyl)acetamide (2.20 g, 8.55 mmol) to provide the title compound (2.485 g, 84% yield): ES-MS (m/z) 348 [M+H]+.

C. (4-Methoxyphenyl){2-[3-(phenylmethoxy)phenyl]ethyl}amine

The title compound was prepared as described in Example 34.D, using N-(4-methoxyphenyl)-2-[3-(phenylmethoxy)phenyl]acetamide (2.1 g, 6.04 mmol) to provide the title compound (1.237 g, 61% yield): ES-MS (m/z) 334 [M+H]+.

D. 2-(4-Methoxyphenyl)-6-(phenylmethoxy)-1-{4-[(2-piperidyl)ethoxy]benzyl}-1,2,3,4-tetrahydroisoquinoline The title compound was prepared as described in Example 34.E, using (4-methoxyphenyl){2-[3-(phenylmethoxy)phenyl]ethyl}amine (0.666 g, 2.0 mmol) to provide the title compound (0.311 g, 28% yield): ES-MS (m/z) 563 [M+H]+.

E. 2-(4-Methoxyphenyl)-1-{4-[(2-piperidyl)ethoxy]benzyl}-1,2,3,4-tetrahydroisoquinolin-6-ol The title compound was prepared as described in Example 14.D, using 2-(4-methoxyphenyl)-6-(phenylmethoxy)-1-{4-[(2-piperidyl)ethoxy]benzyl}-1,2,3,4-tetrahydroisoquinoline (0.31 g, 0.55 mmol) to provide the title compound (0.238 g, 92% yield): ): $^1$H NMR (CDCl$_3$) 6.81-6.89 (m, 6H), 6.69 (m, 2H), 6.61 (m, 2H), 6.51 (m, 2H), 4.64 (t, 1H), 4.15 (t, 2H), 3.75 (s, 3H), 3.39-3.56 (m, 4H), 3.01-3.13 (t and m, 3H), 2.81 (m, 4H), 2.62 (m, 1H), 1.74 (m, 4H), 1.52 (m, 2H); ES-MS (m/z) 473 [M+H]+.

Example 40

SYNTHESIS OF 2-(4-FLUOROPHENYL)-6-METHOXY-1-{3-METHYL-4-[(2-PIPERIDYL)ETHOXY]BENZYL}-1,2,3,4-TETRAHYDROISOQUINOLINE

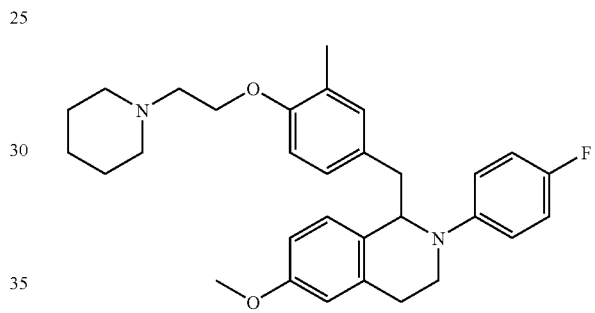

A. 4-Hydroxy-3-methyl-phenylacetic acid

To a solution of 3-methyl-4-methoxyphenylacetic acid (2.3 g., 12.8 mmol) in anh CH$_2$Cl$_2$, cooled to 0° C., was added 15 ml of a solution of BBr$_3$ (1.0 M in CH$_2$Cl$_2$) via syringe. After addition was complete, the reaction was allowed to warm to room temperature and then quenched with 5 ml water. The CH$_2$Cl$_2$ was removed and the residue was extracted with ethyl acetate. The organic layer was dried over MgSO$_4$, filtered and concentrated to yield the title compound (1.58 g, 75% yield): ES-MS (m/z) 167 [M+H]+.

B. N-(4-Fluorophenyl)-2-(4-hydroxy-3-methylphenyl)-N-{2-[3-methoxyphenyl]ethyl}acetamide The title compound was prepared as described in Example 34.B using 4-hydroxy-3-methylphenylacetic acid (1.5 g, 9 mmol) to provide the title compound (2 g, 84% yield): ES-MS (m/z) 394 [M+H]+.

C. 2-(4-Fluorophenyl)-1-(4-hydroxy-3-methylbenzyl)-6-methoxy-1,2,3,4-tetrahydroisoquinoline The title compound was prepared as described in Example 34.E using N-(4-fluorophenyl)-2-(4-hydroxy-3-methylphenyl)-N-{2-[3-methoxyphenyl]ethyl}acetamide (2 g, 6 mmol) to provide the title compound (0.4 g, 18% yield): ES-MS (m/z) 378 [M+H]+.

D. 2-(4-Fluorophenyl)-6-methoxy-1-{3-methyl-4-[(2-piperidyl)ethoxy]benzyl}-1,2,3,4-tetrahydroisoquinoline The title compound was prepared as described in Example 3.D using 2-(4-fluorophenyl)-1-(4-hydroxy-3-methylbenzyl)-6-methoxy-1,2,3,4-tetrahydroisoquinoline (0.4 g, 1 mmol) to provide the title compound (0.515 g, 99% yield): ES-MS (m/z) 489 [M+H]$^+$.

Example 41

SYNTHESIS OF 2-(4-FLUOROPHENYL)-1-{3-METHYL-4-[(2-PIPERIDYL)ETHOXY]BENZYL}-1,2,3,4-TETRAHYDROISOQUINOLIN-6-OL

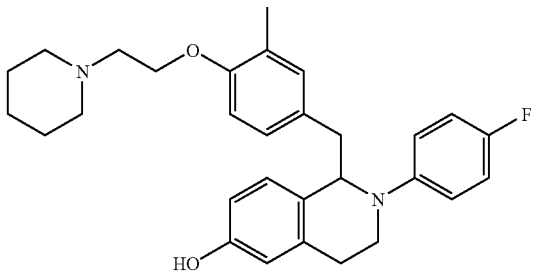

The title compound was prepared as described in Example 2 using 2-(4-fluorophenyl)-6-methoxy-1-{3-methyl-4-[(2-piperidyl)ethoxy]benzyl}-1,2,3,4-tetrahydroisoquinoline (0.5 g, 1 mmol) to provide the title compound (0.14 g, 30% yield): ES-MS (m/z) 475 [M+H]$^+$.

Example 42

SYNTHESIS OF 2-(2-PHENYLETHYL)-1-{4-[2-PIPERIDYL)ETHOXY]BENZYL}-1,2,3,4-TETRAHYDROISOQUINOLIN-6-OL

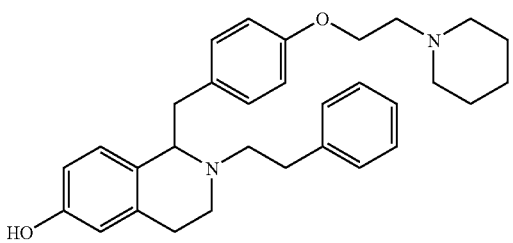

A. 2-[3-(Phenylmethoxy)phenyl]ethylamine

A solution of 3-benzyloxyphenylacetonitrile (11.50 g, 51.50 mmol) in 100 mL of THF at 0° C. was treated with LiAlH$_4$ (3.90 g, 103 mmol) in several portions over 20 minutes. The reaction mixture was warmed to room temperature and stirred for 30 minutes then it was heated at reflux for 6 h. The suspension was cooled to room temperature and quenched by the slow addition of Na$_2$SO$_4$.10H$_2$O (25 g). The resulting mixture was diluted with 200 mL of CH$_2$Cl$_2$. The organic layer was separated and the remaining salt was rinsed with additional CH$_2$Cl$_2$ (2×50 mL). The combined organic layers were dried over MgSO$_4$, concentrated, and purified by column chromatography (SiO$_2$, hexanes/ethyl acetate, 2:1) to provide the title compound (5.85 g, 51% yield): ES-MS (m/z) 228 [M+H]$^+$.

B. 6-Methoxy-2-(2-phenylethyl)-1-[4-(phenylmethoxy)benzyl-]-1,2,3,4-tetrahydroisoquinoline The title compound was prepared as described in Example 14.C, using 2-[3-(phenylmethoxy)phenyl]ethylamine (6.4 g, 1.11 mmol) to yield the title compound (0.39 g, 76% yield).

C. 6-Methoxy-2-(2-phenylethyl)-2-(4-hydroxyphenyl)-1,2,3,4-tetrahydroisoquinoline A solution of 6-methoxy-2-(2-phenylethyl)-1-[4-(phenylmethoxy)benzyl]-1,2,3,4-tetrahydroisoquinoline (0.3 g, 0.67 mol) in a 1:1 mixture of THF and ethanol was placed under a nitrogen atmosphere. To the flask was added the palladium (10% wt. on activated carbon, 0.100 g). The flask was evacuated, and the mixture placed under a hydrogen atmosphere. After stirring for five hours the reaction was filtered through celite then concentrated to yield the title compound (0.05 g, 20% yield): ES-MS (m/z) 374 [M+H]$^+$.

D. 2-(2-Phenylethyl)-1-{4-[(2-piperidyl)ethoxy]benzyl}-1,2,3,4-tetrahydroisoquinolin-6-ol 6-Methoxy-2-(2-phenylethyl)-1{[4-(2-piperidylethoxy)phenyl]methyl}-1,2,3,4-tetrahydroisoquinoline was prepared as described in Example 14.E, using 6-methoxy-2-(2-phenylethyl)-2-(4-hydroxyphenyl)-1,2,3,4-tetrahydroisoquinoline (0.05 g, 0.13 mmol). The title compound was prepared as described in Example 14.F, using 6-methoxy-2-(2-phenylethyl)-1{[4-(2-piperidylethoxy)phenyl]methyl}-1,2,3,4-tetrahydroisoquinoline (0.068 g, 0.14 mmol) to yield the title compound (0.015 g, 22.8% yield): $^1$H NMR (CDCl$_3$) 6.4-7.3 (m, 12H), 4-4.2 (m, 1H), 2.7-2.9 (m, 10H), 2.4-2.7 (m, 6H), 1.5-1.7 (m, 1H), 1.4-1.5 (m, 2H), 1.2 (m, 2H).

Example 43

SYNTHESIS OF 2-(4-CHLOROPHENYL)-1-{4-[(2-PIPERIDYL)ETHOXY]BENZYL}-1,2,3,4-TETRAHYDROISOQUINOLIN-6-OL

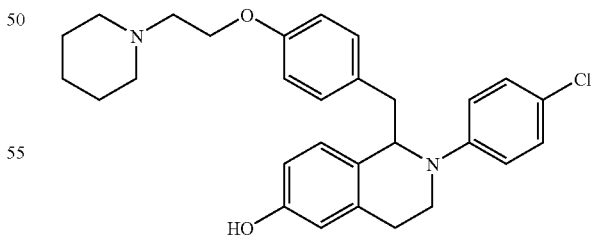

A. N-(4-Chlorophenyl)-2-(3-hydroxyphenyl)acetamide

The title compound was prepared as described in Example 34.B, using 4-chloroaniline (1.28 g, 10.0 mmol) to provide the title compound (2.361 g, 90% yield): ES-MS (m/z) 262 [M+H]$^+$.

B. N-(4-Chlorophenyl)-2-[3-(phenylmethoxy)phenyl]acetamide

The title compound was prepared as described in Example 34.C, using N-(4-chlorophenyl)-2-(3-hydroxyphenyl)acetamide (2.36 g, 9.0 mmol) to provide the title compound (2.517 g, 80% yield): $^1$H NMR (CDCl$_3$) 7.30-7.44 (m, 7H), 7.24 (m, 3H), 7.04 (br, 1H), 6.93 (m, 3H), 5.09 (s, 2H), 3.70 (s, 2H); ES-MS (m/z) 352 [M+H]$^+$.

C. (4-Chlorophenyl){2-[3-(phenylmethoxy)phenyl]ethyl}amine

The title compound was prepared as described in Example 34.D, using N-(4-chlorophenyl)-2-[3-(phenylmethoxy)phenyl]acetamide (1.8 g, 5.1 mmol) to provide the title compound (1.251 g, 73% yield): ES-MS (m/z) 338 [M+H]$^+$.

D. 2-(4-Chlorophenyl)-6-(phenylmethoxy)-1-{4-[(2-piperidyl)ethoxy]benzyl}-1,2,3,4-tetrahydroisoquinoline The title compound was prepared as described in Example 34.E, using (4-chlorophenyl){2-[3-(phenylmethoxy)phenyl]ethyl}amine (0.60 g, 1.78 mmol) to provide the title compound (0.283 g, 28% yield): $^1$H NMR (CDCl$_3$) 7.32-7.44 (m, 5H), 7.15 (d, 2H), 6.87 (d, 2H), 6.69-6.77 (m, 7H), 5.02 (s, 2H), 4.73 (t, 1H), 4.07 (t, 2H), 3.56 (m, 1H), 3.45 (m, 1H), 3.10 (dd, 1H), 2.91 (m, 2H), 2.76 (t, 2H), 2.74 (m, 1H), 2.51 (m, 4H), 1.61 (m, 4H), 1.46 (m, 2H); ES-MS (m/z) 567 [M+H]$^+$.

E. 2-(4-Chlorophenyl)-1-{4-[(2-piperidyl)ethoxy]benzyl}-1,2,3,4-tetrahydroisoquinolin-6-ol The title compound was prepared as described in Example 14.D, using 2-(4-chlorophenyl)-6-(phenylmethoxy)-1-{4-[(2-piperidyl)ethoxy]benzyl}-1,2,3,4-tetrahydroisoquinoline (0.27 g, 0.47 mmol) to provide the title compound (0.98 g, 41% yield): ): $^1$H NMR (CDCl$_3$) 7.18 (dd, 1H), 6.83 (m, 2H), 6.72 (d, 2H), 6.37-6.66 (m, 7H), 4.70 (t, 1H), 4.32 (t, 2H), 3.72 (m, 3H), 3.42-3.60 (m, 2H), 2.80-2.92 (m, 3H), 2.77-2.87 (m, 3H), 2.65 (m, 1H), 1.87-2.05 (m, 6H); ES-MS (m/z) 477 [M+H]$^+$.

Example 44

SYNTHESIS OF 2-(3,4-DICHLOROPHENYL)-1-{4-[(2-PIPERIDYL)ETHOXY]BENZYL}-1,2,3,4-TETRAHYDROISOQUINOLIN-6-OL

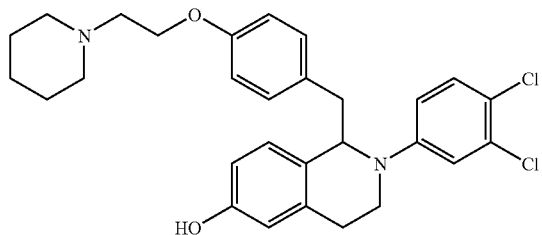

A. N-(3,4-Dichlorophenyl)-2-(3-hydroxyphenyl)acetamide

To a solution of 3-hydroxyphenyl acetic acid (5.0 g, 0.03 mol) in DMF (50 ml) was added 1-hydroxybenzotriazole hydrate (4.86 g, 0.03 mol) and 1-[3-(dimethylamino)propyl]-3-ethylcarbodiimide hydrochloride (6.9 g, 0.036 mol). To the flask was added 3,4-dichloroaniline (4.86 g, 0.03 mol). The reaction was allowed to stir overnight. Solvent was removed and the reaction was diluted with ethyl acetate. The reaction mixture was washed with 1N HCl, 10% sodium carbonate solution, and brine. The organic layer was dried over MgSO$_4$, filtered and concentrated to provide the title compound (5.5 g, 62% yield): ES-MS (m/z) 296 [M+H]$^+$.

B. N-(3,4-Dichlorophenyl)-2-[3-(phenylmethoxy)phenyl]acetamide

To a solution of N-(3,4-dichlorophenyl)-2-(3-hydroxyphenyl)acetamide (5.5 g, 0.019 mol) in DMF (25 ml) was added potassium carbonate powder (3.93 g, 0.028 mol). To the flask was added benzyl bromide (2.37 ml, 0.021 mol). The reaction was allowed to stir overnight. Solvent was removed and the reaction was diluted with ethyl acetate. The organic layer was washed with water, dried over MgSO$_4$, filtered and concentrated. The crude product was triturated with ether and hexanes to provide the title compound (4.65 g, 64% yield): ES-MS (m/z) 386 [M+H]$^+$.

C. (3,4-Dichlorophenyl){2-[3-(phenylmethoxy)phenyl]ethyl}amine

To a solution of N-(3,4-dichlorophenyl)-2-[3-(phenylmethoxy)phenyl]acetamide (4.5 g, 0.012 mmol) in THF (20 ml) on ice was added the borane-tetrahydrofuran complex (15 ml, 0.023 mol). The reaction was allowed to reflux at 80° C. for six hours. The reduction reaction was placed on ice, acidified using 4 N HCl, then stirred for twenty minutes. The reaction was then basified with an aqueous solution of potassium hydroxide. The reaction was diluted with water and extracted with ethyl acetate. The organic layer was washed with brine, dried over MgSO$_4$, filtered and concentrated to provide the title compound (4.3 g, 99% yield): ES-MS (m/z) 372 [M+H]$^+$.

D. N-(3,4-Dichlorophenyl)-2-(4-hydroxyphenyl)-N-{2-[3-(phenylmethoxy)phenyl]ethyl}acetamide To a solution of (3,4-dichlorophenyl){2-[3-(phenylmethoxy)phenyl]ethyl}amine (4.32 g, 0.011 mol) in chlorobenzene (40 ml) was added 4-hydroxy phenyl acetic acid (2.43 g, 0.014 mol), followed by phosphorus trichloride (5 ml, 0.005 mol). The reaction was allowed to reflux at 135° C. overnight. Solvent was removed and the reaction was basified with 10% sodium hydroxide solution. The reaction was diluted with ethyl acetate and water. The organic was washed with brine, dried with MgSO$_4$, filtered, and concentrated to provide the title compound (5.5 g, 99% yield): ES-MS (m/z) 506 [M+H]$^+$.

E. 2-(3,4-Dichlorophenyl)-1-(4-hydroxybenzyl)-6-(phenylmethoxy)-1,2,3,4-tetrahydroisoquinoline To a solution of N-(3,4-dichlorophenyl)-2-(4-hydroxyphenyl)-N-(2-[3-(phenylmethoxy)phenyl]ethylacetamide (7.6 g, 0.015 mol) in acetonitrile (30 ml) was added phosphorus oxychloride (4.19 ml, 0.045 mol). The reaction was allowed to reflux at 80° C. for 6 hours. Solvent was removed and the reaction was placed on ice. To the flask was added ice and water. The reaction was extracted with ethyl acetate. The organic layer was washed with brine, dried over MgSO$_4$, filtered, concentrated, and then dissolved in methanol. To the flask was added small aliquots of sodium borohydride (1.02 g, 0.027 mol). The reaction was allowed to stir overnight. The solvent was removed and the reaction was diluted with dichloromethane and water. The organic layer was separated and the aqueous layer was extracted with additional dichloromethane. The organic layers were combined, washed with brine, dried over MgSO$_4$, filtered and concentrated to provide the title compound (0.5 g, 6.8% yield): ES-MS (m/z) 490 [M+H]$^+$.

F. 2-(3,4-Dichlorophenyl)-6-(phenylmethoxy)-1-{4-[2-piperidyl)ethoxy]benzyl}-1,2,3,4-tetrahydroisoquinoline To a solution of 2-(3,4-dichlorophenyl)-1-(4-hydroxybenzyl)-6-(phenylmethoxy)-1,2,3,4-tetrahydroisoquinoline (0.5 g, 0.001 mol) in DMF (3 ml) was added potassium carbonate (0.2 g, 0.0015 mol). The reaction was allowed to stir for twenty minutes. To the flask was added 1-(2-chloroethyl) piperidine monohyrdochloride (0.22 g, 0.0012 mol) The reaction was allowed to stir at 80° C. overnight. Solvent was removed. The reaction was diluted with ethyl acetate and water. The aqueous layer was extracted with ethyl acetate. The organic layers were combined, washed with brine, dried over MgSO$_4$, filtered and concentrated to yield the title compound (0.42 g, 70% yield): ES-MS (m/z) 601 [M+H]$^+$.

G. 2-(3,4-Dichlorophenyl)-1-{4-[(2-piperidyl)ethoxy]benzyl}-1,2,3,4-tetrahydroisoquinolin-6-ol A solution of 2-(3,4-dichlorophenyl)-6-(phenylmethoxy)-1-{4-[(2-piperidyl)ethoxy]benzyl}-1,2,3,4-tetrahydroisoquinoline (0.380 g, 0.63 mmol) was placed under a nitrogen atmosphere and dissolved in ethyl acetate (5 ml). The flask was evacuated and flushed with nitrogen. To the flask was added palladium (10% wt. on activated carbon, 0.190 g). The flask was flushed and evacuated with nitrogen followed by hydrogen. The reaction was allowed to stir under the hydrogen atmosphere at room temperature for 5 hours. The reaction mixture was filtered through celite and concentrated. The product was purified by preparative HLPC (C-18 column, 10-100% acetonitrile/water with 0.1% trifluoroacetic acid) to provide the title compound (0.010 g, 3% yield). $^1$H NMR (CDCl$_3$) 6.7-7.2 (m, 10H), 4.7 (t, 1H), 4.2-4.4 (m, 2H), 3.6-4.0 (m, 4H), 3.3-3.6 (m, 3H), 3.0-3.1 (m, 1H), 2.7-2.9 (m, 3H), 2.6-2.7 (m, 1H), 1.8-2.1 (m, 4H), 1.4 (m, 2H); ES-MS (m/z) 511 [M+H]$^+$.

Example 45

SYNTHESIS OF 2-(4-FLUOROPHENYL)-1-{4-[(2-PIPERIDYL)ETHOXY]PHENETHYL}-1,2,3,4-TETRAHYDROISOQUINOLIN-6-OL

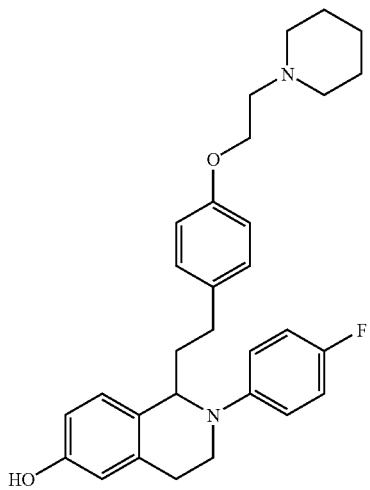

A. N-(4-Fluorophenyl)-3-(4-hydroxyphenyl)-N-{2-[3-(phenylmethoxy)phenyl]ethyl}propanamide The title compound was prepared as described in Example 44.D using (4-fluorophenyl){2-[3-(phenylmethoxy)phenyl]ethyl}amine (1.4 g, 4.36 mmol) and 3-(4-hydroxyphenyl) propanoic acid (1.01 g, 6.11 mmol) to provide the title compound (1.82 g, 89% yield): ES-MS (m/z) 470 [M+H]$^+$.

B. 2-(4-Fluorophenyl)-1-(4-hydroxyphenethyl}-6-phenylmethoxy-1,2,3,4-tetrahydroisoquinoline The title compound was prepared as described in Example 14.B using N-(4-fluorophenyl)-3-(4-hydroxyphenyl)-N-{2-[3-(phenylmethoxy)phenyl]ethyl}-propanamide (1.81 g, 3.85 mmol) to provide the title compound (0.78 g, 45% yield): ES-MS (m/z) 454 [M+H]$^+$.

C. 2-(4-Fluorophenyl)-6-phenylmethoxy-1-{4-[(2-piperidyl)ethoxy]phenethyl}-1,2,3,4-tetrahydroisoquinoline The title compound was prepared as described in Example 3.D using 2-(4-fluorophenyl)-1-(4-hydroxyphenethyl)-6-phenylmethoxy-1,2,3,4-tetrahydroisoquinoline (0.76 g, 1.67 mmol) to provide the title compound (0.50 g, 53% yield: ES-MS (m/z) 565 [M+H]$^+$.

D. 2-(4-Fluorophenyl)-1-{4-[(2-piperidyl)ethoxy]phenethyl}-1,2,3,4-tetrahydroisoquinolin-6-ol The title compound was prepared as described in Example 14.D using 2-(4-fluorophenyl)-6-phenylmethoxy-1-{4-[(2-piperidyl)ethoxy]phenethyl}-1,2,3,4-tetrahydroisoquinoline (0.50 g, 0.89 mmol) to provide the title compound (0.172 g, 41% yield: ES-MS (m/z) 475 [M+H]$^+$.

Example 46

SYNTHESIS OF 2-(4-FLUOROPHENYL)-1-{4-(N-ACETYL)BENZYL}-1,2,3,4-TETRAHYDROISOQUINOLIN-6-OL

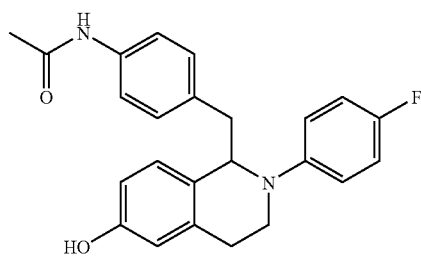

A. 2-(4-Fluorophenyl)-6-phenylmethoxy-1-{4-aminobenzyl}-1,2,3,4-tetrahydroisoquinoline A solution of 2-(4-fluorophenyl)6-phenylmethoxy-1-{4-nitrobenzyl}-1,2,3,4-tetrahydroisoquinoline (3 g, 6.4 mmol) and SnCl$_2$.H$_2$O (7.2 g, 32 mmol) in DMF was stirred at room temperature overnight. The solvent was removed and the residue was treated with ethyl acetate (200 ml) and water (200 ml). The organic layer was dried over MgSO$_4$, filtered and concentrated to provide the title compound (2.8 g, 100% yield): ES-MS (m/z) 439 [M+H]$^+$.

B. 2-(4-Fluorophenyl)-6-phenylmethoxy-1-[4-(N-acetyl)benzyl]-1,2,3,4-tetrahydroisoquinoline A solution of 2-(4-fluorophenyl)-6-phenylmethoxy-1-{4-aminobenzyl}-1,2,3,4-tetrahydroisoquinoline (0.56 g, 1.3 mmol), Ac$_2$O (3 ml) and pyridine (2.6 ml) were stirred at room temperature for 3 hours. The solvents were removed and the residue treated with water and ethyl acetate. The organic layer was dried over MgSO$_4$, filtered, concentrated and purified by column chromatography (SiO$_2$, ethyl acetate: hexanes, 2:3) to provide the title compound (0.39 g, 62% yield): ES-MS (m/z) 481 [M+H]$^+$.

C. 2-(4-Fluorophenyl)-1-{4-(N-acetyl)benzyl}-1,2,3,4-tetrahydroisoquinolin-6-ol The title compound was prepared as described in Example 14.D using 2-(4-fluorophenyl)-6-phenylmethoxy-1-{4-(N-acetyl)benzyl}-1,2,3,4-tetrahydroisoquinoline (0.39 g., 0.8 mmol) to provide the title compound (0.28 g, 88% yield): ES-MS (m/z) 390 [M+H]$^+$.

Example 47

SYNTHESIS OF 2-(4-FLUOROPHENYL)-1-(4-[2-(1-METHYL(2-PIPERIDYL))ETHOXY]BENZYL)-1,2,3,4-TETRAHYDROISOQUINOLIN-6-OL

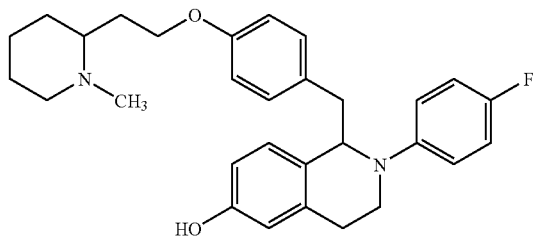

A. N-(4-Fluorophenyl)-2-(3-hydroxyphenyl)acetamide

The title compound was prepared as described in Example 44.A, using 3-hydroxyphenyl acetic acid (80 g, 0.52 mol) and 4-fluoroaniline (49.3 ml, 0.52 mol) to provide the title compound (113 g, 89% yield): ES-MS (m/z) 246 [M+H]$^+$.

B. N-(4-Fluorophenyl)-2-[3-(phenylmethoxy)phenyl]acetamide

The title compound was prepared as described in Example 44.B, using N-(4-fluorophenyl)-2-(3-hydroxyphenyl)acetamide (335 g, 1.36 mol) to provide the title compound (345 g, 75% yield): ES-MS (m/z) 336 [M+H]$^+$.

C. (4-Fluorophenyl){2-[3-(phenylmethoxy)phenyl]ethyl}amine

The title compound was prepared as described in Example 44.C, using N-(4-fluorophenyl)-2-[3-(phenylmethoxy)phenyl]acetamide (73.65 g, 0.22 mol) to provide the title compound (70.38 g, 99% yield): ES-MS (m/z) 322 [M+H]$^+$.

D. N-(4-Fluorophenyl)-2-(4-hydroxyphenyl)-N-{2-[3-(phenylmethoxy)phenyl]ethyl}acetamide The title compound was prepared as described in Example 44.D, using (4-fluorophenyl){2-[3-(phenylmethoxy)phenyl]ethyl}amine (62 g, 0.19 mol) to provide the title compound (86 g, 99% yield): ES-MS (m/z) 456 [M+H]$^+$.

E. 2-(4-Fluorophenyl)-1-(4-hydroxybenzyl)-6-(phenylmethoxy)-1,2,3,4-tetrahydroisoquinoline The title compound was prepared as described in Example 44.E, using N-(4-fluorophenyl)-2-(4-hydroxyphenyl)-N-{2-[3-(phenylmethoxy)phenyl]ethyl}acetamide (86.45 g, 0.19 mol) to yield the title compound (22 g, 26% yield): ES-MS (m/z) 440 [M+H]$^+$.

F. 2-(4-Fluorophenyl)-1-(4-[2-(1-methyl(2-piperidyl))ethoxy]benzyl)-6-(phenylmethoxy)-1,2,3,4-tetrahydroisoquinoline To a solution of 2-(4-fluorophenyl)-1-(4-hydroxybenzyl)-6-(phenylmethoxy)-1,2,3,4-tetrahydroisoquinoline (0.500 g, 1.14 mmol) in DMF (5 ml) was added potassium carbonate (0.236 g, 1.7 mmol) and the resulting mixture allowed to stir for twenty minutes. To the reaction mixture was added 2-(2-chloroethyl)-N-methyl piperidine (0.271 g, 1.37 mmol). The reaction was allowed to stir overnight. The reaction was diluted with water and extracted with ethyl acetate. The organic layer was washed with brine, dried over MgSO$_4$, filtered, and concentrated. The product was purified by radial chromatography (100% CH$_2$Cl$_2$, then CH$_2$Cl$_2$/MeOH, 95:5) to yield the title compound (0.043 g, 7% yield): ES-MS (m/z) 565 [M+H]$^+$.

G. 2-(4-Fluorophenyl)-1-(4-[2-(1-methyl(2-piperidyl))ethoxy]benzyl)-1,2,3,4-tetrahydroisoquinolin-6-ol The title compound was prepared as described in Example 44.G, using 2-(4-fluorophenyl)-1-(4-[2-(1-methyl(2-piperidyl))ethoxy]benzyl)-6-(phenylmethoxy)-1,2,3,4-tetrahydroisoquinoline (0.043 g, 0.076 mmol). The product was purified by radial chromatography (100% CH$_2$Cl$_2$, then CH$_2$Cl$_2$/MeOH, 95:5) to yield the title compound (0.005 g, 14% yield): ES-MS (m/z) 475 [M+H]$^+$.

Example 48

SYNTHESIS OF 2-(4-FLUOROPHENYL)-1-{2-[(2-PIPERIDYL)ETHOXY]BENZYL}-1,2,3,4-TETRAHYDROISOQUINOLIN-6-OL

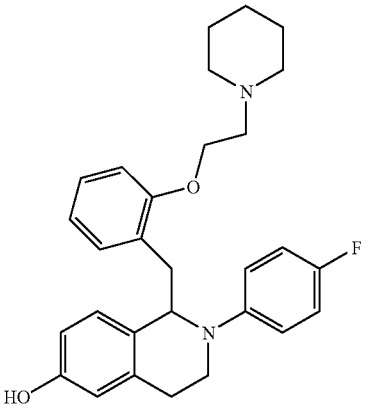

A. N-{2-(3-Methoxyphenyl)ethyl}-N-(4-fluorophenyl)-2-{2-(phenylmethoxy)phenyl}acetamide The title compound was prepared as described in Example 3.A using 2-benzyloxyphenylacetyl chloride (2.44 g, 10 mmol) to yield the title compound (4.44 g, 94% yield): ES-MS (m/z) 470[M+H]$^+$.

B. 1-[2-(Phenylmethoxy)benzyl]-6-methoxy-2-fluorophenyl-1,2,3,4-tetrahydroisoquinoline The title compound was prepared as described in Example 1.D using N-[2-(3-methoxyphenyl)ethyl]-N-(4-fluorophenyl)-2-{2-(phenylmethoxy)phenyl}acetamide (4.4 g, 9.4 mmol), bromoacetylbromide (0.33 g, 1.65 mmol) to provide the title compound (1.8 g, 42% yield): ES-MS (m/z) 454 [M+H]+.

C. 6-Methoxy-2-fluorophenyl-1-(2-hydroxybenzyl)-1,2,3,4-tetrahydroisoquinoline The title compound was prepared as described in Example 3.C using 1-[2-(phenylmethoxy)benzyl]-6-methoxy-2-fluorophenyl-1,2,3,4-tetrahydroisoquinoline (1.8 g, 4 mmol) to yield the title compound (1.37 g, 95% yield): ES-MS (m/z) 364 [M+H]+.

D. 6-Methoxy-2-fluorophenyl-1-{2-[(2-piperidyl)ethoxy]benzyl}-1,2,3,4-tetrahydroisoquinoline The title compound was prepared as described in Example 3.D using 6-methoxy-2-fluorophenyl-1-(2-hydroxybenzyl)-1,2,3,4-tetrahydroisoquinoline (1.37 g, 3.7 mmol) to provide the title compound (1.7 g, 95% yield): ES-MS (m/z) 475 [M+H]+.

E. 2-(4-Fluorophenyl)-1-{2-[(2-piperidyl)ethoxy]benzyl}-1,2,3,4-tetrahydroisoquinolin-6-ol The title compound was prepared as described in Example 2 using 6-methoxy-2-fluorophenyl-1-{2-[(2-piperidyl)ethoxy]benzyl}-1,2,3,4-tetrahydroisoquinoline (1.7 g, 3.5 mmol) to provide the title compound (0.112 g, 7% yield): ES-MS (m/z) 460[M+H]+.

Example 49

SYNTHESIS OF 2-(4-FLUOROPHENYL)-1-{4-(2-PIPERIDYLACETAMIDE)BENZYL}-1,2,3,4-TETRAHYDROISOQUINOLIN-6-OL

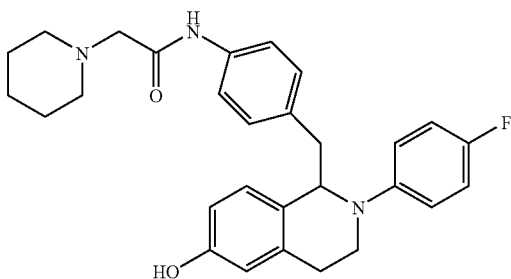

A. 2-(4-Fluorophenyl)-6-phenylmethoxy-1-{4-(2-Bromoacetamide)benzyl}-1,2,3,4-tetrahydroisoquinoline A solution of 2-{4-fluorophenyl}-6-phenylmethoxy-1-(4-aminobenzyl}-1,2,3,4-tetrahydroisoquinoline (0.65 g, 1.5 mmol), bromoacetylbromide (0.33 g, 1.65 mmol) and triethylamine (0.17 g, 1.65 mmol) in anh THF was stirred at room temperature overnight. Excess reagent was quenched by addition of water, and the reaction extracted with CH2Cl2.

The organic layer was dried over MgSO4 and concentrated to yield the title compound (0.83 g, 99% yield): ES-MS (m/z) 559/561 [M+H]+.

B. 2-(4-Fluorophenyl)-6-phenylmethoxy-1-[4-(2-piperidylacetamide)benzyl]-1,2,3,4-tetrahydroisoquinoline A mixture of 2-(4-fluorophenyl)-6-phenylmethoxy-1-[4-(2-bromoacetamide)benzyl]-1,2,3,4-tetrahydroisoquinoline (0.83 g, 1.5 mmol), piperidine (0.133 g, 1.6 mmol) and K2CO3 (0.25 g, 1.8 mmol) in CH2Cl2 was stirred at room temperature overnight. The reaction mixture was concentrated and purified by column chromatography (SiO2, CH2Cl2/MeOH, 12:1) to provide the title compound (0.2 g. 24% yield): ES-MS (m/z) 564 [M+H]+.

C. 2-(4-Fluorophenyl)-1-{4-(2-piperidylacetamide)benzyl}-1,2,3,4-tetrahydroisoquinolin-6-ol The title compound was prepared as described in Example 3.D using 2-(4-fluorophenyl)-6-phenylmethoxy-1-{4-(2-piperidylacetamide)benzyl}-1,2,3,4-tetrahydroisoquinoline (0.05 g, 0.09 mmol) to provide the title compound (0.04 g, 95% yield): ES-MS (m/z) 474 [M+H]+.

Example 50

SYNTHESIS OF 2-(4-FLUOROPHENYL)-1-[4-(1-METHYLPYRROLIDIN-3-YLOXY)BENZYL]-1,2,3,4-TETRAHYDROQUINOLIN-6-OL

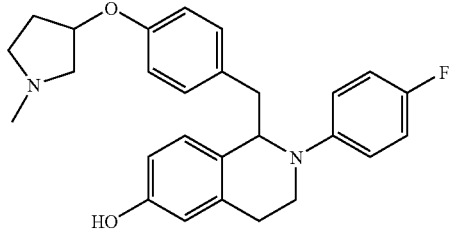

A. 2-(4-Fluorophenyl)-1-[4-(1-methylpyrrolidin-3-yloxy)benzyl]-6-(phenylmethoxy)-1,2,3,4-tetrahydroisoquinoline To a solution of 2-(4-fluorophenyl)-1-(4-hydroxybenzyl)-6-(phenylmethoxy)-1,2,3,4-tetrahydroisoquinoline (0.450 g, 1.02 mmol) in THF (5 ml) was added 1-methyl-3-pyrrolidinol (0.22 ml, 2.04 mmol), tri-n-butyl-phosphine (0.5 ml, 2.04 mmol) and 1,1' azodicarbonyl dipiperidine (0.5 g, 2.04 mmol) respectively. Dichloromethane (4 ml) was added and the reaction was allowed to stir overnight. The reaction was diluted with aqueous sodium bicarbonate and extracted with ethyl acetate. The organic layer was dried with MgSO4, filtered and concentrated. The product was purified by radial chromatography (100% CH2Cl2, then CH2Cl2/MeOH, 95:5) to yield the title compound (0.30 g, 56% yield): ES-MS (m/z) 523 [M+H]+.

B. 2-(4-Fluorophenyl)-1-[4-(1-methylpyrrolidin-3-yloxy)benzyl]-1,2,3,4-tetrahydroisoquinolin-6-ol The title compound was prepared as described in Example 44.G, using 2-(4-fluorophenyl)-1-[4-(1-methylpyrrolidin-3-yloxy)benzyl]-6-(phenylmethoxy)-1,2,3,4-tetrahydroisoquinoline (0.265 g, 0.5 mmol) to provide the title compound (0.005 g, 2% yield): ¹H NMR (CDCl₃) 6.7-7.2 (m, 11H), 5.1 (m, 1H), 4.9 (m, 1H), 3.7 (m, 2H), 3.0 (m, 6H), 2.4 (m, 2H), 1.4-1.7 (m, 5H); ES-MS (m/z) 433 [M+H]⁺.

Example 51

SYNTHESIS OF 2-(4-FLUOROPHENYL)-1-[4-(2-PIPERIDYLETHOXY)BENZYL]-6-1,2,3,4-TETRAHYDROISOQUINOLYL MELTHYLSULFONATE

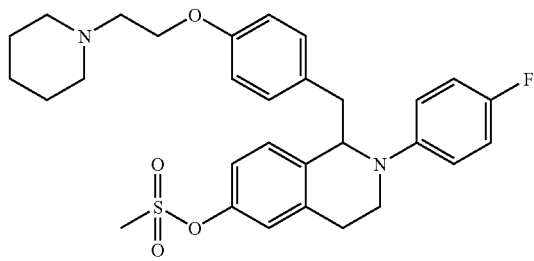

A. 2-(4-Fluorophenyl)-6-(phenylmethoxy)-1-{4-[(2-piperidyl)ethoxy]benzyl}-1,2,3,4-tetrahydroisoquinoline The title compound was prepared using the procedure described in Example 44.F, using 2-(4-fluorophenyl)-1-(4-hydroxybenzyl)-6-(phenylmethoxy)-1,2,3,4-tetrahydroisoquinoline (15.6 g, 0.036 mol) to provide the title compound (8.5 g, 43% yield): ES-MS (m/z) 551 [M+H]⁺.

B. 2-(4-Fluorophenyl)-1-{4-[(2-piperidyl)ethoxy]benzyl}-1,2,3,4-tetrahydroisoquinolin-6-ol The title compound was prepared using the procedure described in Example 44.G, using 2-(4-fluorophenyl)-6-(phenylmethoxy)-1-{4-[(2-piperidyl)ethoxy]benzyl}-1,2,3,4-tetrahydroisoquinoline (8.4 g, 0.018 mol) to provide the title compound (6.0 g, 87% yield): ES-MS (m/z) 461 [M+H]⁺.

C. 2-(4-Fluorophenyl)-1-[4-(2-piperidylethoxy)benzyl]-6-1,2,3,4-tetrahydroisoquinolyl methylsulfonate To a solution containing 2-(4-fluorophenyl)-1-{4-[(2-piperidyl)ethoxy]benzyl}-1,2,3,4-tetrahydroisoquinolin-6-ol (0.100 g, 0.2 mmol) in pyridine (0.4 ml) was added methyl sulfonyl chloride (25 μl, 0.32 mmol). After stirring for five hours, solvent was removed and the reaction was basified with aqueous sodium bicarbonate solution. The reaction was extracted with dichloromethane and concentrated. The product was purified by semipreparative HLPC (C-18 column, 10-100% acetonitrile/water with 0.1% trifluoroacetic acid). The acetonitrile was removed from the HPLC fractions containing the desired product. Ethyl acetate was added and the solution neutralized using saturated sodium bicarbonate. The organic layer was washed with brine, dried over MgSO₄, filtered and concentrated to provide the title compound (0.0135 g, 13% yield): ¹H NMR (CDCl₃) 6.7-7.1 (m, 11H), 4.78 (t, 1H), 4.1 (t, 3H), 3.45-3.62 (m, 2H), 2.62-3.18 (m, 8H), 2.58 (m, 4H), 1.63 (m, 4H), 1.43 (m, 2H); ES-MS (m/z) 539 [M+H]⁺.

Example 52

SYNTHESIS OF 2-(2,4-DICHLOROPHENYL)-1-{4-[(2-PIPERIDYL)ETHOXY]BENZYL}-1,2,3,4-TETRAHYDROISOQUINOLIN-6-OL

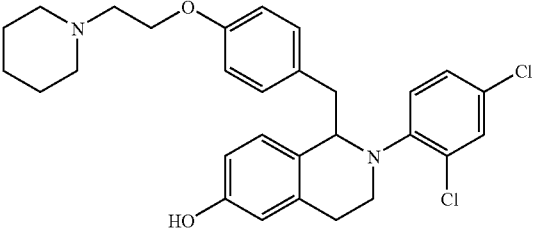

A. Phenylmethyl 2-[3-(phenylmethoxy)phenyl]acetate

To a solution of 3-hydroxyphenyl acetic acid (5.0 g, 0.03 mol) in DMF (25 ml) was added potassium carbonate (12.4 g, 0.09 mol). The reaction was allowed to stir for twenty minutes at which time benzyl bromide (8.9 ml, 0.075 mol) was added to the flask. The reaction was allowed to stir overnight. Solvent was removed. The reaction was diluted with water and extracted with ethyl acetate. The organic layer was washed with brine, dried over MgSO₄, filtered and concentrated to yield the title compound (9.9 g, 99% yield): ES-MS (m/z) 243 [M+H]⁺.

B. 2-[3-(Phenylmethoxy)phenyl]acetyl chloride

To a solution of phenylmethyl 2-[3-(phenylmethoxy)phenyl]acetate (9.97 g, 0.03 mol) in a 5:1 mixture of THF/water was added a solution of lithium hydroxide monohydrate (2.5 g, 0.06 mol) in water. The reaction was allowed to stir at 50° C. for 6 hours and then at room temperature overnight. Solvent was removed and the reaction was acidified with 4 N HCl solution while on ice. 2-[3-(Phenylmethoxy)phenyl]acetic acid precipitated from the solution and was collected by filtration. The 2-[3-(phenylmethoxy)phenyl]acetic acid (7.0 g, 0.03 mol) was dissolved in dichloromethane (100 ml) and a small amount of DMF (4 drops) was added. To the reaction was added oxalyl chloride (5.23 ml, 0.06 mol). The reaction was allowed to stir for 6 hours, and solvents were removed to yield the title compound (7.7 g, 99% yield): ES-MS (m/z) 386 [M+H]⁺.

C. N-(2,4-Dichlorophenyl)-2-[3-(phenylmethoxy)phenyl}acetamide

To a solution of 2,4-dichloroaniline (2.67 g, 0.0165 mol) in dichloromethane (20 ml) was slowly added a solution of 2-[3-(phenylmethoxy)phenyl]acetyl chloride (3.84 g, 0.015 mol) in dichloromethane (10 ml). After stirring for three hours, triethylamine (2 ml, 0.015 mol) was added to the reaction and the reaction was allowed to stir overnight. To the reaction was added an aqueous solution of sodium bicarbonate. The mixture was extracted with dichloromethane. The organic layer was washed with brine, dried over MgSO₄, filtered and concentrated. The solid was triturated with ether and hexane, then filtered to provide the title compound (4.0 g, 70% yield): ES-MS (m/z) 372 [M+H]⁺.

D. (2,4-Dichlorophenyl)-2-(4-hydroxyphenyl)-N-2 {2-[3-(phenylmethoxy)phenyl]ethyl}acetamide The title compound was prepared as described in Example 44.D, using N-(2,4-dichlorophenyl)-2-[3-(phenylmethoxy) phenyl]acetamide (4.0 g, 0.01 mol) to provide the title compound (3.72 g, 44% yield): ES-MS (m/z) 506 [M+H]$^+$.

E. 2-(2,4-Dichlorophenyl)-1-(4-hydroxybenzyl)-6-(phenylmethoxy)-1,2,3,4-tetrahydroisoquinoline The title compound was prepared as described in Example 44.E, using (2,4-dichlorophenyl)-2-(4-hydroxyphenyl)-N-2 {2-[3-(phenylmethoxy)phenyl]ethyl}acetamide (3.5 g, 0.009 mol) to provide the title compound (1.0 g, 22% yield): ES-MS (m/z) 490 [M+H]$^+$.

F. 2-(2,4-Dichlorophenyl)-6(phenylmethoxy)-1-{4-[(2-piperidyl)ethoxy}benzyl}-1,2,3,4-tetrahydroisoquinoline The title compound was prepared as described in Example 44.F, using 2-(2,4-dichlorophenyl)-1-(4-hydroxybenzyl)-6-(phenylmethoxy)-1,2,3,4-tetrahydroisoquinoline (0.96 g, 0.002 mol) to provide the title compound (1.2 g, 50% yield): ES-MS (m/z) 601 [M+H]$^+$.

G. 2-(2,4-Dichlorophenyl)-1-{4-[2-piperidyl)ethoxy]benzyl}-1,2,3,4-tetrahydroisoquinolin-6-ol The title compound was prepared as described in Example 44.G, using 2-(2,4-dichlorophenyl)-6-(phenylmethoxy)-1-{4-[(2-piperidyl)ethoxy]benzyl}-1,2,3,4-tetrahydroisoquinoline (0.60 g, 1 mmol) to provide the title compound (0.0083 g, 1.6% yield): 1H NMR (CDCl$_3$) 6.7-7.0 (m, 10H), 4.2 (t, 1H), 4.1 (t, 2H), 3.4-3.7 (m, 2H), 3.05 (m, 2H), 2.4-2.9 (m, 8H), 1.7 (m, 4H), 1.5 (m, 2H); ES-MS (m/z) 511 [M+H]$^+$.

Example 53

SYNTHESIS OF 2-(4-FLUOROPHENYL)-1-{[4-(2-PIPERIDYL)ETHOXY]BENZYL}-6-1,2,3,4-TETRAHYDROISOQUINOLYL AMINOSULFONATE

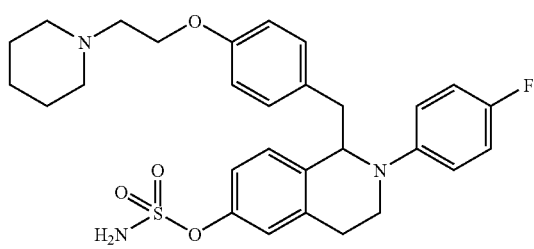

To a solution of chlorosulfonyl isocyanate (100 µl, 1.08 mmol) in toluene (2 ml) cooled in a dry ice/acetone bath was added formic acid (40 µl, 1.08 mmol). The reaction was allowed to stir at room temperature for three hours. The reaction yielded N-(chlorosulfonyl)carbamoyl formate in a tolulene solution. To a solution of 2-(4-fluorophenyl)-1-{4-[(2-piperidyl)ethoxy]benzyl}-1,2,3,4-tetrahydroisoquinolin-6-ol (0.100 g, 0.2 mmol) in pyridine was added the N-(chlorosulfonyl)carbamoyl formate solution in toluene (1.5 ml). The reaction was allowed to stir for three hours. The reaction was treated with an aqueous sodium bicarbonate solution and extracted with dichloromethane. The product was purified by HPLC (C-18 column, 10-100% acetonitrile/water with 0.1% trifluoroacetic acid) to yield the title compound (0.0083 g, 8% yield): 1H NMR (CDCl$_3$) 6.6-7.2 (m, 11H), 2.7-3.8 (m, 12H), 5.4 (broad s, 2H), 4.85 (t, 1H), 4.3 (m, 2H), 3.4-3.8 (m, 4H), 3.1 (m, 1H), 2.7-3.0 (m, 7H), 1.9 (m, 4H), 1.5 (m, 2H); ES-MS (m/z) 540 [M+H]$^+$.

Example 54

SYNTHESIS OF 2-(2-(4-FLUOROPHENYL)-1-{4-[(2-PIPERIDYL)ETHOXY]BENZYL}-6-1,2,3,4-TETRAHYDROISOQUINOLYLOXY)ACETAMIDE

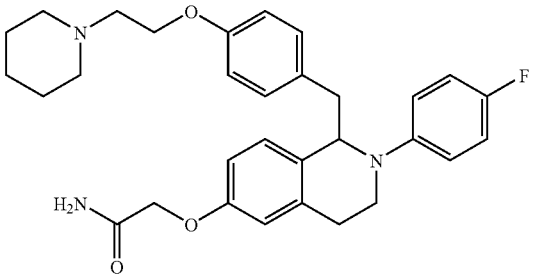

To a solution of 2-(4-fluorophenyl)-1-{4-[(2-piperidyl) ethoxy]benzyl}-1,2,3,4-tetrahydroisoquinolin-6-ol (0.100 g, 0.2 mmol) in THF (1 ml) and DMF (5 drops) on ice was added sodium hydride (0.024 g, 0.6 mmol). To the flask was added bromoacetamide (0.083 g, 0.6 mmol). While warming to room temperature the reaction was allowed to stir for 6 hours. The reaction was quenched with an aqueous solution of sodium bicarbonate and extracted with dichloromethane. The organic layer was dried over MgSO$_4$, filtered and concentrated. The product was purified by HPLC as described above to yield the title compound (0.005 g, 4.8% yield): ES-MS (m/z) 518 [M+H]$^+$.

Example 55

SYNTHESIS OF N-(CARBAMOYLMETHYL )-2-(24-FLUOROPHENYL)-1-{4-[(2-PIPERIDYL)ETHOXY]BENZYL}(6-1,2,3,4-TETRAHYDROISOQUINOLYLOXY))ACETAMIDE

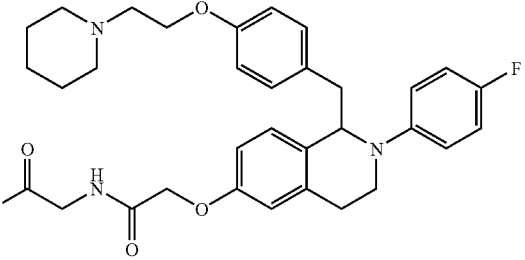

To a solution of 2-(4-fluorophenyl)-1-{4-[(2-piperidyl) ethoxy]benzyl}-1,2,3,4-tetrahydroisoquinolin-6-ol (0.100 g, 0.2 mmol) in THF (1 ml) and DMF (5 drops) on ice was added sodium hydride (0.024 g, 0.6 mmol). To the flask was added bromoacetamide (0.083 g, 0.6 mmol). While warming to room temperature the reaction was allowed to sit for 6 hours. The reaction was quenched with an aqueous solution of sodium bicarbonate and extracted with dichloromethane. The organic layer was dried over $MgSO_4$, filtered and concentrated. The product was purified by semipreparative HPLC (C-18 column, 10-100% acetonitrile/water with 0.1% trifluoroacetic acid) to yield the title compound (0.008 g, 7.0% yield): 1H NMR ($CDCl_3$) 6.6-7.3 (m, 11H), 6.0 (broad s, 2H), 5.55 (broad s, 1H), 4.7 (t, 1H), 4.5 (s, 2H), 4.1 (m, 4H), 3.5 (m, 2H), 3.05 (m, 1H), 2.9 (m, 4H), 2.65 (m, 1H), 2.55 (m, 4H), 1.65 (m, 4H), 1.5 (m, 2H); ES-MS (m/z) 575 $[M+H]^+$.

Example 56

SYNTHESIS OF 2-CYCLOPROPANECARBO-NYL-1-{4-[(2-PIPERIDYL)ETHOXY]BENZYL}-1,2,3,4-TETRAHYDROISOQUINOLIN-6-OL

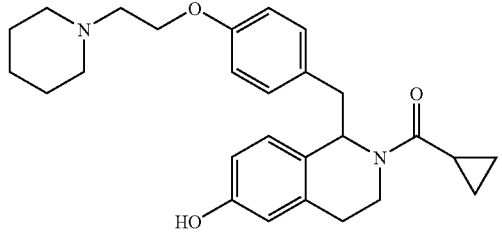

A. 2-(4-Hydroxyphenyl)-N-{2-[3-(phenylmethoxy) phenyl]ethyl]acetamide

A solution of 2-[3-(phenylmethoxy)phenyl]ethylamine (2.80 g, 12.3 mmol), 4-hydroxyphenylacetic acid (2.25 g, 14.8 mmol), N,N-diisopropylethylamine (2.79 mL, 16 mmol), and EDCI (3.07 g, 16 mmol) in 20 mL of DMF was stirred at room temperature for 10 h. The reaction mixture was poured into 100 mL of water and the aqueous layer was extracted with $CH_2Cl_2$. The organic layer was dried over $MgSO_4$, concentrated, and purified by column chromatography ($SiO_2$, hexanes/ethyl acetate, 1:1) to provide the title compound (2.50 g, 56% yield): ES-MS, (m/z) 362 $[M+H]^+$.

B. 1-(4-Hydroxybenzyl)-(6-phenylmethoxy)-1,2,3,4-tetrahydroisoquinoline

The title compound was prepared as described in Example 44.E, using 2-(4-hydroxyphenyl)-N-{2-[3-(phenylmethoxy) phenyl]ethyl} acetamide (3.69 g, 0.01 mol) to provide the title compound (0.57 g, 17% yield): ES-MS (m/z) 346 $[M+H]^+$.

C. 2-Cyclopropanecarbonyl-1-(4-hydroxybenzyl)-(6-phenylmethoxy)-1,2,3,4-tetrahydroisoquinoline To a solution of cyclopropane carboxylic acid (56 µl, 0.7 mmol) in DMF (0.5 ml) was added 1-(3-dimethylaminopropyl)-3-ethylcarbodiimide hydrochloride (0.0997 g, 0.52 mmol) followed by a solution of 1-(4-hydroxybenzyl)-(6-phenylmethoxy)-1,2,3,4-tetrahydroisoquinoline (0.150 g, 0.43 mmol) in DMF (0.5 ml). The reaction was allowed to stir overnight. Solvent was removed. The reaction was diluted with ethyl acetate, washed with 1 N HCl, 10% sodium carbonate solution, and brine. The organic layer was dried over $MgSO_4$, filtered and concentrated to yield the title compound (0.15 g, 84% yield): ES-MS (m/z) 414 $[M+H]^+$.

D. 2-Cyclopropanecarbonyl-1-{[4-(2-piperidylethoxy)phenyl]methyl})-(6-phenylmethoxy) 1,2,3,4-tetrahydroisoquinoline The title compound was prepared as described in Example 44.F, using 2-cyclopropanecarbonyl-1-(4-hydroxybenzyl)-6-phenylmethoxy-1,2,3,4-tetrahydroisoquinoline (0.15 g, 0.36 mmol) to provide the title compound (0.050 g, 27% yield): ES-MS (m/z) 525 $[M+H]^+$.

E. 2-Cyclopropanecarbonyl-1-{4-[(2-piperidyl)ethoxy]benzyl})-1,2,3,4-tetrahydroisoquinolin-6-ol The title compound was prepared as described in Example 44.G, using 2-cyclopropanecarbonyl-1-{[4-(2-piperidylethoxy)phenyl]methyl})-(6-phenylmethoxy)-1,2,3,4-tetrahydroisoquinoline (0.050 g, 0.1 mmol) to afford the title compound (0.01 g, 22% yield): 1H NMR ($CDCl_3$) 6.5-7.0 (m, 7H), 5.5 (m, 0.5H) 5.2 (m, 0.5H) (amide bond rotamer), 4.5-4.6 (m, 1H), 4.0-4.2 (m, 2H), 3.8-3.9 (m, 0.5H), 3.6-3.7 (m, 0.5H) (amide bond rotamer), 3.0-3.2 (m, 2H), 2.5-2.9 (m, 8H), 1.6-1.8 (m, 4H), 1.1-1.4 (m, 2H), 0.6-1.1 (m, 4H), 0.5-0.6 (m, 0.5H), 0.3-0.4 (m, 0.5H) (amide bond rotamer); ES-MS (m/z) 435 $[M+H]^+$.

Example 57

SYNTHESIS OF 2-(2-METHYLPROPANOYL)-1-{4-[(2-PIPERIDYL)ETHOXY]BENZYL}-1,2,3,4-TETRAHYDROISOQUINOLIN-6-OL

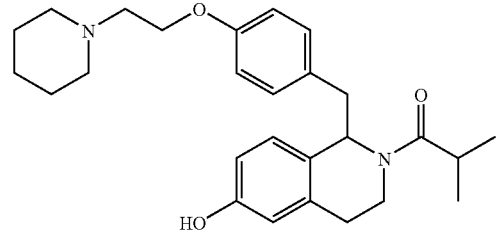

A. 2-(2-Methylpropanoyl)-1-(4-hydroxybenzyl)-(6-phenylmethoxy)-1,2,3,4-tetrahydroisoquinoline The title compound was prepared as described in Example 56.C, using isobutyric acid (103 µl, 1.12 mmol) and diisopropylethyl amine (10 µl, 0.4 mol) to provide the title compound (0.054 g, 36% yield): ES-MS (m/z) 416 $[M+H]^+$.

B. 2-(2-Methylpropanoyl)-1-{4-[(2-piperidyl)ethoxy]benzyl}-1,2,3,4-tetrahydroisoquinolin-6-ol The title compound was prepared as described in Examples 44.F and 44.G starting with 2-methylpropanoyl-1-(4-hydroxybenzyl)-(6-phenylmethoxy)-1,2,3,4-tetrahydroisoquinoline (0.054 g, 0.13 mmol) to provide the title compound: (0.004 g, 7% yield): ES-MS (m/z) 437 $[M+H]^+$.

Example 58

SYNTHESIS OF 2-CYCLOHEXANECARBONYL-1-{[4-(2-PIPERIDYLETHOXY)PHENYL]METHYL}-1,2,3,4-TETRAHYDROISOQUINOLIN-6-OL

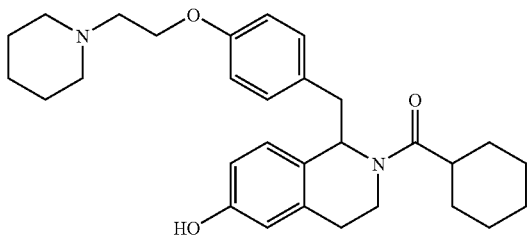

A. 2-Cyclohexanecarbonyl-1-(4-hydroxybenzyl)-6-phenylmethoxy-1,2,3,4-tetrahydroisoquinoline The title compound was prepared as described in Example 56.C, using cyclohexane carboxylic acid (0.143 g, 1.12 mmol). The crude product was purified via radial chromatography to provide the title compound (0.056 g, 33% yield): ES-MS (m/z) 456 [M+H]$^+$.

B. 2-Cyclohexanecarbonyl-1-{[4-(2-piperidylethoxy)phenyl]methyl})-6-phenylmethoxy-1,2,3,4-tetrahydroisoquinoline The title compound was prepared as described in Example 44.F, using 2-cyclohexanecarbonyl-1-(4-hydroxybenzyl)-6-phenylmethoxy-1,2,3,4-tetrahydroisoquinoline (0.56 g, 0.12 mmol) to provide the title compound (0.056 g, 68% yield): ES-MS (m/z) 567 [M+H]$^+$.

C. 2-Cyclohexanecarbonyl-1-{[4-(2-piperidylethoxy)phenyl]methyl}-1,2,3,4-tetrahydroisoquinolin-6-ol The title compound was prepared as described in Example 44.G, using 2-cyclohexanecarbonyl-1-{[4-(2-piperidylethoxy)phenyl]methyl}-6-phenylmethoxy-1,2,3,4-tetrahydroisoquinoline (0.056 g) to provide the title compound (0.008 g, 17% yield): $^1$H NMR (CDCl$_3$) 6.5-7.1 (m, 7H), 5.6 (t, 0.5H), 4.9 (t, 0.5H) (amide bond rotamers), 4.7 (m, 1H), 4.1 (t, 2H), 3.7 (m, 0.5H), 3.5 (m, 0.5H), 2.7-3.1 (m, 10H), 0.8-1.9 (m, 16H); ES-MS (m/z) 477 [M+H]$^+$.

Example 59

2-(4-FLUOROPHENYL}-1-[(4-HYDROXYPHENYL}METHYL]-1,2,3,4-TETRAHYDROISOQUINOLIN-6-OL

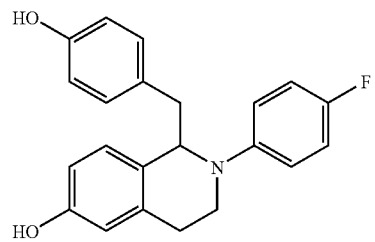

The title compound was prepared as described in Example 2 using 2-(4-fluorophenyl)-6-methoxy-1-{4-hydroxybenzyl}-1,2,3,4-tetrahydroisoquinoline (0.8 g, 2.2 mmol). Purification by column chromatography (SiO$_2$, hexanes/ethylacetate, 2:1) provided the title compound (0.4 g, 57% yield): ES-MS (m/z) 350 [M+H]$^+$.

Example 60

1-[(4-FLUOROPHENYL)METHYL]-2-(4-FLUOROPHENYL)-1,2,3,4-TETRAHYDROISOQUINOLIN-6-OL

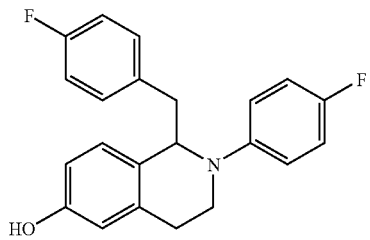

A. N-{2-[(3-Phenylmethoxy)phenyl]ethyl}-N-(4-fluorophenyl)-2-[2-(4-fluorophenyl)]acetamide The title compound was prepared as described in Example 3.A using (4-fluorophenyl)-{2-[3-(phenylmethoxy)phenyl]ethyl}amine (6.42 g, 20 mmol) and 4-fluorophenylacetyl chloride (3.45 g, 20 mmol) to provide the title compound (9 g, 99% yield): ES-MS (m/z) 458 [M+H]$^+$.

B. 1-{4-Fluorobenzyl}-6-phenylmethoxy-2-fluorophenyl-1,2,3,4-tetrahydroisoquinoline The title compound was prepared as described in Example 1.D using N-{2-[(3-phenylmethoxy)phenyl]ethyl}-N-(4-fluorophenyl)-2-{2-(4-fluorophenyl}acetamide (9 g, 19.7 mmol). Purification by column chromatography (SiO$_2$, hexanes/ethylacetate 3:1) provided the title compound (3.2 g, 36% yield): ES-MS (m/z) 442 [M+H]$^+$.

C. 1-[(4-Fluorophenyl)methyl]-2-(4-fluorophenyl)-1,2,3,4-tetrahydroisoquinolin-6-ol The title compound was prepared as described in Example 14.D. using 1-[(4-fluorophenyl)methyl]-6-phenylmethoxy-2-fluorophenyl-1,2,3,4-tetrahydroisoquinoline (0.2 g, 0.45 mmol). Purification by column chromatography (SiO$_2$, hexanes/ethylacetate, 2:1) provided the title compound (0.1 g, 62% yield): ES-MS (m/z) 352 [M+H]$^+$.

Examples 61-134

Experimental Procedure for Combinatorial Library

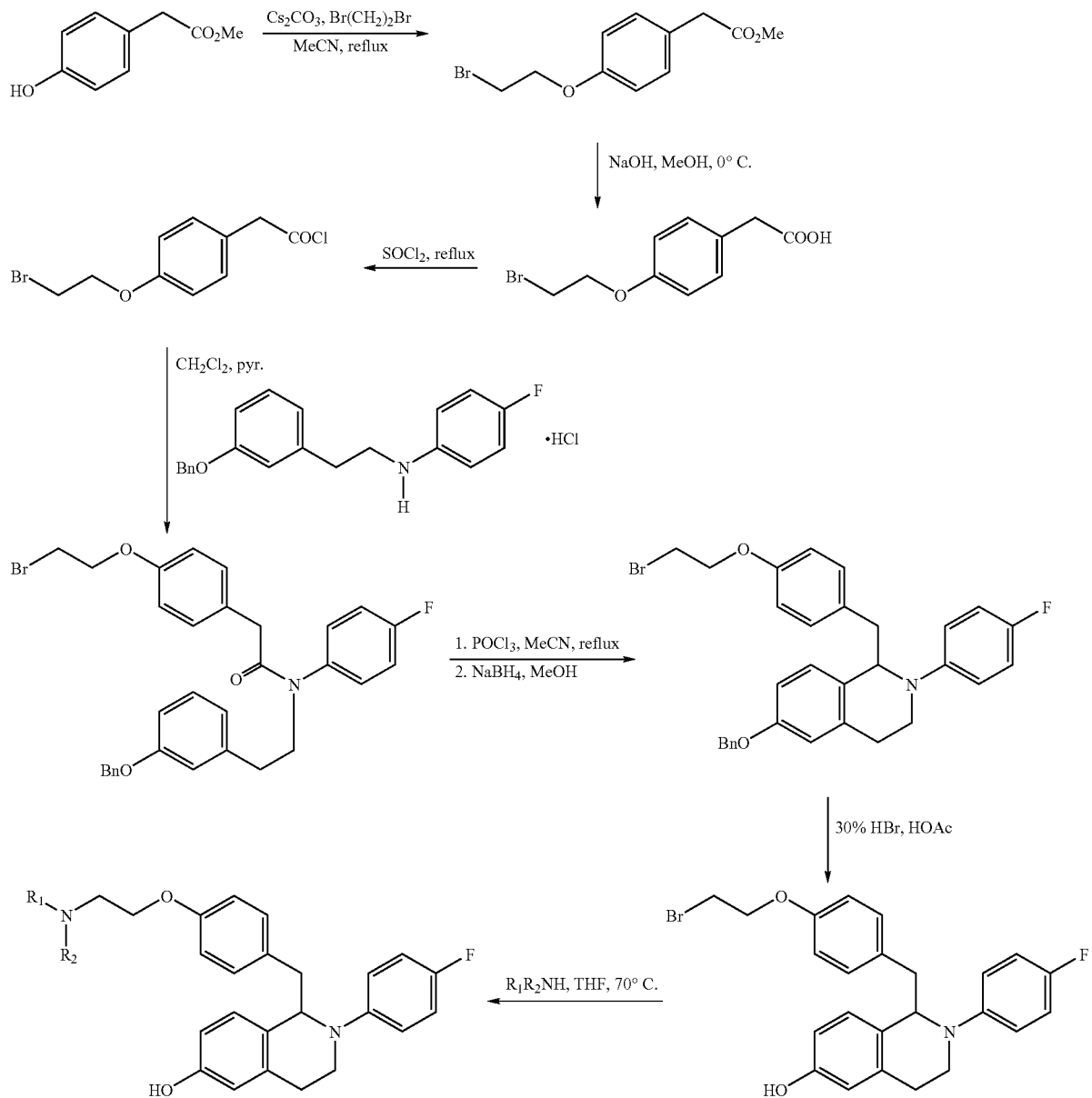

A. 4-(2-Bromoethoxy)phenylacetyl chloride

4-Hydroxyphenylacetic acid (100 g, 0.6 mol) and cesium carbonate (250 g) were suspended in 300 mL of anhydrous acetonitrile followed by addition of 1,2-dibromoethane (300 mL). The suspension was brought to reflux for 24 hours in a 2 L 3 neck round bottom flask fitted with a mechanical stirrer and reflux condenser then cooled to room temperature. The mixture was diluted to a volume of 2 L by addition of ethyl ether and the suspension was filtered. Concentration of the filtrate in vacuo afforded a colorless oil which was purified by vacuum distillation (0.2 mm Hg, 140-145° C.) to give methyl 4-(2-bromoethoxy)-phenylacetate (93.14 g, 60% yield) as a colorless oil. The methyl 4-(2-bromoethoxy)-phenylacetate was taken into methanol (250 mL) and the resulting solution was cooled to 0° C. Sodium hydroxide (29 g) in a minimum of water was added to the methanol solution in portions and the mixture was stirred at 0° C. for an additional 30 minutes. The solution was warmed to room temperature then concentrated to a white solid. The residue was taken into water and the solution washed once with ethyl ether. The aqueous solution was then acidified to pH 1 by addition of concentrated aqueous hydrochloric acid to give a thick suspension. Filtration and drying afforded 4-(2-bromoethoxy)-phenylacetic acid (86 g, 97% yield) as a colorless solid. The 4-(2-bromoethoxy)-phenylacetic acid (50 g) was taken into thionyl chloride (70 mL) and brought to reflux under an atmosphere of nitrogen for 2 hours. Fractional vacuum distillation (0.2 mm Hg, 139-140° C.) afforded 4-(2-bromoethoxy)phenylacetyl chloride (46.0 g, 86% yield) as a colorless oil that quickly crystallized on cooling. $^1$H NMR (CDCl$_3$) 6.95, 6.76, 6.60 (m, 11H, Ar—H), 4.68 (m, 1H), 4.24 (m, 2H), 3.80 (m, 1H), 3.41-3.63 (m, 3H), 3.07 (m, 1H), 2.87 (m, 2H), 2.61 (m, 1H); ES-MS (m/z) 458 [M+H]$^+$.

B. 1-[4-(2-Bromoethoxy)benzyl]-2-(4-fluorophenyl)-1,2,3,4-tetrahydroisoquinolin-6-ol N-(4-Fluorophenyl)-4-benzyloxyphenethylamine hydrochloride (19.1 g, 53.4 mmol) was suspended in dichloromethane (100 mL) followed by addition of pyridine (11 mL, 133.5 mmol) and the resulting solution was cooled to 0° C. 4-(2-Bromoethoxy)-phenylacetyl chloride (16.3 g, 58.7 mmol) in dichloromethane (50 mL) was added dropwise to the amine solution over 30 minutes followed by warming the mixture to room temperature. The solution was washed with 1.0 N aqueous hydrochloric acid, dried over anhydrous MgSO$_4$ then filtered. The filtrate was concentrated to afford 34.2 g of a yellow oil. The oil was taken into anhydrous acetontrile (150 mL) and phosphorous oxychloride (75 mL) was added to the solution. The mixture was brought to reflux under an atmosphere of nitrogen for 12 hours then cooled to room temperature and concentrated to an oil. The residue was taken into ethyl acetate and the solution cooled to 0° C. followed by careful quenching by slow addition of one volume equivalent of water. The organic layer was washed with additional water then with saturated aqueous sodium chloride. The organic layer was then concentrated to an oil and taken into dichloromethane and methanol (1:1, 250 mL). The resulting solution was cooled to 0° C. and sodium borohydride (3.9 g) was added in portions over 15 minutes. The mixture was warmed to room temperature and stirred an additional 15 minutes, during which time the evolution of hydrogen gas ceased. The reaction mixture was concentrated and partitioned with ethyl acetate and water. The organic layer was washed with additional water then with saturated aqueous sodium chloride and dried over anhydrous MgSO$_4$. Filtration and concentration afforded a yellow oil. The oil was taken into 30% hydrogen bromide in acetic acid (175 mL) and the solution was stirred for 15 minutes then partitioned with ethyl acetate (500 mL) and water (500 mL). Solid sodium hydrogen carbonate (75 g) was added in portions and the organic layer was washed 3× with additional water then with saturated aqueous sodium chloride and dried over anhydrous MgSO$_4$. Filtration, concentration and purification by column chromatography (SiO$_2$) afforded 1-[4-(2-bromoethoxy)benzyl]-2-(4-fluorophenyl)-1,2,3,4-tetrahydroisoquinolin-6-ol as a yellow oil (8.75 g). $^1$H NMR (CDCl$_3$) 6.95, 6.76, 6.60 (m, 11H, Ar—H), 4.68 (m, 1H), 4.24 (m, 2H), 3.80 (m, 1H), 3.41-3.63 (m, 3H), 3.07 (m, 1H), 2.87 (m, 2H), 2.61 (m, 1H); ES-MS m/z 458 [M+H]$^+$.

C. General Procedure for Alkylations of 1-[4-(2-Bromoethoxy)benzyl]-2-(4-fluorophenyl)-1,2,3,4-tetrahydroisoquinolin-6-ol A 16 mm×100 mm screw cap tube was charged with the bromide (75 mg, 0.164 mmol) and THF (1 mL). The appropriate secondary amine (1.0 mmol, 6.1 equiv) was added and the tube was sealed. The reaction was heated at 70° C. for 24 hours with magnetic stirring. The reaction was cooled to 23° C., taken up in acetonitrile/water (1:1, 2 mL) and purified by preparative HPLC (C-18 column, 10%-90% acetonitrile in water, with 0.1% HCl). The product was isolated and the solvents were removed by lyophilization. All final products were characterized by ES-MS.

D. Representative Compounds

By the procedures set forth above, the compounds listed in Table 2 were prepared.

TABLE 2

Representative Compounds

| Example No. | Structure | m/z [M + H]$^+$ |
|---|---|---|
| 61 | (structure) | 481 |
| 62 | (structure) | 479 |

TABLE 2-continued

Representative Compounds

| Example No. | Structure | m/z [M + H]+ |
|---|---|---|
| 63 | 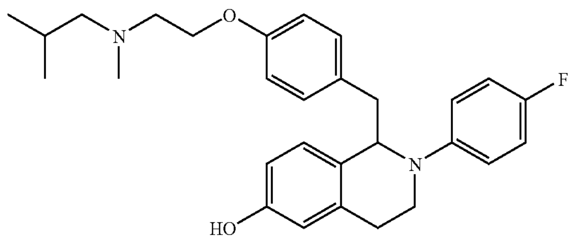 | 463 |
| 64 | 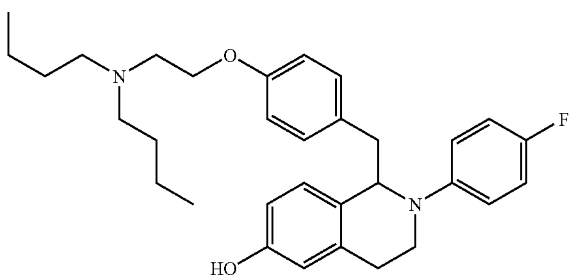 | 505 |
| 65 | 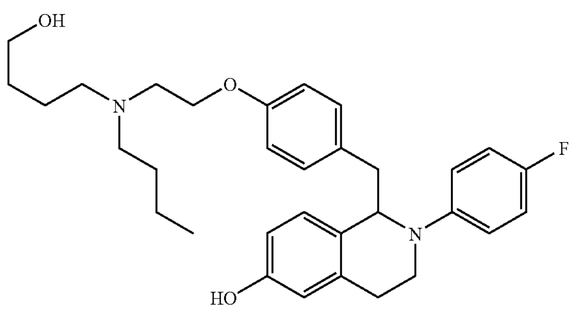 | 521 |
| 66 | 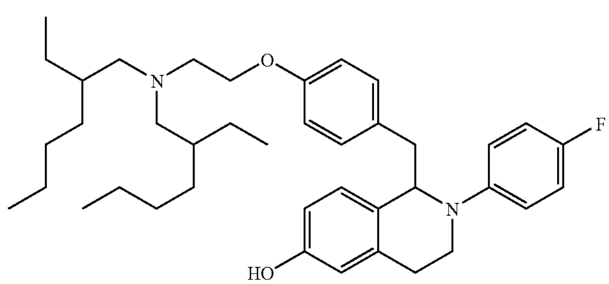 | 618 |
| 67 | 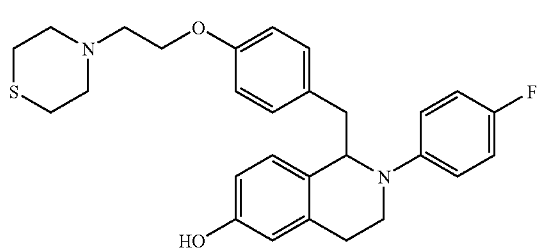 | 479 |

TABLE 2-continued
Representative Compounds
| Example No. | Structure | m/z [M + H]+ |
|---|---|---|
| 68 | 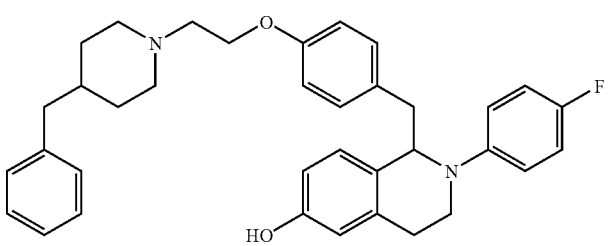 | 551 |
| 69 | 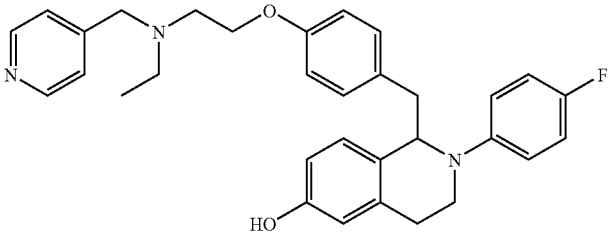 | 512 |
| 70 | 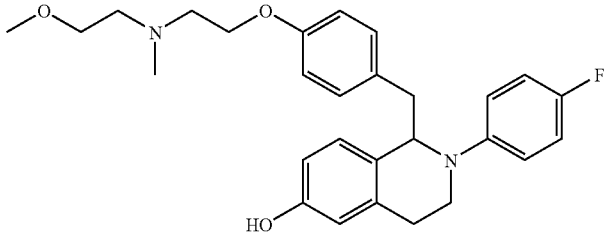 | 465 |
| 71 | 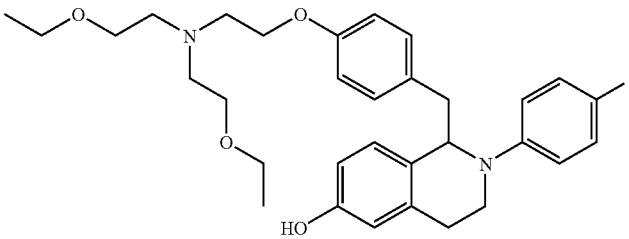 | 537 |
| 72 | 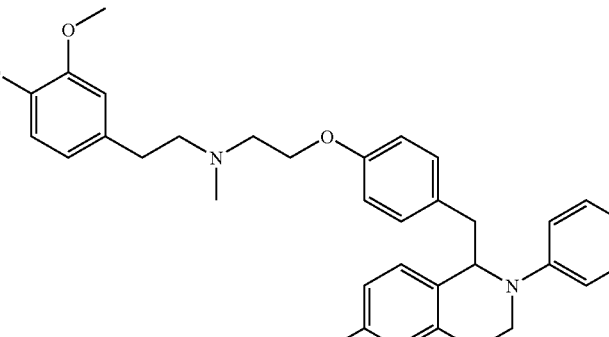 | 571 |

TABLE 2-continued
Representative Compounds
| Example No. | Structure | m/z [M + H]+ |
|---|---|---|
| 73 | 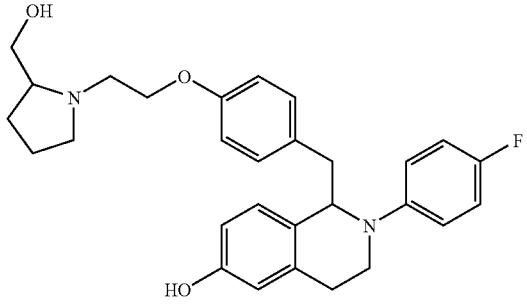 | 477 |
| 74 | 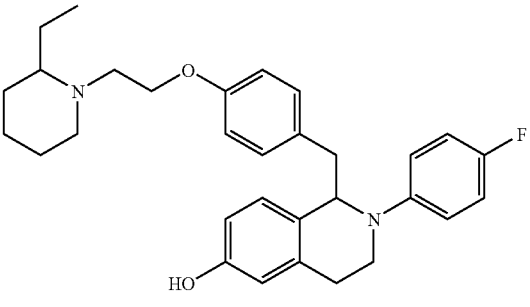 | 489 |
| 75 | 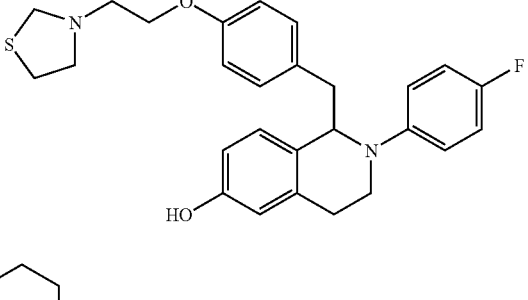 | 465 |
| 76 | 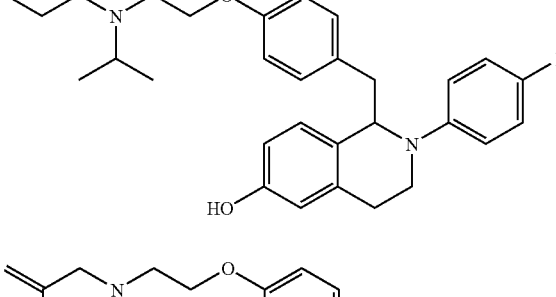 | 517 |
| 77 | 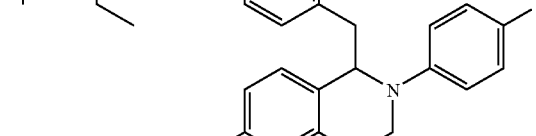 | 475 |

TABLE 2-continued

Representative Compounds

| Example No. | Structure | m/z [M + H]+ |
|---|---|---|
| 78 | 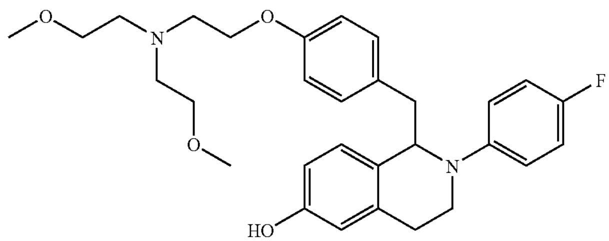 | 509 |
| 79 | 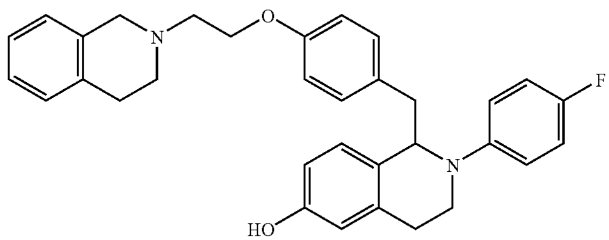 | 509 |
| 80 | 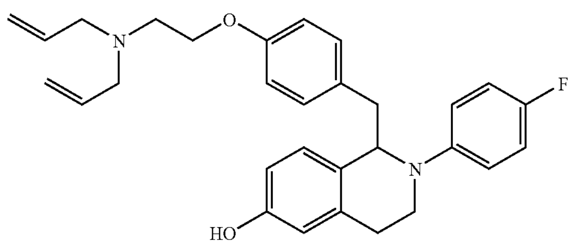 | 473 |
| 81 | 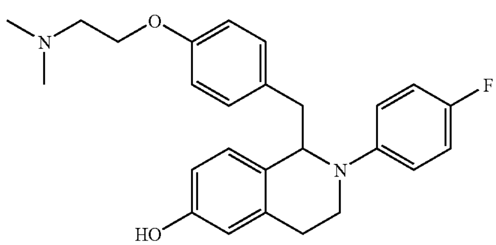 | 421 |
| 82 | 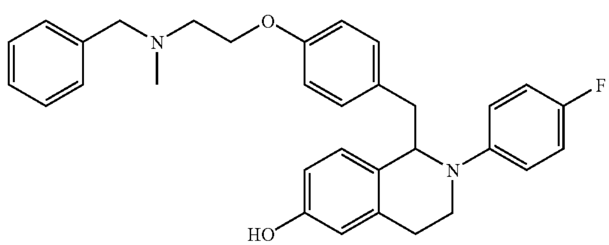 | 497 |
| 83 | 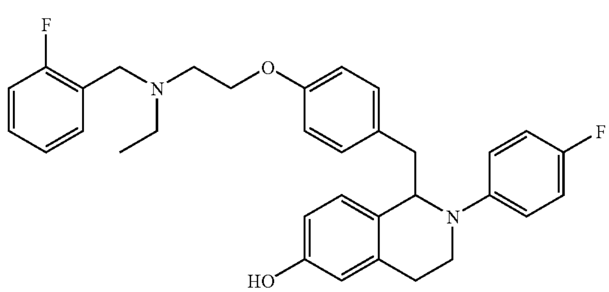 | 529 |

TABLE 2-continued
Representative Compounds
| Example No. | Structure | m/z [M + H]+ |
|---|---|---|
| 84 | 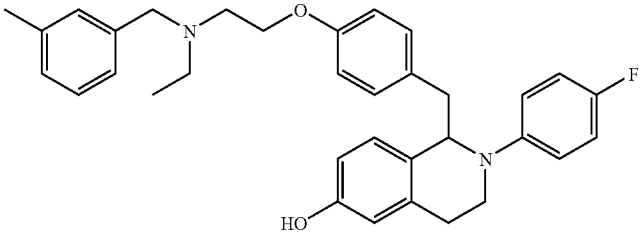 | 525 |
| 85 | 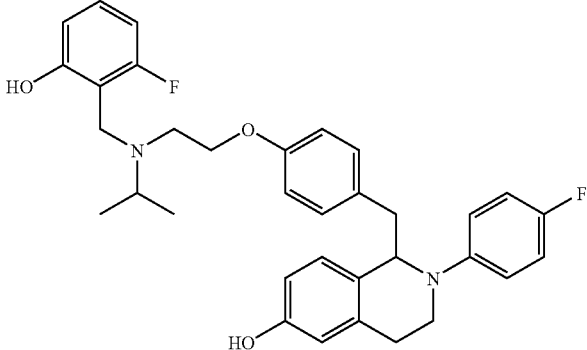 | 577 |
| 86 | 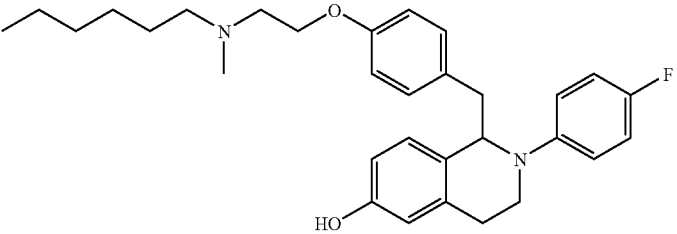 | 491 |
| 87 | 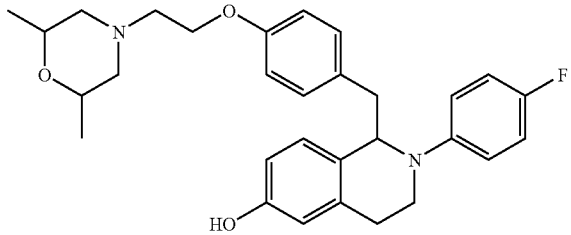 | 491 |
| 88 | 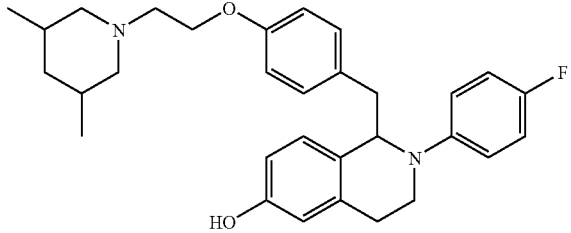 | 489 |

TABLE 2-continued

Representative Compounds

| Example No. | Structure | m/z [M + H]+ |
|---|---|---|
| 89 | 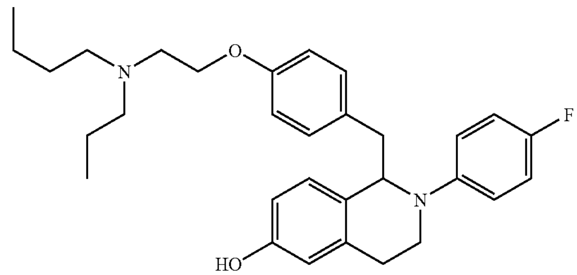 | 505 |
| 90 | 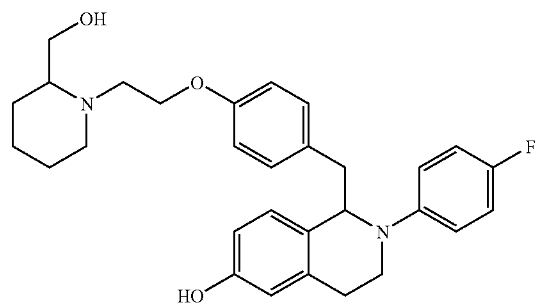 | 491 |
| 91 | 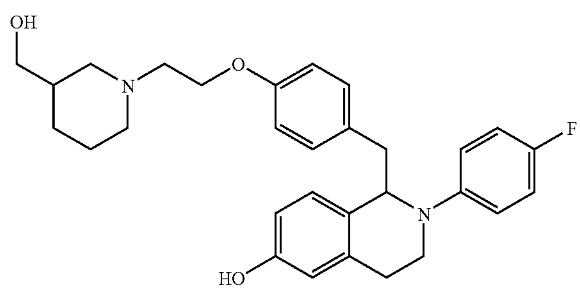 | 491 |
| 92 | 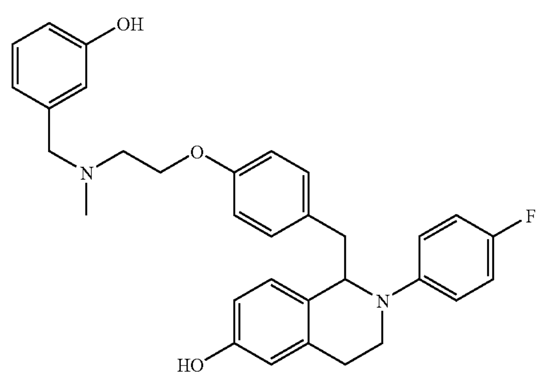 | 455 |
| 93 | 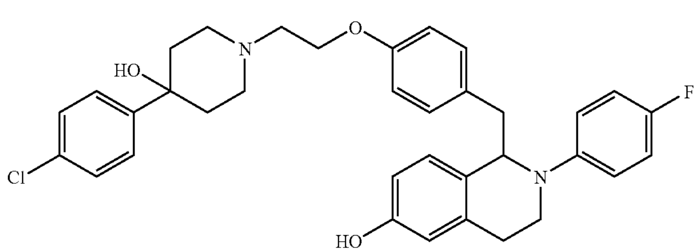 | 487 |

TABLE 2-continued

Representative Compounds

| Example No. | Structure | m/z [M + H]+ |
|---|---|---|
| 94 | 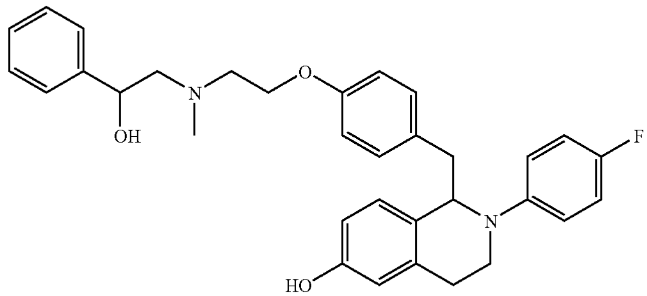 | 587 |
| 95 | 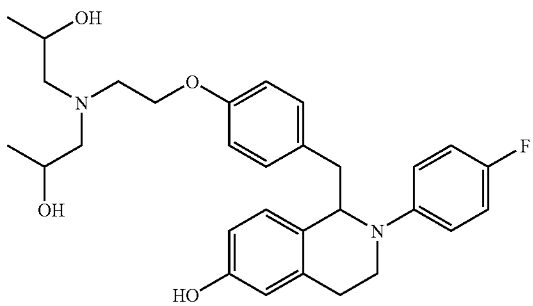 | 509 |
| 96 | 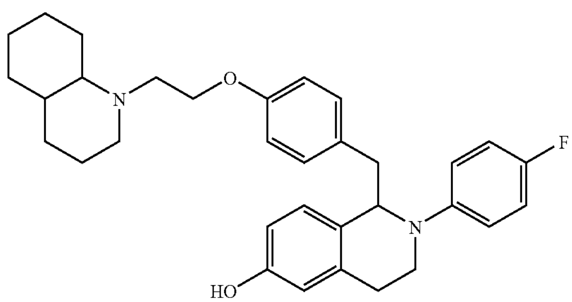 | 515 |
| 97 | 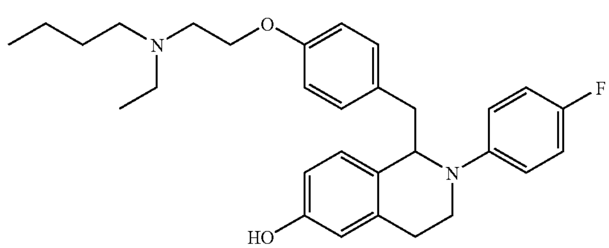 | 477 |
| 98 | 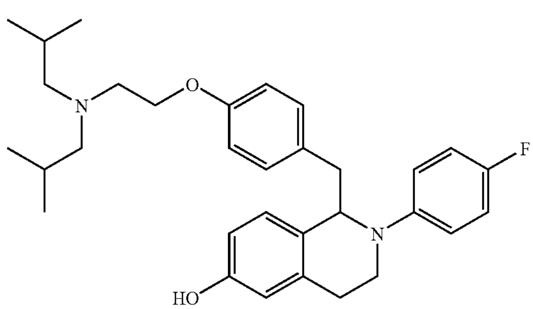 | 505 |

TABLE 2-continued

Representative Compounds

| Example No. | Structure | m/z [M + H]+ |
|---|---|---|
| 99 | | 451 |
| 100 | | 540 |
| 101 | | 512 |
| 102 | | 475 |
| 103 | | 539 |

TABLE 2-continued
Representative Compounds
| Example No. | Structure | m/z [M + H]+ |
|---|---|---|
| 104 | 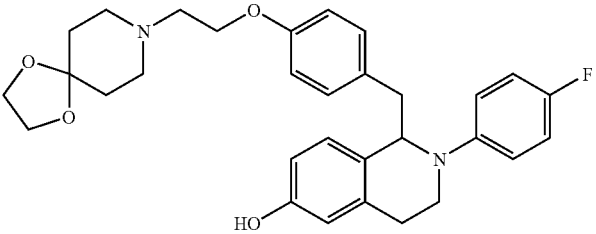 | 519 |
| 105 | 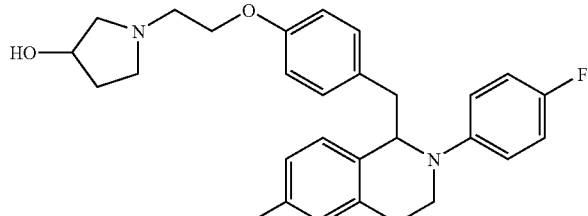 | 463 |
| 106 | 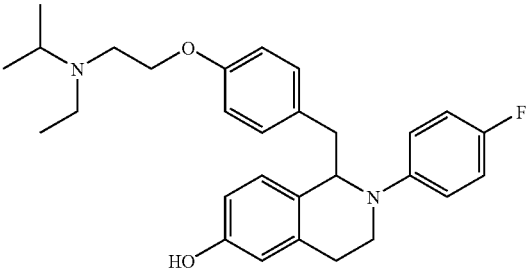 | 463 |
| 107 | 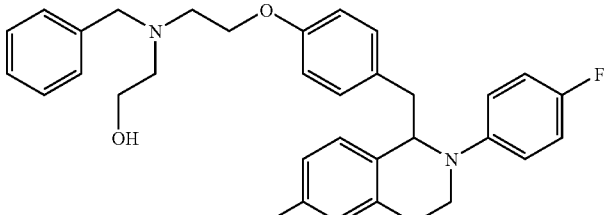 | 527 |
| 108 | 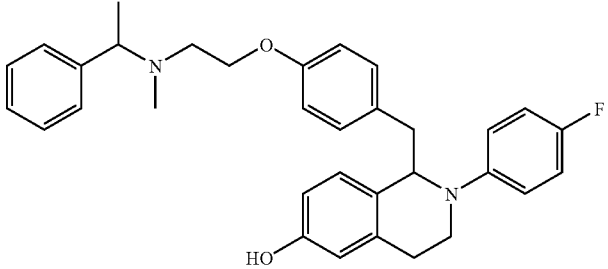 | 511 |

TABLE 2-continued

Representative Compounds

| Example No. | Structure | m/z [M + H]+ |
|---|---|---|
| 109 | 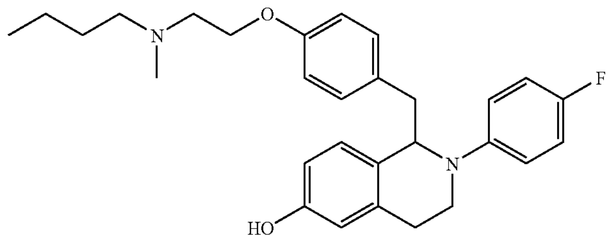 | 463 |
| 110 | 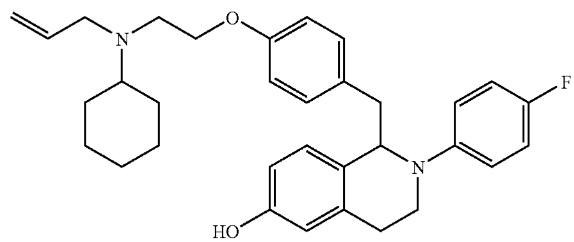 | 515 |
| 111 | 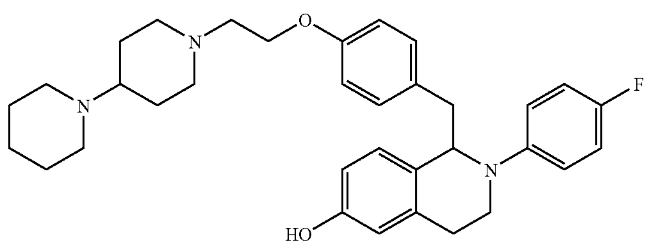 | 544 |
| 112 | 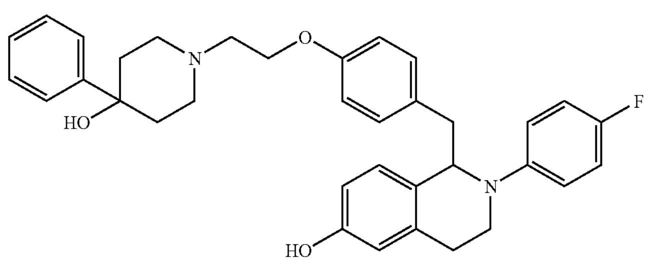 | 553 |
| 113 | 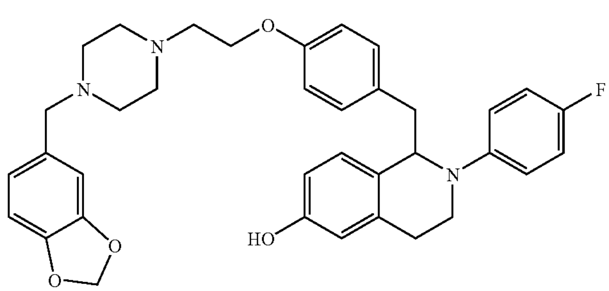 | 596 |
| 114 | 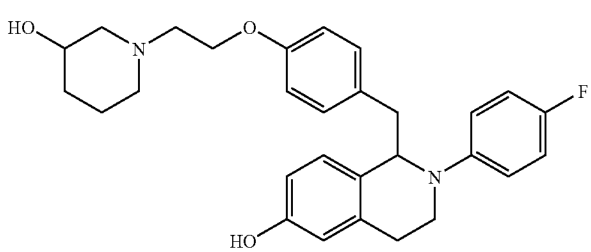 | 455 |

TABLE 2-continued

Representative Compounds

| Example No. | Structure | m/z [M + H]+ |
|---|---|---|
| 115 | 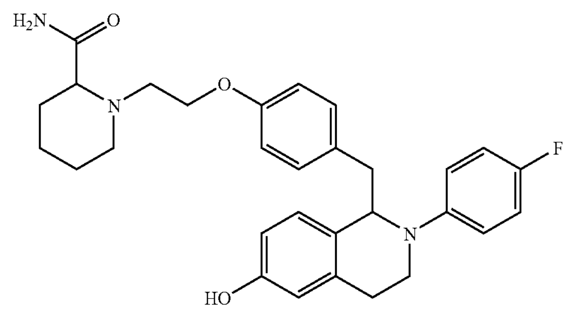 | 504 |
| 116 | 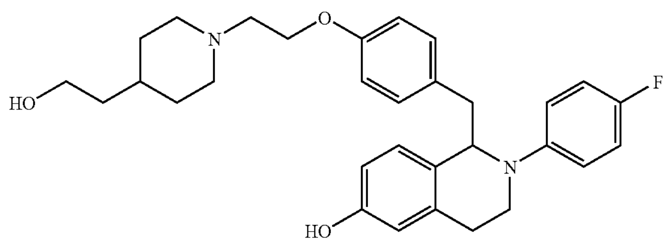 | 505 |
| 117 | 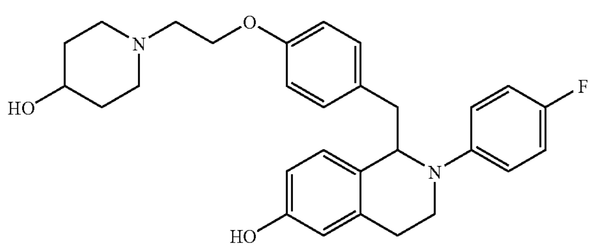 | 477 |
| 118 | 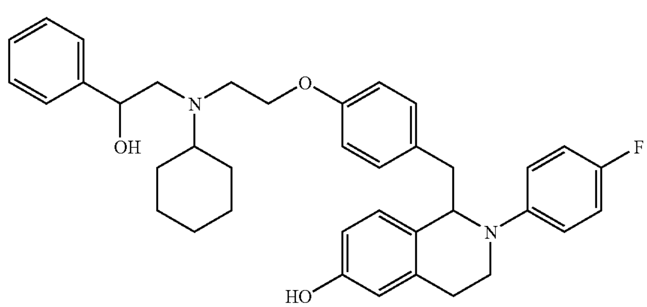 | 596 |
| 119 | 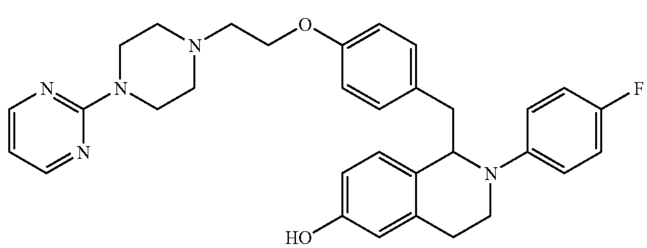 | 563 |

TABLE 2-continued

Representative Compounds

| Example No. | Structure | m/z [M + H]+ |
|---|---|---|
| 120 | | 559 |
| 121 | | 563 |
| 122 | | 553 |
| 123 | | 511 |
| 124 | | 476 |

TABLE 2-continued

Representative Compounds

| Example No. | Structure | m/z [M + H]+ |
|---|---|---|
| 125 | 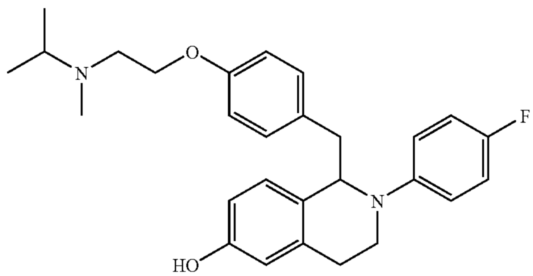 | 449 |
| 126 | 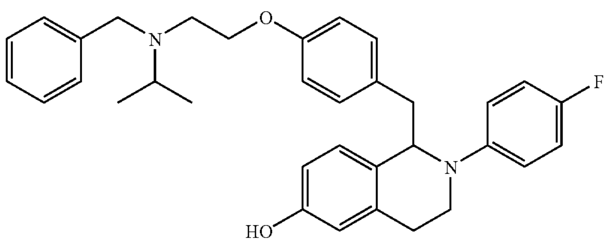 | 525 |
| 127 | 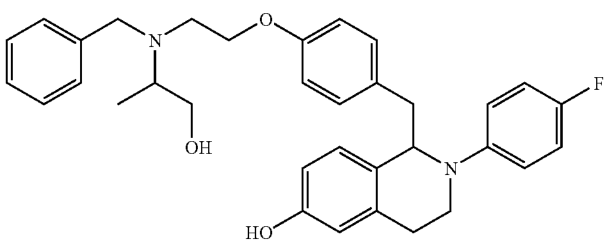 | 541 |
| 128 | 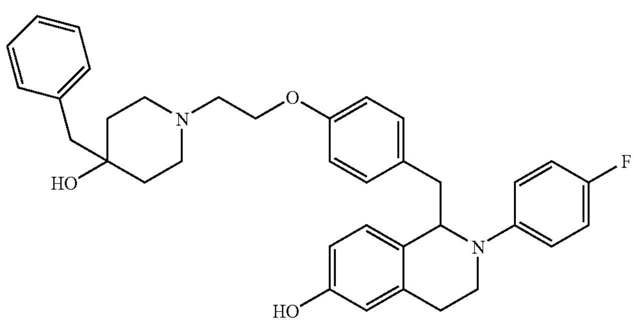 | 567 |
| 129 | 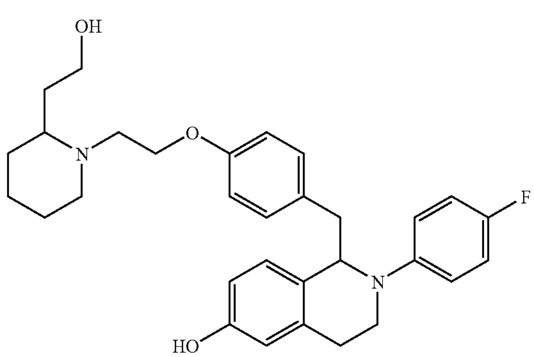 | 505 |

TABLE 2-continued

Representative Compounds

| Example No. | Structure | m/z [M + H]+ |
|---|---|---|
| 130 | 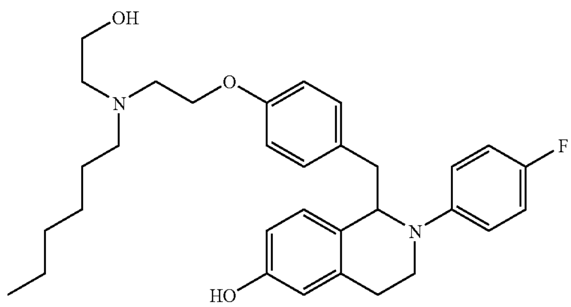 | 521 |
| 131 | 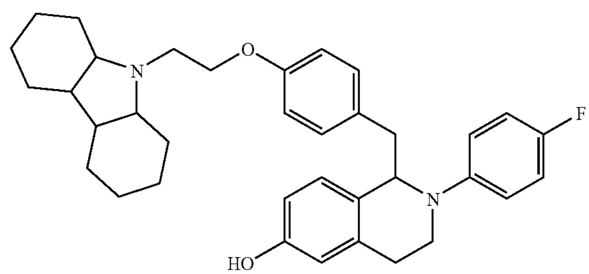 | 555 |
| 132 | 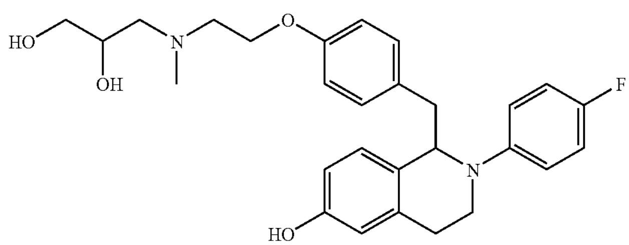 | 481 |
| 133 | 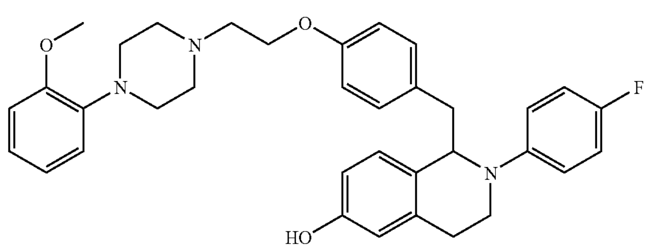 | 568 |
| 134 | 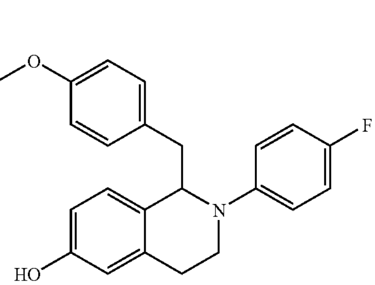 | 435 |

Example 135

2-(4-FLUOROPHENYL)-6-PHENYLMETHOXY-1-{4-[(1-PIPERIDYL)PROP-2-ENYL]BENZYL}-1,2,3,4-TETRAHYDROISOQUINOLINE

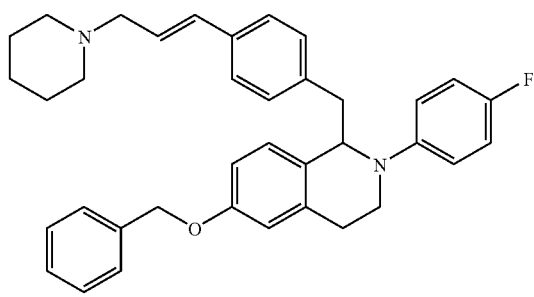

Reaction Scheme
Scheme for Example 135 and 136 (Carbon Sidechains)

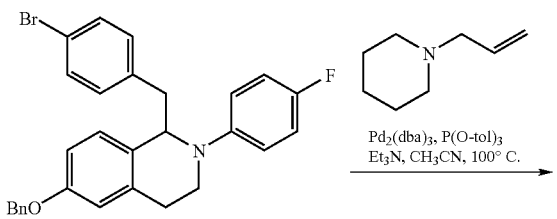

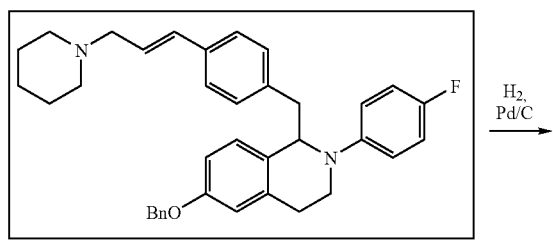
Example 135

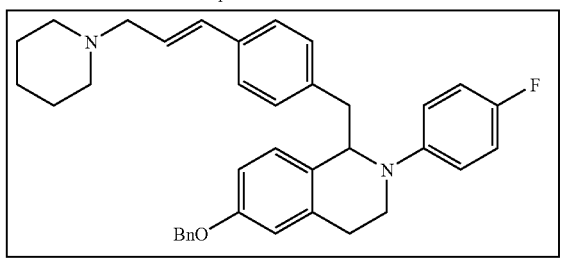
Example 136

To a solution of 1-(4-bromobenzyl)-6-phenylmethoxy-2-phenyl-1,2,3,4-tetrahydroisoquinoline (0.502 g, 1 mmol) in anh acetonitrile (10 mL) under an atmosphere of nitrogen is added Pd(dba)3 (0.092 g, 0.1 mmol), tri-o-tolylphosphine (0.122 g, 0.4 mmol), TEA (3 mL) and piperidineallyl (0.25 g, 2 mmol). The reaction was heated at 100° C. overnight, then cooled to room temperature. The reaction mixture was quenched with water and a 5% HCl solution was added. The crude product was extracted with ethylacetate, washed with brine, dried over $MgSO_4$ and purified by column chromatography (SiO$_2$, CH$_2$Cl$_2$/MeOH, 95:5) to provide the title compound (0.113 g, 21% yield): ES-MS (m/z) 547 [M+H]$^+$.

Example 136

2-(4-FLUOROPHENYL)-1-{4-[(1-PIPERIDYL)PROPYL]BENZYL}-1,2,3,4-TETRAHYDROISOQUINOLIN-6-OL

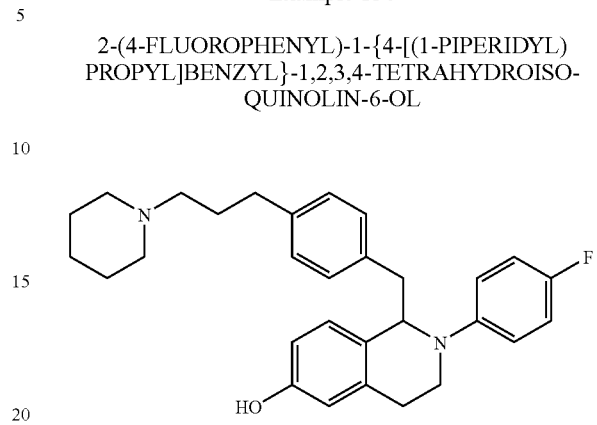

The title compound was prepared as described in Example 44.G using 2-(4-fluorophenyl)-1-{4-[(1-piperidyl)prop-2-enyl]benzyl}-1,2,3,4-tetrahydroisoquinolin-6-ol (0.10 g, 0.18 mmol) to provide the title compound (0.009 g, 11% yield): ES-MS (m/z) 459 [M+H]$^+$.

Example 137

2-(4-FLUOROPHENYL)-5-METHOXY-1-{4-[(2-PIPERIDYL)ETHOXY]BENZYL)}ISONDOLINE

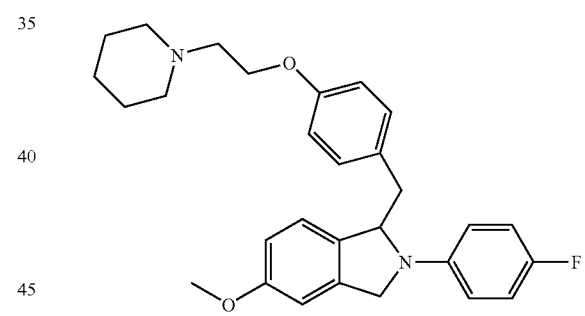

Reaction Scheme
Scheme for Examples 137, 138

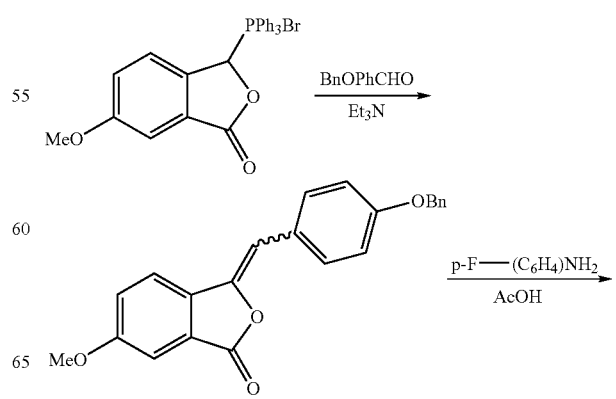

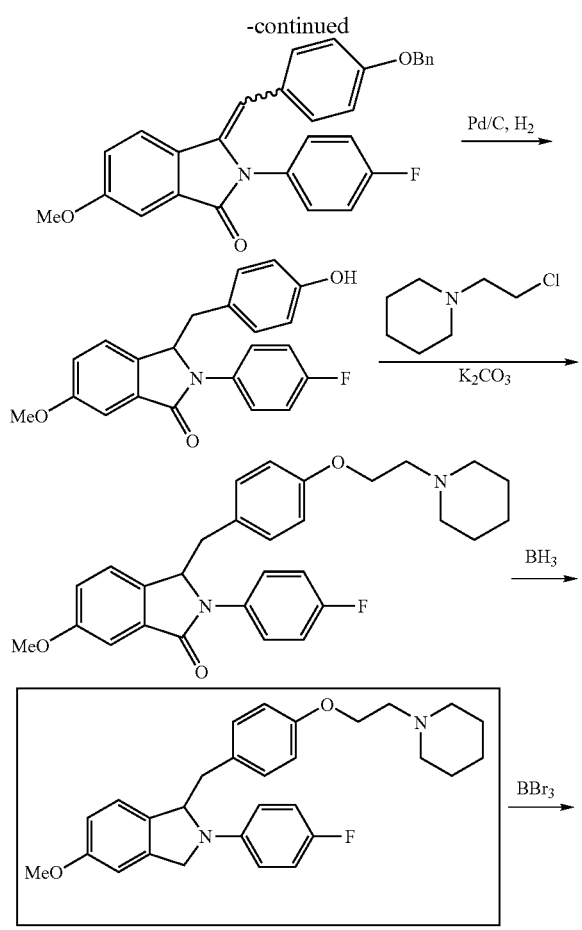

Example 137

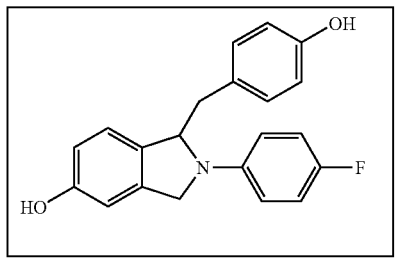

Example 138

A. 2-(4-Fluorophenyl)-3-(4-hydroxybenzyl)-6-methoxyisoindolin-1-one

To a solution of triphenyl(5-methoxy-3-oxo-1,3-dihydroisobenzofuran-1-yl)phosphomium bromide (10.00 g, 19.8 mmol) (Sakamoto et al., *Chem. Pharm. Bull.* 31, 2698-2707, 1983) and 4-benzyloxybenzaldehyde (10.074 g, 24.0 mmol) in $CH_2Cl_2$, (100 mL) at −10° C. vas added triethylamine (4 mL). After stirring at room temperature for 2 hours, the solvent was evaporated. To the residue was added ethyl ether to provide a mixture of (E)- and (Z)-6-methoxy-3-{[4-phenylmethoxy)phenyl]methylene}isobenzofuran-1-one (4.56 g, 64% yield); ES-MS (m/z) 359 [M+H]⁺. A solution of (E)- and (Z)-6-methoxy-3-{[4-phenylmethoxy)phenyl]methylene}isobenzofuran-1-one (2.00 g, 5.58 mmol), 4-fluoroaniline (4 mL) and acetic acid (3 mL) in 1,4-dioxane (30 mL) was prepared and heated at 120° C. overnight. The reaction was quenched with ethyl acetate and washed with 5% hydrochloride solution, then saturated sodium bicarbonate solution. The organic layer was dried over $MgSO_4$, filtered, and concentrated. The residue was purified by chromatography ($SiO_2$, 15-50% ethyl acetate/hexane) to provide a mixture of (E)- and (Z)-6-methoxy-3-{[4-phenylmethoxy)phenyl]methylene}isoindolin-1-one (1.529 g, 61% yield): ES-MS (m/z) 452 [M+H]⁺. A mixture of the (E)- and (Z)-6-methoxy-3-{[4-phenylmethoxy)phenyl]methylene}isoindolin-1-one (1.40 g, 3.1 mmol) was dissolved in methanol (10 mL) and tetrahydrofuran (10 mL), then palladium (10% wt. on activated carbon, 0.20 g) was added and the reaction was stirred under hydrogen overnight. The mixture was filtered through celite, concentrated, and washed with ethyl ether and $CH_2Cl_2$ to provide the title compound (1.094 g, 97% yield): 1H NMR ($CDCl_3$) 7.56 (m, 2H), 7.30 (d, 1H), 7.18 (t, 2H), 7.07 (dd, 1H), 7.02 (d, 1H), 6.60-6.67 (m, 4H), 5.29 (dd, 1H), 5.19 (s, 1H), 3.84 (s, 3H), 3.24 (dd, 1H), 2.78 (dd, 1H); ES-MS (m/z) 364 [M+H]⁺.

B. 2-(4-Fluorophenyl)-6-methoxy-3-{4-[(2-piperidyl)ethoxy]benzyl}isoindolin-1-one The title compound was prepared as described in Example 3.D, using 2-(4-Fluorophenyl)-3-[4-hydroxyphenyl)methyl]-6-methoxyisoindolin-1-one (1.05 g, 2.89 mmol) to provide the title compound (1.097 g, 80% yield): 1H NMR ($CDCl_3$) 7.56 (m, 2H), 7.30 (d, 1H), 7.18 (t, 2H), 7.06 (dd, 1H), 6.99 (d, 1H), 6.70 (s, 4H), 5.30 (dd, 1H), 4.04 (t, 2H), 3.85 (s, 3H), 3.25 (dd, 1H), 2.76 (t and m, 3H), 2.51 (m, 4H), 1.61 (m, 4H), 1.45 (m, 2H); ES-MS (m/z) 475 [M+H]⁺.

C. 2-(4-Fluorophenyl)-5-methoxy-1-{4-[(2-piperidyl)ethoxy]benzyl}isoindoline To a solution of 2-(4-fluorophenyl)-6-methoxy-3-{4-[(2-piperidyl)ethoxy]benzyl}isoindolin-1-one (0.50 g, 1.05 mmol) in tetrahydrofuran (10 mL) under nitrogen was added a 1.5 M solution of borane-tetrahydrofuran complex in tetrahydrofuran (2 mL, 3 mmol). After heating at reflux for 5 hours, the reaction was cooled to room temperature, 6 N HCl solution (6 mL) was added, and the reaction was stirred for 1 hour at room temperature. The mixture was basified with a saturated sodium bicarbonate solution and extracted with $CH_2Cl_2$. The organic layer was dried over $MgSO_4$, filtered, and concentrated. The residue was then purified by chromatography ($SiO_2$, 20-30% ethyl acetate/hexane) to provide the title compound (0.297 g, 61% yield): 1H NMR ($CDCl_3$) 7.05 (t, 2H), 6.91 (d, 1H), 6.78 (dd, 1H), 6.61-6.72 (m, 7H), 5.24 (m, 1H), 4.30-4.41 (m, 3H), 4.15 (dd, 1H), 3.80 (s, 3H), 3.17 (t, 2H), 2.98-3.10 (m, 4H), 2.91 (m, 2H), 1.81 (m, 4H), 1.56 (m, 2H); ES-MS (m/z) 461 [M+H]⁺.

Example 138

2-(4-FLUOROPHENYL)-1-(4-HYDROXYBENZYL)ISOINDOLIN-5-OL

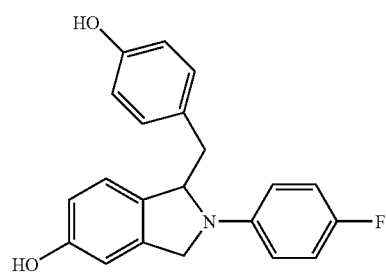

To a solution of 2-(4-fluorophenyl)-5-methoxy-1-{4-[(2-piperidyl)ethoxy]benzyl}isoindoline (0.14 g, 0.3 mmol) in $CH_2Cl_2$ (8 mL) under nitrogen at $-10°$ C. was added a 1.0 M solution of boron tribromide in $CH_2Cl_2$ (0.6 mL, 0.6 mmol) dropwise. After stirring at $-10°$ C. for 1 hour, the reaction was quenched with ice and saturated sodium bicarbonate, then extracted with methylene chloride. The organic layer was dried over $MgSO_4$, filtered, and concentrated. The residue was then purified by HPLC (C-18 column, 10-100% acetonitrile/water with 0.1% trifluoroacetic acid) to provide the title compound (0.084 g, 84% yield): 1H NMR (DMSO-d6) 7.04 (t, 2H), 6.88 (d, 1H), 6.69 (dd, 1H), 6.61-6.65 (m, 5H), 6.56 (d, 1H), 5.21 (m, 1H), 4:67 (s, 1H), 4.51 (s, 1H), 4.29 (d 1H), 4.10 (dd, 1H), 3.00-3.14 (m, 2H); ES-MS (m/z) 336 $[M+H]^+$.

Example 139

SYNTHESIS OF 2-(4-FLUOROPHENYL)-1-{4-[(2-PIPERIDYL)ETHOXY]BENZOYL}-1,2,3,4-TETRAHYDROISOQUINOLIN-6-OL

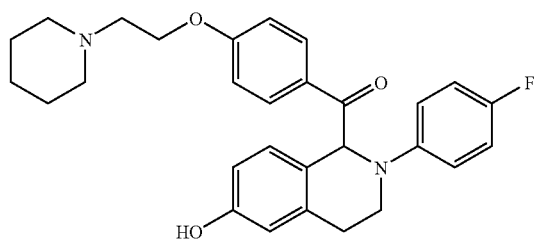

Reaction Scheme
Scheme for Example 139

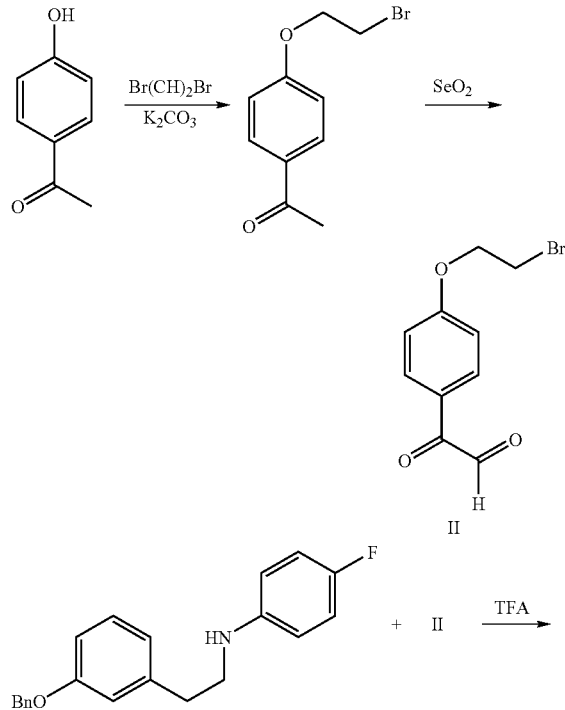

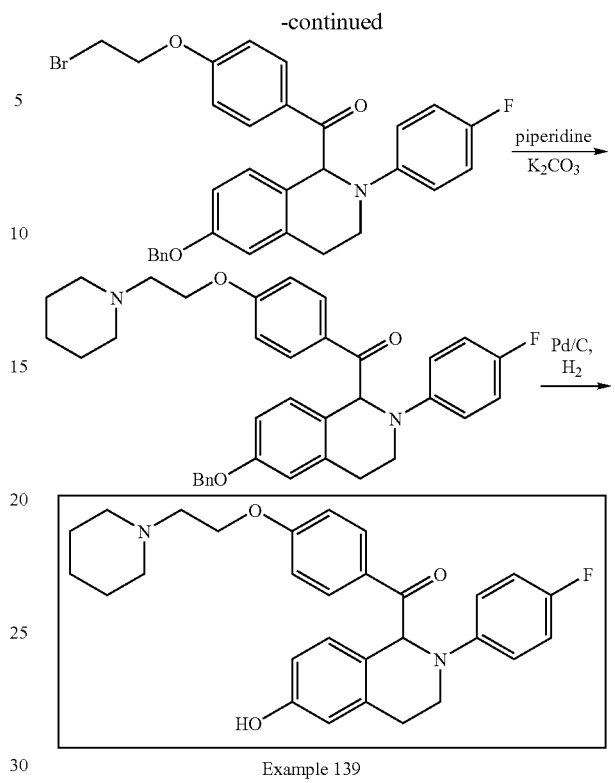

Example 139

A. 1-[4-(2-Bromoethoxy)phenyl]ethanone

A mixture of 1-(hydroxyphenyl)ethanone (2.72 g, 20.0 mmol), 1,2-dibromoethane (7.676 g, 40.0 mmol), and potassium carbonate (5.52 g, 40 mmol) in dried dimethylformamide (40 mL) was heated at 50° C. overnight. The reaction was quenched with water and extracted with ethyl acetate. The organic layer was dried over $MgSO_4$, filtered, concentrated, and purified by column chromatography ($SiO_2$, 20-70% ethyl acetate/hexane) to provide the title compound (1.91 g, 39% yield): $^1$H NMR ($CDCl_3$) 7.95 (t, 2H), 6.95 (t, 2H), 4.36 (t, 2H), 3.67 (t, 2H), 2.57 (s, 3H); ES-MS (m/z) 243 $[M+H]^+$.

B. [4-(2-Bromoethoxy)phenyl]glyoxal

A suspension of selenium dioxide (0.821 g, 7.4 mmol) in 1,4-dioxane (40 mL) and water (3 mL) was heated at 55° C. until selenium dioxide was dissolved. To the solution was added 1-[4-(2-bromoethoxy)phenyl]ethanone (1.80 g, 7.4 mmol), and the reaction was heated to reflux for 4 hours. The reaction was filtered, concentrated, and purified by column chromatography ($SiO_2$, 50% ethyl acetate/hexane) to provide the title compound (1.853 g, 97% yield): ES-MS (m/z) 257 $[M+H]^+$.

C. 1-[4-(2-Bromethoxy)benzoyl]-2-(4-fluorophenyl)-6-(phenylmethoxy)-1,2,3,4-tetrahydroisoquinoline To a solution of (4-fluorophenyl){2-[3-(phenylmethoxy)phenyl]ethyl}amine (0.643 g, 2.0 mmol) and [4-(2-bromoethoxy)phenyl]glyoxal (0.617 g, 2.4 mmol) was added trifluoroacetic acid (0.342 g, 3.0 mmol). The reaction stirred at room temperature for 4 hours. The reaction was quenched with saturated sodium bicarbonate and extracted with ethyl acetate. The organic layer was dried over MgSO₄, filtered, concentrated, and purified by column chromatography (SiO₂, 20% ethyl acetate/hexane) to provide the title compound (0.879 g, 78% yield): ¹H NMR (CDCl₃) 8.00 (d, 2H), 7.40 (m, 4H), 7.18 (m, 1H), 7.07 (d, 1H), 6.79-6.92 (m, 8H), 5.85 (s, 1H), 5.02 (s, 2H), 4.33 (t, 2H), 3.71 (m, 1H), 3.64 (t, 2H), 3.47 (m, 1H), 3.07 (m, 1H), 2.87 (m, 1H); ES-MS (m/z) 560 [M+H]⁺.

D. 2-(4-Fluorophenyl)-1-{4-[(2-piperidyl)ethoxy]benzoyl}-6-(phenylmethoxy)-1,2,3,4-tetrahydroisoquinoline A solution of 1-[4-(2-bromethoxy)benzoyl]-2-(4-fluorophenyl)-6-(phenylmethoxy)-1,2,3,4-tetrahydroisoquinoline (0.80 g, 1.43 mmol) and piperidine (0.86 g, 10.1 mmol) in dimethylformamide was stirred at room temperature for 3 hours. The reaction was quenched with brine and extracted with ethyl acetate. The organic layer was dried over MgSO₄, filtered, concentrated, and purified by chromatography (SiO₂, ethyl acetate and 3-5% methanol/ethyl acetate) to provide the title compound (0.594 g, 74% yield): ¹H NMR (CDCl₃) 8.00 (m, 2H), 7.40 (m, 4H), 6.79-6.92 (m, 10H), 5.87 (s, 1H), 5.02 (s, 2H), 4.15 (t, 2H), 3.72 (m, 1H), 3.48 (m, 1H), 3.07 (m, 1H), 2.79 (t and m, 3H), 2.51 (m, 4H), 1.61 (m, 4H), 1.46 (m, 2H); ES-MS (m/z) 565 [M+H]⁺.

E. 2-(4-Fluorophenyl)-1-{4-[(2-piperidyl)ethoxy]benzoyl}-1,2,3,4-tetrahydroisoquinolin-6-ol The title compound was prepared as described in Example 14.D, using 2-(4-fluorophenyl)-1-{4-[(2-piperidyl)ethoxy]benzoyl}-6-(phenylmethoxy)-1,2,3,4-tetrahydroisoquinoline (0.35 g, 0.62 mmol) to provide the title compound (0.039 g, 13% yield): ¹H NMR (CDCl₃) 7.96 (d, 2H), 6.79-7.00 (m, 7H), 6.56-6.63 (m, 2H), 5.83 (s, 1H), 4.16 (t, 2H), 3.69 (m, 1H), 3.44 (m, 1H), 3.04 (m 1H), 2.84 (t, 2H), 2.79 (m, 1H), 2.59 (m, 4H), 1.64 (m, 4H), 1.46 (m, 2H); ES-MS (m/z) 475 [M+H]⁺.

Example 140

ER-Selectivity in U2OS Osteosarcoma Cells

Human U2OS osteosarcoma cells (ATCC) were stably transfected with expression vectors for human full-length ER-α or ER-β, respectively, using standard molecular biology techniques. Stable subclones were generated that expressed high levels of ER-α or ER-β mRNA. The expression of ER-α and ER-β was confirmed using RNase protection analysis. The parental U2OS cells did not express any measurable amounts of either ER-α or ER-β.

Cells were plated into 96-well plates at a density of 8000 cells per well in phenol red-free media with charcoal-stripped fetal calf serum. Twenty-four hours later, cells were either treated with vehicle (0.2% DMSO) or test compound at the concentrations indicated (in 0.2% DMSO). Thirty minutes later cells were stimulated with 10 ng/ml IL-1β and 10 ng/ml TNF-α. Twenty-four hours later the media supernatant was analyzed for cytokine production (IL-6) using commercially available ELISA kits following the manufacturer's instructions. Cytokine production in the presence of vehicle (0.2% DMSO) was set to 100%.

Results of this assay are set forth in Table 4 for a number of representative compounds of this invention, as well as for the prior art test compounds. In this table, activity is expressed as IC₅₀ calculated by 50% inhibition relative to DMSO control (100%). In this experiment, the prior art test compounds were 17-β-Estradiol, Raloxifene Hydrochloride, 4-Hydroxy-Tamoxifen, and the following compound disclosed in published PCT WO 96/21656 (referred to herein as "Compound A"):

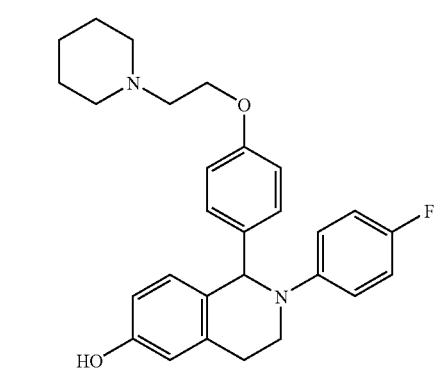

Compound A

TABLE 4

Effect of Representative SERMs on Cytokines

| Compound | U2OS IL-6 ER-α IC₅₀ (nM) | U2OS IL-6 ER-β IC₅₀ (nM) | U2OS IL-6 ER-Minus IC₅₀ (nM) |
|---|---|---|---|
| Compound A | 1 | >10,000 | >10,000 |
| 17-β-Estradiol | 0.03 | 0.016 | >1000 |
| Raloxifene Hydrochloride | 3 | 10,000 | >1000 |
| 4-Hydroxy-Tamoxifen | 0.3-3 | >1000 | >1000 |
| Example 2 | >1000 | 107 | >1000 |
| Example 5 | 2008 | 285 | >10,000 |
| Example 8 | 10,000 | 5,000 | >10,000 |

Referring to the above table, representative compounds of this invention showed specificity for ER-β over ER-α, while the prior art compounds (with the exception of 17-β-Estradiol) were selective for ER-α over ER-β. In this regard, preferred components of this invention have an IC₅₀ of less than 1 μM, and more preferably 500 nM or less.

Example 141

ER-Selectivity in Breast Cancer Cells

Tamoxifen resistant breast cancer cells, in this case LCC1 and LCC2 cells (R. Clarke, Georgetown University), were plated in 96-well dishes at 5000 cells per well in phenol-red free medium containing 5% charcoal-stripped serum. Three hours later, test compounds were prepared by serial dilution and added to the cells to yield a final concentration of 0.2% DMSO. Compounds were prepared fresh and added daily for 4 days with media change after 48 hours. On the fifth day, [3H]-thymidine (2.5 μCi/ml) was added to each well of the 96-well dish and the plate incubated at 37° C. for 6 hours. At the end of the incubation, the cells were lysed and the [3H]-thymidine incorporated determined using a scintillation counter.

The results of this experiment for Compound 102 (Example No. 5) of this invention are set forth in FIG. 1A for LCC1 cells, and FIG. 1B for LCC2 cells. This experiment evidences that representative compounds of this invention are effective in Tamoxifen-resistant breast cancer cell lines.

It will be appreciated that, although specific embodiments of the invention have been described herein for purpose of illustration, various modifications may be made without departing from the spirit and scope of the invention. Accordingly, the invention is not limited except as by the appended claims.

The invention claimed is:

1. A method for modulating ER-β in a breast cancer cell or bone cancer cell expressing ER-β, comprising contacting the cell with an effective amount of a compound having the structure:

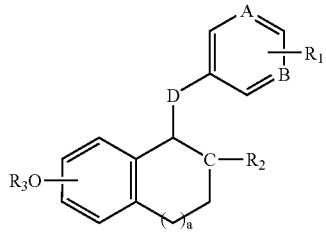

or a pharmaceutically acceptable salt thereof;
wherein
a is 0, 1 or 2;
A, B and C are independently CH, CR or N;
D is —(CH$_2$)$_r$— or —(CH$_2$)$_n$C(=O)(CH$_2$)$_m$—;
R$_1$ represents one or two substituents independently selected from —X—Y;
R$_2$ is C$_{1-8}$ alky, C$_{6-12}$aryl, C$_{7-12}$aralkyl, —C(=O)R$_5$, a five- or six-membered heterocycle or heterocyclealkyl containing up to two heteroatoms selected from O, NR$_c$ and S(O)$_q$, or a bicyclic ring system contain a five- or six-membered heterocycle fused to phenyl, wherein each of the above groups are optionally substituted with one to three substituents independently selected from —X—Y or R$_4$; and
R$_3$ is hydrogen, —R$_6$, —(CH$_2$)$_s$C(=O)R$_6$, —(CH$_2$)$_s$C(=O)OR$_6$, —(CH$_2$)$_s$C(=O)NR$_6$R$_7$, —(CH$_2$)$_s$C(=O)NR$_6$(CH$_2$)$_n$C(=O)R$_7$R$_8$, —(CH$_2$)$_s$NR$_6$C(=O)R$_7$, —(CH$_2$)NR$_6$C(=O)NR$_7$R$_8$, —(CH$_2$)$_s$NR$_6$R$_7$, —(CH$_2$)$_s$OR$_6$, —(CH$_2$)$_s$SO$_q$R$_6$ or —(CH$_2$)$_s$SO$_2$NR$_6$R$_7$, and wherein
R$_4$ is at each occurrence independently halogen, hydroxy, carboxy, C$_{1-6}$alkyl, C$_{1-4}$alkoxy, C$_{1-4}$haloalkyl, acyloxy, C$_{1-4}$thio, C$_{1-4}$alkylsulfinyl, C$_{1-4}$alkylsulfonyl, (hydroxy)C$_{1-4}$alkyl, C$_{6-12}$aryl, C$_{7-12}$aralkyl, —C(=O)OH, —C(=O)OR, —OC(=O)R, —C(=O)NHR, —C(=O)NRR, —C(=O)NHOR, —SO$_2$NHR, —NHSO$_2$R, —CN, —NO$_2$, C$_{1-4}$alkylamino, C$_{1-4}$dialkylamino, —NHC(=O)R, NHC(=O)(CH$_2$)$_s$(five- or six-membered heterocycle), a five- or six-membered heterocycle, or a five-or six-membered heterocycle fused to phenyl;
R$_5$, R$_6$, R$_7$ and R$_8$ are at each occurrence independently hydrogen, C$_{1-8}$alkyl, C$_{6-12}$aryl, C$_{7-12}$aralkyl, or a five- or six-membered heterocycle or heterocyclealkyl containing up to two heteroatoms selected from 0, NR$_c$ and S(O)$_q$, wherein each of the above groups are optionally substituted with one to three substituents independently selected from R$_4$;
X is at each occurrence independently a direct bond; —(CH$_2$)$_n$Z(CH$_2$)$_m$—; —O(CH$_2$)$_n$Z(CH$_2$)$_m$—; —S(CH$_2$)$_n$Z(CH$_2$)$_m$—; —NR$_c$(CH$_2$)$_n$Z(CH$_2$)$_m$—; —O(CH$_2$)$_n$CR$_a$R$_b$—; —NR$_c$(CH$_2$)$_n$CR$_a$R$_b$—; —OCHR$_c$CHR$_d$—; or —SCHR$_c$CHR$_d$—;
Y is at each occurrence independently halogen; —R$_e$; —NR$_e$R$_f$;

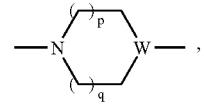

optionally fused on adjacent carbon atoms with one or two phenyl or cycloalkyl rings, and with each carbon optionally and independently substituted with carbonyl or with one or two substituents independently selected from R$_4$, with any two R$_4$ substituents on a single carbon atom optionally being taken together to form a five- or six-membered heterocycle, and with each nitrogen atom optionally and independently substituted with R$_4$, wherein W is —NR$_e$—, —O—, —S— or —CR$_e$R$_f$—; or a bridged or fused C$_{5-12}$bicyclic amine optionally substituted with one to three substituents independently selected from R$_4$;
or where —X—Y is

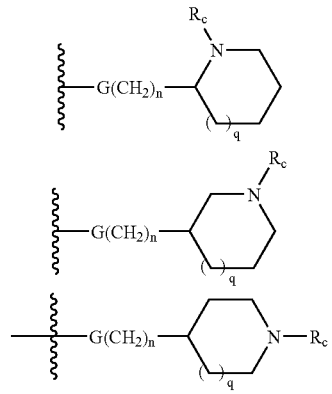

Z is CH$_2$, CH=CH, C≡C, O, NR$_c$, S(O)$_q$, C(=O), C(OH)R$_c$, C(=O)NR$_c$, NR$_c$C(=O), C(=O)NR$_c$, NR$_c$C(=O) or

G is O, S or NR$_e$;
n and m are at each occurrence independently 0, 1, 2 or 3;
p is at each occurrence independently 1, 2 or 3;
q is at each occurrence independently 0, 1 or 2;
r is at each occurrence independently 1, 2, 3, 4 or 5;
s is at each occurrence independently 0, 1, 2, 3 or 4;
R is at each occurrence independently C$_{1-6}$alkyl;
R$_a$ and R$_b$ are at each occurrence independently C$_{1-8}$alkyl or taken together form a C$_{3-8}$cyclic alkyl;
R$_c$ and R$_d$ are at each occurrence independently hydrogen or C$_{1-4}$alkyl; and
R$_e$ and R$_f$ are at each occurrence independently hydrogen, C$_{6-12}$aryl, C$_{1-8}$alkyl, C$_{7-12}$aralkyl, a five- or six-membered heterocycle, or a five- or six membered heterocycle fused to phenyl; or wherein $R_e$ or $R_f$ form a 3-8 membered nitrogen-containing heterocyclic alkyl with $R_a$ or $R_b$; and wherein each $R_e$ and $R_f$ are optionally substituted with up to three substituents independently selected from $R_4$.

2. The method of claim 1 wherein the cell preferentially expresses ER-β over ER-α.

3. The method of claim 2 wherein the cell is a breast cancer cell.

4. A method for modulating ER-β in breast cancer tissue or bone cancer tissue expressing ER-β, comprising contacting the tissue with an effective amount of a compound having the structure:

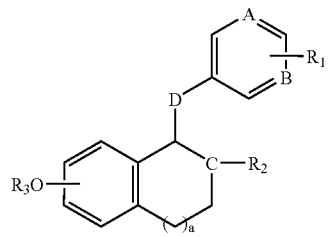

or a pharmaceutically acceptable salt thereof;
wherein
a is 0, 1 or 2;
A, B and C are independently CH, CR or N;
D is $-(CH_2)_r-$ or $-(CH_2)_nC(=O)(CH_2)_m-$;
$R_1$ represents one or two substituents independently selected from —X—Y;
$R_2$ is $C_{1-8}$ alkyl $C_{6-12}$aryl, $C_{7-12}$aralkyl, $-C(=O)R_5$, a five- or six-membered heterocycle or heterocyclealkyl containing up to two heteroatoms selected from O, $NR_c$ and $S(O)_q$, or a bicyclic ring system contain a five- or six-membered heterocycle fused to phenyl, wherein each of the above groups are optionally substituted with one to three substituents independently selected from —X—Y or $R_4$; and
$R_3$ is hydrogen, $-R_6$, $-(CH_2)_sC(=O)R_6$, $-(CH_2)_sC(=O)OR_6$, $-(CH_2)_sC(=O)NR_6R_7$, $-(CH_2)_sC(=O)NR_6(CH_2)_nC(=O)R_7R_8$, $-(CH_2)_sNR_6C(=O)R_7$, $-(CH_2)_sNR_6C(=O)NR_7R_8$, $-(CH_2)_sNR_6R_7$, $-(CH_2)_sOR_6$, $-(CH_2)_sSO_qR_6$ or $-(CH_2)_sSO_2NR_6R_7$;
and wherein
$R_4$ is at each occurrence independently halogen, hydroxy, carboxy $C_{1-6}$alkyl, $C_{1-4}$alkoxy, $C_{1-4}$haloalkyl, acyloxy, $C_{1-4}$thio, $C_{1-4}$alkylsulfinyl, $C_{1-4}$alkylsufonyl, (hydroxy)$C_{1-4}$alkyl, $C_{6-12}$aryl, $C_{7-12}$aralkyl, $-C(=O)OH$, $-C(=O)OR$, $-OC(=O)R$, $-C(=O)NHR$, $-C(=O)NRR$, $-C(=O)NHOR$, $-SO_2NHR$, $-NHSO_2R$, $-CN$, $-NO_2$, $C_{1-4}$alkylamino $C_{1-4}$dialkylamino, $-NHC(=O)R$, $NHC(=O)(CH_2)_s$(five- or six-membered heterocycle), a five- or six-membered heterocycle, or a five-or six-membered heterocycle fused to phenyl;
$R_5$, $R_6$, $R_7$ and $R_8$ are at each occurrence independently hydrogen, $C_{1-8}$alkyl, $C_{6-12}$aryl, $C_{7-12}$aralkyl, or a five- or six-membered heterocycle or heterocyclealkyl containing up to two heteroatoms selected from 0, $NR_c$ and $S(O)_q$, wherein each of the above groups are optionally substituted with one to three substituents independently selected from $R_4$;

X is at each occurrence independently a direct bond; $-(CH_2)_nZ(CH_2)_m-$; $-O(CH_2)_nZ(CH_2)_m-$; $-S(CH_2)_nZ(CH_2)_m-$; $-NR_c(CH_2)_nZ(CH_2)_m-$; $-O(CH_2)_nCR_aR_b-$; $-NR_c(CH_2)_nCR_aR_b-$; $-OCHR_cCHR_d-$; or $-SCHR_cCHR_d-$;

Y is at each occurrence independently halogen; $-R_e$; $-NR_eR_f$;

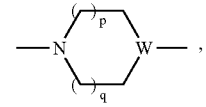

optionally fused on adjacent carbon atoms with one or two phenyl or cycloalkyl rings, and with each carbon optionally and independently substituted with carbonyl or with one or two substituents independently selected from $R_4$, with any two $R_4$ substituents on a single carbon atom optionally being taken together to form a five- or six-membered heterocycle, and with each nitrogen atom optionally and independently substituted with $R_4$, wherein W is $-NR_e-$, $-O-$, $-S-$ or $-CR_eR_f-$; or a bridged or fused $C_{5-12}$bicyclic amine optionally substituted with one to three substituents independently selected from $R_4$;

or where —X—Y is

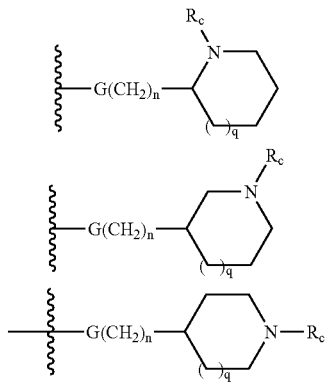

Z is $CH_2$, CH=CH, C≡C, O, $NR_c$, $S(O)_q$, $C(=O)$, C(OH)$R_c$, $C(=O)NR_c$, $NR_cC(=O)$, $C(=O)NR_c$, $NR_cC(=O)$ or

G is O, S or $NR_e$;
n and m are at each occurrence independently 0, 1, 2 or 3;
p is at each occurrence independently 1, 2 or 3;
q is at each occurrence independently 0, 1 or 2;
r is at each occurrence independently 1, 2, 3, 4 or 5;
s is at each occurrence independently 0, 1, 2, 3 or 4;
R is at each occurrence independently $C_{1-6}$alkyl;
$R_a$ and $R_b$ are at each occurrence independently $C_{1-8}$alkyl or taken together form a $C_{3-8}$cyclic alkyl;
$R_c$ and $R_d$ are at each occurrence independently hydrogen or $C_{1-4}$alkyl; and $R_e$ and $R_f$ are at each occurrence independently hydrogen, $C_{6-12}$aryl $C_{1-8}$alkyl, $C_{7-12}$aralkyl, a five- or six-membered heterocycle, or a five- or six membered heterocycle fused to phenyl; or wherein $R_e$ or $R_f$ form a 3-8 membered nitrogen-containing heterocyclic alkyl with $R_a$ or $R_b$; and wherein each $R_e$ and $R_f$ are optionally substituted with up to three substituents independently selected from $R_4$.

5. The method of claim 4 wherein the tissue preferentially expresses ER-β over ER-α.

6. The method of claim 5 wherein the tissue is of bone.

7. A method for treating an estrogen-related condition comprising administering to a patient in need thereof an effective amount of a compound having the structure:

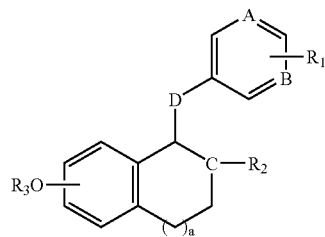

or a pharmaceutically acceptable salt thereof;
wherein
a is 0, 1 or 2;
A, B and C are independently CH, CR or N;
D is —$(CH_2)_r$— or —$(CH_2)_nC(=O)(CH_2)_m$—;
$R_1$ represents one or two substituents independently selected from —X—Y;
$R_2$ is $C_{1-8}$alkyl, $C_{6-12}$aryl, $C_{7-12}$aralkyl, —C(=O)$R_5$, a five- or six-membered heterocycle or heterocyclealkyl containing up to two heteroatoms selected from O, $NR_c$ and S(O)$_q$, or a bicyclic ring system contain a five- or six-membered heterocycle fused to phenyl, wherein each of the above groups are optionally substituted with one to three substituents independently selected from —X—Y or $R_4$; and
$R_3$ is hydrogen, —$R_6$, —$(CH_2)_sC(=O)R_6$, —$(CH_2)_sC(=O)OR_6$, —$(CH_2)_sC(=O)NR_6R_7$, —$(CH_2)_sC(=O)NR_6(CH_2)_nC(=O)R_7R_8$, —$(CH_2)_sNR_6C(=O)R_7$, —$(CH_2)_sNR_6C(=O)NR_7R_8$, —$(CH_2)_sNR_6R_7$, —$(CH_2)_sOR_6$, —$(CH_2)_sSO_qR_6$ or —$(CH_2)_sSO_2NR_6R_7$;
and wherein
$R_4$ is at each occurrence independently halogen, hydroxy, carboxy, $C_{1-6}$alkyl, $C_{1-4}$alkoxy, $C_{1-4}$haloalkyl, acyloxy, $C_{1-4}$thio, $C_{1-4}$alkylsulfinyl, $C_{1-4}$alkylsulfonyl, (hydroxyl)$C_{1-4}$alkyl, $C_{6-12}$aryl, $C_{7-12}$aralkyl, —C(=O)OH, —C(=O)OR, —OC(=O)R, —C(=O)NHR, —C(=O)NRR, —C(=O)NHOR, —SO$_2$NHR, —NHSO$_2$R, —CN, —NO$_2$, $C_{1-4}$alkylamino, $C_{1-4}$dialkylamino, —NHC(=O)R, NHC(=O)(CH$_2$)$_s$(five- or six-membered heterocycle), a five- or six-membered heterocycle, or a five- or six-membered heterocycle fused to phenyl;
$R_5$, $R_6$, $R_7$ and $R_8$ are at each occurrence independently hydrogen, $C_{1-8}$alkyl, $C_{6-12}$aryl, $C_{7-12}$aralkyl, or a five- or six-membered heterocycle or heterocyclealkyl containing up to two heteroatoms selected from 0, $NR_c$ and S(O)$_q$, wherein each of the above groups are optionally substituted with one to three substituents independently selected from $R_4$;
X is at each occurrence independently a direct bond; —$(CH_2)_nZ(CH_2)_m$—; —O$(CH_2)_nZ(CH_2)_m$—; —S$(CH_2)_nZ(CH_2)_m$—; —$NR_c(CH_2)_nZ(CH_2)_m$—;
—O$(CH_2)_nCR_aR_b$—; —$NR_c(CH_2)_nCR_aR_b$—; —OCHR$_c$CHR$_d$—; or —SCHR$_c$CHR$_d$—;
Y is at each occurrence independently halogen; —$R_e$; —$NR_eR_f$;

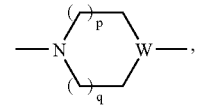

optionally fused on adjacent carbon atoms with one or two phenyl or cycloalkyl rings, and with each carbon optionally and independently substituted with carbonyl or with one or two substituents independently selected from $R_4$, with any two $R_4$ substituents on a single carbon atom optionally being taken together to form a five- or six-membered heterocycle, and with each nitrogen atom optionally and independently substituted with $R_4$, wherein W is —$NR_e$—, —O—, —S— or —$CR_eR_f$—; or a bridged or fused $C_{5-12}$bicyclic amine optionally substituted with one to three substituents independently selected from $R_4$;
or where —X—Y is

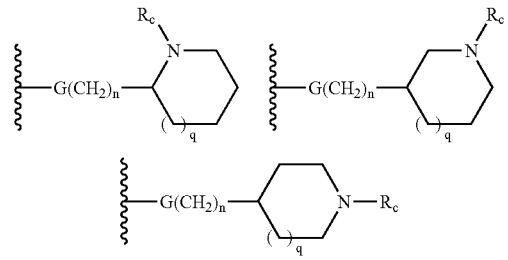

Z is $CH_2$, CH=CH, C≡C, O, $NR_c$, S(O)$_q$, C(=O), C(OH)$R_c$, C(=O)$NR_c$, $NR_cC(=O)$, C(=O)$NR_c$, $NR_cC(=O)$ or

G is O, S or $NR_e$;
n and m are at each occurrence independently 0, 1, 2 or 3;
p is at each occurrence independently 1, 2 or 3;
q is at each occurrence independently 0, 1 or 2;
r is at each occurrence independently 1, 2, 3, 4 or 5;
s is at each occurrence independently 0, 1, 2, 3 or 4;
R is at each occurrence independently $C_{1-6}$alkyl;
$R_a$ and $R_b$ are at each occurrence independently $C_{1-8}$alkyl or taken together form a $C_{3-8}$cyclic alkyl;
$R_c$ and $R_d$ are at each occurrence independently hydrogen or $C_{1-4}$alkyl; and
$R_e$ and $R_f$ are at each occurrence independently hydrogen, $C_{6-12}$aryl, $C_{1-8}$alkyl, $C_{7-12}$aralkyl, a five- or six-membered heterocycle, or a five- or six membered heterocycle fused to phenyl; or wherein $R_e$ or $R_f$ form a 3-8 membered nitrogen-containing heterocyclic alkyl with $R_a$ or $R_b$; and wherein each $R_e$ and $R_f$ are optionally substituted with up to three substituents independently selected from $R_4$,
wherein the estrogen-related condition is breast cancer or bone cancer.

* * * * *